(12) United States Patent
Daunert et al.

(10) Patent No.: US 11,249,082 B2
(45) Date of Patent: Feb. 15, 2022

(54) ZIKA VIRUS ASSAY SYSTEMS

(71) Applicant: UNIVERSITY OF MIAMI, Miami, FL (US)

(72) Inventors: Sylvia Daunert, Miami, FL (US); Sapna K. Deo, Miami, FL (US); Emre Dikici, Miami, FL (US); Marcello Mascini, Teramo (IT); Devon Pawley, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 0 days.

(21) Appl. No.: 16/441,388

(22) Filed: Jun. 14, 2019

(65) Prior Publication Data

US 2019/0317094 A1    Oct. 17, 2019

Related U.S. Application Data

(63) Continuation-in-part of application No. 16/345,943, filed as application No. PCT/US2017/059129 on Oct. 30, 2017, now abandoned.

(60) Provisional application No. 62/414,674, filed on Oct. 29, 2016.

(51) Int. Cl.
| | |
|---|---|
| A61K 9/00 | (2006.01) |
| A61K 39/00 | (2006.01) |
| A61K 39/12 | (2006.01) |
| C07D 401/14 | (2006.01) |
| C07D 403/14 | (2006.01) |
| G01N 33/569 | (2006.01) |

(52) U.S. Cl.
CPC ... *G01N 33/56983* (2013.01); *G01N 2469/10* (2013.01)

(58) Field of Classification Search
CPC ...... Y02A 50/30; A61K 39/12; C07D 403/14; C07D 487/04; C12Q 1/6816
See application file for complete search history.

(56) References Cited

U.S. PATENT DOCUMENTS

| | | | |
|---|---|---|---|
| 4,946,778 A | 8/1990 | Ladner et al. |
| 5,225,539 A | 7/1993 | Winter |
| 5,403,484 A | 4/1995 | Ladner et al. |
| 5,545,806 A | 8/1996 | Lonberg et al. |
| 5,569,825 A | 10/1996 | Lonberg et al. |
| 5,571,698 A | 11/1996 | Ladner et al. |
| 5,585,089 A | 12/1996 | Queen et al. |
| 5,639,641 A | 6/1997 | Pedersen et al. |
| 5,693,761 A | 12/1997 | Queen et al. |
| 5,693,762 A | 12/1997 | Queen et al. |
| 5,702,892 A | 12/1997 | Mulligan-Kehoe |
| 5,714,352 A | 2/1998 | Jakobobits et al. |
| 5,780,279 A | 7/1998 | Matthews et al. |
| 5,821,047 A | 10/1998 | Garrard et al. |
| 5,824,520 A | 10/1998 | Mulligan-Kehoe |
| 5,837,500 A | 11/1998 | Ladner et al. |
| 5,855,885 A | 1/1999 | Smith et al. |
| 5,858,657 A | 1/1999 | Winter et al. |
| 5,871,907 A | 2/1999 | Winter et al. |
| 5,969,108 A | 10/1999 | McCafferty et al. |
| 6,057,098 A | 5/2000 | Buechler et al. |
| 6,225,447 B1 | 5/2001 | Winter et al. |
| 6,265,150 B1 | 7/2001 | Terstappen et al. |
| 6,551,592 B2 | 4/2003 | Lindhofer et al. |
| 6,699,843 B2 | 3/2004 | Pietras et al. |
| 7,355,008 B2 | 4/2008 | Stavenhagen et al. |
| 7,381,408 B2 | 6/2008 | Mezo et al. |
| 2002/0197266 A1 | 12/2002 | Debinski |
| 2005/0282233 A1 | 12/2005 | Eriksson et al. |
| 2009/0081230 A1 | 3/2009 | Lanzavecchia et al. |
| 2011/0171241 A1 | 7/2011 | Dix et al. |
| 2012/0020957 A1 | 1/2012 | Lanzavecchia |
| 2017/0336404 A1 | 11/2017 | Ali |

FOREIGN PATENT DOCUMENTS

| | | | |
|---|---|---|---|
| CN | 105954512 A | | 9/2016 |
| EP | 0239400 B1 | | 8/1994 |
| GB | 2188638 A | | 10/1987 |
| WO | 2005/087812 A1 | | 9/2005 |
| WO | 2010/051007 A1 | | 5/2010 |
| WO | 2016/022071 A1 | | 2/2016 |
| WO | WO2016022071 | * | 2/2016 |
| WO | 2016/069245 A1 | | 5/2016 |
| WO | 2017/197477 A1 | | 11/2017 |

OTHER PUBLICATIONS

Huzly et al., "High specificity of a novel Zika virus ELISA in European patients after exposure to different flaviviruses", Euor Survelliance, 2016, 21(16):1-4.*
Lo, Benny, Antibody Engineering: Methods and Protocols, 248 (2004).
Loos et al., Current Zika virus epidemiology and recent epidemics, Medecine ET maladies infectieuses, 44(7):302-307 (2014).
Macalino et al., Role of computer-aided drug design in modern drug discovery, Archives of pharmacal. research, 38(9):1686-1701 (2015).
Magnani et al., A human inferred germline antibody binds to an immunodominant epitope and neutralizes Zika virus, PLoS Negl. Trop. Dis., 11:39-42:1-17, e0005655 (2017).
Magnani et al., Neutralizing human monoclonal antibodies prevent Zika virus infection in macaques, Science translational medicine, 9(410):eaan8184 (2017).
Marvin et al., Recombinant approaches to IgG-like bispecific antibodies, Acta. Pharmacologica. Sinica., 26:649-658 (2005).
Mascini et al., Hairpin DNA-AuNPs as molecular binding elements for the detection of volatile organic compounds, Biosensors and Bioelectronics, 123:124-130 (2019).

(Continued)

*Primary Examiner* — Barry A Chestnut
(74) *Attorney, Agent, or Firm* — Marshall, Gerstein & Borun LLP

(57) ABSTRACT

Provided herein are Zika virus (ZIKV) binding constructs, e.g., antibodies and antigen-binding fragments thereof and antibody mimetics, as well as related conjugates, polypeptides, nucleic acids, expression vectors, host cells, kits, and assay systems. Methods detecting ZIKV infection and/or ZIKV exposure and/or ZIKV immunity are provided.

7 Claims, 9 Drawing Sheets

Specification includes a Sequence Listing.

(56) References Cited

OTHER PUBLICATIONS

Mascini et al., Selective solid phase extraction of JWH synthetic cannabinoids by using computationally designed peptides, Talanta, 167:126-133 (2017).
McEnaney et al., Chemically Synthesized Molecules with the Targeting and Effector Functions of Antibodies, J. Am. Chem. Soc., 136(52):18034-18043 (2014).
Michaeli et al., Computationally Designed Bispecific MD2/CD14 Binding Peptides Show TLR4 Agonist Activity, The Journal of Immunology, 201(11):3383-3391 (2018).
Morrison et al., Chimeric human antibody molecules: mouse antigen-binding domains with human constant region domains, Proc. Natl. Acad. Sci., 81:6851-6855 (1984).
Neuberger et al., Recombinant antibodies possessing novel effector functions, Nature 312:604-608 (1984).
OE Docking. version 3.0.0. Open Eye Scientific Software, Santa Fe, NM. http://www.eyesopen.com.
Omega. version 2.4.6. OpenEye Scientific Software, Santa Fe, NM. http://www.eyesopen.com.
Orlandi et al., Cloning immunoglobulin variable domains for expression by the polymerase chain reaction, Proc Natl Acad Sci., 86:3833-3837 (1989).
Palzkill et al., US Patent App. (2018), U.S. Appl. No. 14/777,714.
Pawley et al., Highly Sensitive and Selective Direct Detection of Zika Virus Particles in Human Bodily Fluids for Accurate Eady Diagnosis of Infection, ACS Omega, 4(4):6808-6818 (2019).
Pedersen et al., Comparison of Surface Accessible Residues in Human and Murine Immunoglobulin Fv Domains: Implication for Humanization of Murine Antibodies, Journal of Molecular Biology, 235:959-973 (1994).
Perez et al., Peptides trapping dioxins: a docking-based inverse screening approach, Journal of Chemistry, 2013.
Pharmaceutics and Pharmacy Practice, J. B. Lippincott Company, Philadelphia, PA, Banker and Chalmers, eds., 238-250 (1982).
Pichon et al., Aptamer-based-sorbents for sample treatment—a review, Anal Bioanal Chem., 407(3):681-698, doi 10.1007/s00216-014-8129-5 (2015).
Priyamvada et al., Human antibody responses after dengue virus infection are highly cross-reactive to Zika virus, Proceedings of the National Academy of Sciences, 113(28):7852-7857 (2016).
Protein production and purification, Nature Methods, 5(2):135-146 (2008).
Rajkovic et al., Immunoquantitative real-time PCR for detection and quantification of *Staphylococcus aureus* enterotoxin B in foods, Applied and Environmental Microbiology, 72(10):6593-6599 (2006).
Reiter et al., Engineering interchain disulfide bonds into conserved framework regions of Fv fragments: improved biochemical characteristics of recombinant immunotoxins containing disulfide-stabilized Fv, Protein Engineering, 7:697-704 (1994).
Roder et al., The EBV-hybridoma technique, Methods in Enzymology, 121:140-167 (1986).
Roque et al., Antibodies and genetically engineered related molecules: production and purification, Biotechnology Progressg, 20(3):639-54 (2004).
Routledge et al., The effect of aglycosylation on the immunogenicity of a humanized therapeutic CD3 monoclonal antibody, Transplantation, 60:847-853, (1995).
Sambrook et al., Molecular Cloning: A Laboratory Manual, 2nd Edition, Cold Spring Harbor, New York (1989).
Sankaranarayanan et al., Broadly Neutralizing Antibodies for therapy of viral Infections, Antibody Tech. Journal, 6:1-15 (2016).
Shields et al., High resolution mapping of the binding site on human IgG1 for Fc gamma RI, Fc gamma RII, Fc gamma RIII, and FcRn and design of IgG1 variants with improved binding to the Fc gamma R, J. Biol. Chem., 276:6591-6604 (2001).
Shukla et al. "Rapid Detection Strategies for the Global Threat of Zika Virus: Current State, New Hypotheses, and Limitations," Frontiers in Microbiology, Oct. 24, 2014 (Oct. 24, 2016), vol. 7, Art. 1685, pp. 1-15. entire document.

Singh et al., Rational Design of Small Peptides for Optimal Inhibition of Cyclooxygenase-2: Development of a Highly Effective Anti-Inflammatory Agent, Journal of medicinal chemistry, 59(8):3920-3934 (2016).
Sirohi et al., The 3.8 A resolution cryo-EM structure of Zika virus, Science, 352(6284):467-470 (2016).
Stettler et al., Specificity, cross-reactivity, and function of antibodies elicited by Zika virus infection, Science, 353(6301):823-826 (2016).
Stobiecka et al., Biosensors based on molecular beacons, Chemical Papers, 69:62-76 (2015).
Szybki. version 1.5.7. OpenEye Scientific Software, Santa Fe, NM. http://www.eyesogen.com.
Takahashi et al., Induction of CD8+ cytotoxic T cells by immunization with purified HIV-1 envelope protein in ISCOMs, Nature, 344:873-875 (1990).
Takeda et al., Construction of chimaeric processed immunoglobulin genes containing mouse variable and human constant region sequences, Nature, 314:452-454 (1985).
Tambunan et al., Designing disulfide cyclic peptide as fusion inhibitor that targets denv envelope proteine, Jurnal Teknologi, 78:4-3 (2016).
Tang et al., Quantum dot-DNA aptamer conjugates coupled with capillary electrophoresis: A universal strategy for ratiometric detection of organophosphorus pesticides, Talanta, 146:55-61 (2016).
Titus et al., Human T cells targeted with anti-T3 cross-linked to antitumor antibody prevent tumor growth in nude mice, J. Immunol., 138:4018-4022 (1987).
Todorovska et al., Design and application of diabodies, triabodies and tetrabodies for cancer targeting, Journal of Immunological Methods, 248:47-66, (2001).
Tomasevic et al., A high affinity recombinant antibody to the human EphA3 receptor with enhanced ADCC activity, Growth Factors, 32:223-235 (2014).
Trissel, 4th ed., ASHP Handbook on Injectable Drugs, Intravenous infusion solutions, 622-630 (1986).
Tsekenis et al., Label-less immunosensor assay for myelin basic protein based upon an ac impedance protocol, Analytical Chemistry, 80(6):2058-2062 (2008).
Vida. version 4.1.1. OpenEye Scientific Software, Santa Fe, NM. http://www.eyesogen.com.
Warren et al, Future prospects for vaccine adjuvants, CRC Critical Reviews in Immunology, 8:83-101 (1988).
Weaver et al., Zika virus: History, emergence, biology, and prospects for control, Antiviral research, 130:69-80 (2016).
Winter et al., Man-made antibodies, Nature, 349:293-299 (1991).
Woodlock et al., Active specific immunotherapy for metastatic colorectal carcinoma: phase I study of an allogeneic cell vaccine plus low-dose interleukin-1 alpha, J. Immunother., 22:251-259 (1999).
Xu et al., Epitope-based vaccine design yields fusion peptide-directed antibodies that neutralize diverse strains of HIV-1, Nature medicine, 24(6):857-867 (2018).
Yu et al., Beyond Antibodies as Binding Partners: The Role of Antibody Mimetics in Bioanalysis, Annual Review of Analytical Chemistry, 10:293-320 (2017).
Yuan et al., Using PyMOL as a platform for computational drug design, Computational Molecular Science, 7:e1298 (2017).
Zhao et al., Structural Basis of Zika Virus-Specific Antibody Protection, Cell, 166:1016-1027 (2016).
Acebes et al., Rational enzyme engineering through biophysical and biochemical modeling, ACS Catalysis, 6(3), 1624-1629 (2016).
Armour et al., Recombinant human IgG molecules lacking Fcgamma receptor I binding and monocyte triggering activities, Eur. J. Immunol., 29:2613-2624, (1999).
Barba-Spaeth et al., Structural basis of potent Zika-dengue virus antibody cross-neutralization, Nature, 536(7614):48-53 (2016).
Binz and Pluckthun, Engineered proteins as specific binding reagents, Curr Opin Biotechnol., 16(4):459-69 (2005).
Bunker et al., Biochimica et Biophysica Acta (BBA)—Biomembranes, 1858(10):2334-2352 (2016).
Burch et al., Priming Tissue-specific Cellular Immunity in a Phase I Trial of Autologous Dendritic Cells for Prostate Cancer, Clinical Cancer Research, 6(6):2175-2182 (2000).

(56) References Cited

OTHER PUBLICATIONS

Burmeister et al., Crystal structure of the complex of rat neonatal Fc receptor with Fc, Nature, 372:379-383, (1994).
Byrne et al., A tale of two specificities: bispecific antibodies for therapeutic and diagnostic applications, Trends Biotechnol., 31:621-632 (2013).
Campos et al., Prolonged detection of Zika virus RNA in urine samples during the ongoing Zika virus epidemic in Brazil, Journal of Clinical Virology, 77:69-70 (2016).
Chan et al., Therapeutic antibodies for autoimmunity and inflammation, Nat Rev Immunol., 10:301-316 (2010).
Cole et al., Monoclonal Antibodies and Cancer Therapy, Alan R Liss Inc, New York N.Y., 77-96 (1985).
Cote et al., Generation of human monoclonal antibodies reactive with cellular antigens, Proc Natl Acad Sci., 80:2026-2030, 1983.
Cross et al., Analytical Validation of the ReEBOV Antigen Rapid Test for Point-of-Care Diagnosis of Ebola Virus Infection, The Journal of Infectious Diseases, 214(suppl3):S210-S217 (2016).
Cuesta et al., Multivalent antibodies: when design surpasses evolution, Trends in Biotechnology, 28:355-362 (2010).
Dai et al., Structures of the Zika Virus Envelope Protein and Its Complex with a Flavivirus Broadly Protective Antibody, Cell Host & Microbe., 19(5):696-704 (2016).
Davis et al., Single Chain Antibody (SCA) Encoding Genes: One-Step Construction and Expression in Eukaryotic Cells, Nature Biotechnology, 9:165-169 (1991).
Dudley et al., Adoptive cell therapy for patients with metastatic melanoma: evaluation of intensive myeloablative chemoradiation preparative regimens, J. Clin. Oneal., 26:5233-5239 (2008).
Friend et al., Phase I study of an engineered aglycosylated humanized CD3 antibody in renal transplant rejection, Transplantation, 68:1632-1637 (1999).
Gofflot et al., Immuno-quantitative polymerase chain reaction for detection and quantitation of prion protein, Journal of Immunoassay and Immunochemistry, 25(3):241-258 (2004).
Gold et al., Aptamers as Therapeutic And Diagnostic Agents, J. Biotechnol., 74:5-13 (2000).
Gong et al., Peptide Aptamer: a powerful potential tool in plant functional genomics (English Abstract only), Hereditas. 32(6):548-554 (2010).
Gonzalez-Diaz et al., Plasmonic Au/Co/Au nanosandwiches with Enhanced Magneto-Optical Activity, Small, 4(2):202-205 (2008).
Grant et al., A paper-based immunoassay to determine HPV vaccination status at the point-of-care, Vaccine, 34(46):5656-5663 (2016).
Gridelli et al., Efficient Human Fetal Liver Cell Isolation Protocol Based on Vascular Perfusion for Liver Cell-Based Therapy and Case Reporton Cell Transplantation, Liver Transplantation, 18:226-237 (2012).
Harlow and Lane (eds.), Antibodies: A Laboratory Manual, Cold Spring Harbor Press (CSH), (1988).
Harlow et al., Using Antibodies: A Laboratory Manual, Cold Spring Harbor Laboratory Press, (1999).
Haskard and Archer, The production of human monoclonal autoantibodies from patients with rheumatoid arthritis by the EBV-hybridoma technique, Journal of Immunological Methods, 74(2):361-367 (1984).
Hawkins et al., Conformer Generation with OMEGA: Algorithm and Validation Using High Quality Structures from the Protein Databank and Cambridge Structural Database, Journal of Chemical Information and Modeling, 50(4):572-584 (2010), doi: 10.1021/ci100031x.
Hawkins et al., Conformer Generation with OMEGA: Learning from the Data Set and the Analysis of Failures, Journal of Chemical Information and Modeling, 52(11):2919-2936, (2012), doi: 10.1021/ci300314k.
Heffron et al., Antibody responses to Zika virus proteins in pregnant and non-pregnant macaques, PLoS neglected tropical diseases, 12(11):e0006903 (2018).
Holliger et al., Engineered antibody fragments and the rise of single domains, Nat. Biotechnol., 23:1126-1136 (2005).
Hoover et al., Adjuvant active specific immunotherapy for human colorectal cancer: 6.5-year median follow-up of a phase III prospectively randomized trial, J Clin Oncol., 11:390-399 (1993).
Hu et al., Minibody: A Novel Engineered Anti-Carcinoembryonic Antigen Antibody Fragment (Single-Chain Fv-CH3) Which Exhibits Rapid, High-Level Targeting of Xenografts, Cancer Research, 56:3055-3061 (1996).
Huse et al., Generation of a large combinatorial library of the immunoglobulin repertoire in phage lambda, Science, 246:1275-1281 (1989).
Huzly et al., High specificity of a novel Zika virus ELISA in European patients after exposure to different flaviviruses, Euor. Surveillance, 21:1-4 (2016).
Hwang et al., High sensitive and selective electrochemical biosensor: Label-free detection of human norovirus using affinity peptide as molecular binder, Biosensors and Bioelectronics, 87:164-170 (2017).
International Preliminary Reporton Patentability for Corresponding International Application No. PCT/US2017/059128, dated May 9, 2019, 7 pages.
International Preliminary Reporton Patentability for Corresponding International Application No. PCT/US2017/059129, dated on May 9, 2019, 7 pages.
International Search Report and Written Opinion for Corresponding International Application No. PCT/US2017/059128, dated Feb. 16, 2018, 9 pages.
International Search Report and Written Opinion for Corresponding International Application No. PCT/US2017/059129, dated Jan. 18, 2018, 9 pages.
Kabat et al. Sequences of Proteins of Immunological Interest, U.S. Department of Public Health, (1991).
Karpovsky et al., Production of target-specific effector cells using hetero-cross-linked aggregates containing anti-target cell and anti-Fc gamma receptor antibodies, J. Exp. Med., 160:1686-701 (1984).
Kelley et al., POSIT: flexible shape-guided docking for pose prediction, Journal of chemical information and modeling, 55(8):1771-1780 (2015).
Khan et al., Human fetal liver-derived stem cell transplantation as supportive modality in the management of end-stage decompensated liver cirrhosis, Cell Transplant, 19:409-418 (2010).
Kim et al., Development of a novel peptide aptamer-based immunoassay to detect Zika virus in serum and urine, Theranostics, 8(13):3629-3642 (2018).
Koehler et al., Continuous cultures of fused cells secreting antibody of predefined specificity, Nature, 256:495-497, (1975).
Kortt et al., Dimeric and trimeric antibodies: high avidity scFvs for cancer targeting, Biomolecular Engineering, 18:95-108, (2001).
Kozbor et al., The production of monoclonal antibodies from human lymphocytes, Immunol. Today, 4:72-79 (1983).
Li et al., Electrochemical aptamer-based sensors for food and water analysis: A review, Analytica. chimica. acta., (2018).
Lin et al., Selective dispersive solid phase extraction-chromatography tandem mass spectrometry based on aptamer-functionalized UiO-66-NH2 for determination of polychlorinated biphenyls, Journal of Chromatography A, 1446:34-40 (2016).

* cited by examiner

FIGURE 7

Microtiter plate or nitrocellulose membrane

Coat with Capture Molecule = Concanavalin A

Add Zika Virus Sample

Add detection antibody

Add HRP conjugated secondary antibody, substrate and measure signal

- Capture Molecule = Concanavalin A
- Zika virus
- Detection antibody
- HRP conjugated secondary antibody

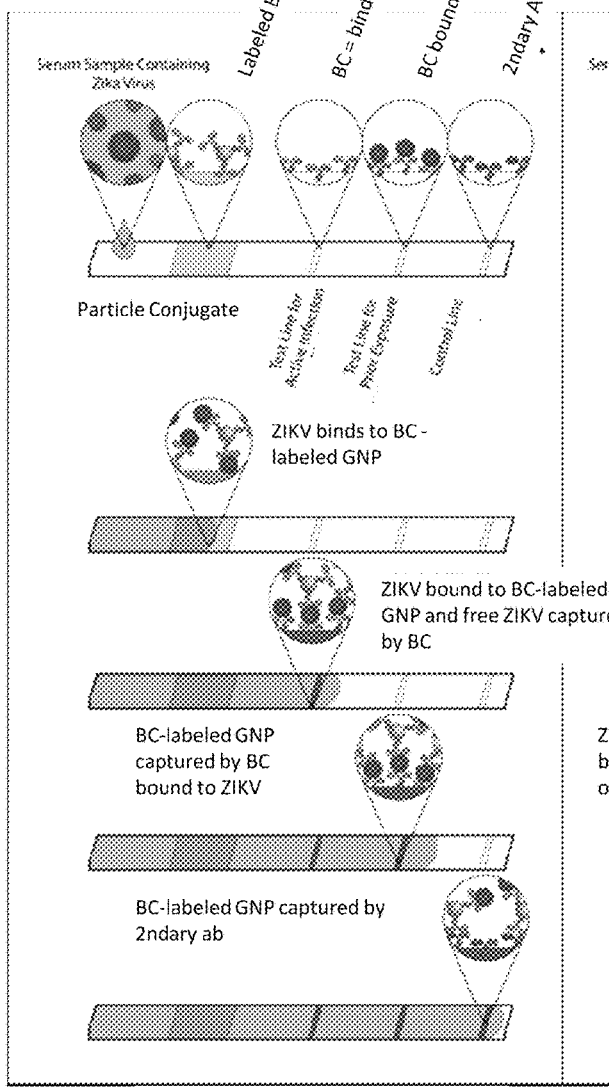
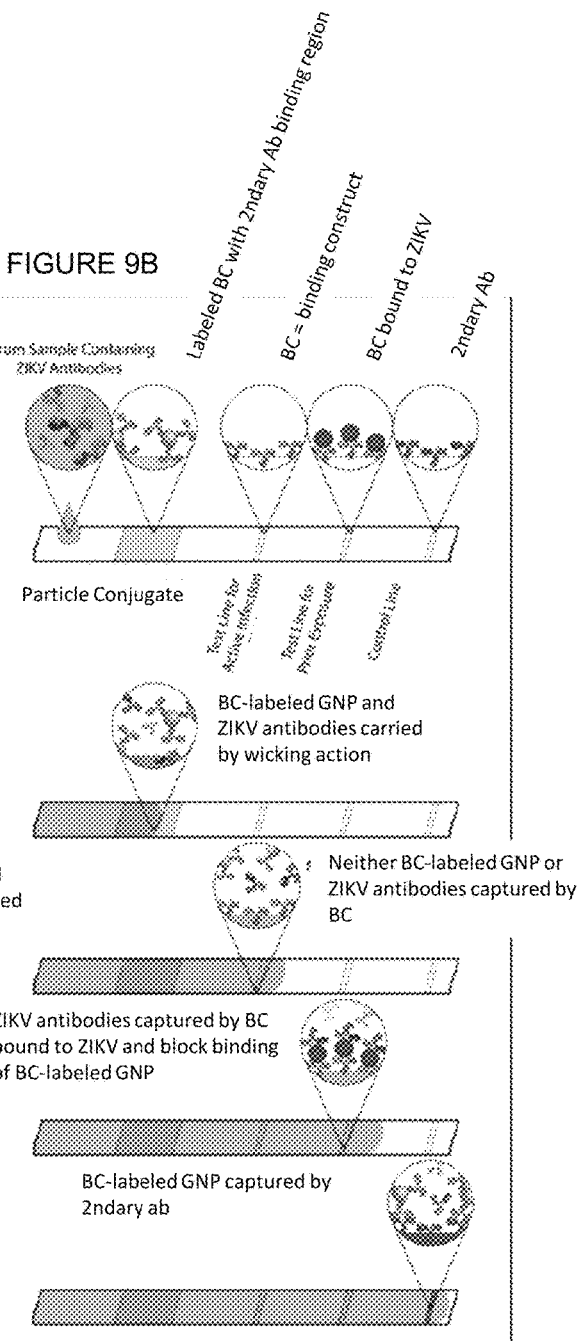

SEQUENCE LISTING

```
<160> NUMBER OF SEQ ID NOS: 40

<210> SEQ ID NO 1
<211> LENGTH: 672
<212> TYPE: PRT
<213> ORGANISM: Zika virus
<300> PUBLICATION INFORMATION:
<308> DATABASE ACCESSION NUMBER: GenBank / KU926309.1
<309> DATABASE ENTRY DATE: 2016-03-21
<313> RELEVANT RESIDUES IN SEQ ID NO: (1)..(672)

<400> SEQUENCE: 1

Ala Glu Val Thr Arg Arg Gly Ser Ala Tyr Tyr Met Tyr Leu Asp Arg
1               5                   10                  15

Asn Asp Ala Gly Glu Ala Ile Ser Phe Pro Thr Thr Leu Gly Met Asn
            20                  25                  30

Lys Cys Tyr Ile Gln Ile Met Asp Leu Gly His Met Cys Asp Ala Thr
        35                  40                  45

Met Ser Tyr Glu Cys Pro Met Leu Asp Glu Gly Val Glu Pro Asp Asp
    50                  55                  60

Val Asp Cys Trp Cys Asn Thr Thr Ser Thr Trp Val Val Tyr Gly Thr
65                  70                  75                  80

Cys His His Lys Lys Gly Glu Ala Arg Arg Ser Arg Arg Ala Val Thr
                85                  90                  95

Leu Pro Ser His Ser Thr Arg Lys Leu Gln Thr Arg Ser Gln Thr Trp
            100                 105                 110

Leu Glu Ser Arg Glu Tyr Thr Lys His Leu Ile Arg Val Glu Asn Trp
        115                 120                 125

Ile Phe Arg Asn Pro Gly Phe Ala Leu Ala Ala Ala Ile Ala Trp
    130                 135                 140

Leu Leu Gly Ser Ser Thr Ser Gln Lys Val Ile Tyr Leu Val Met Ile
145                 150                 155                 160
```

```
Leu Leu Ile Ala Pro Ala Tyr Ser Ile Arg Cys Ile Gly Val Ser Asn
                165                 170                 175
Arg Asp Phe Val Glu Gly Met Ser Gly Gly Thr Trp Val Asp Val Val
            180                 185                 190
Leu Glu His Gly Gly Cys Val Thr Val Met Ala Gln Asp Lys Pro Thr
        195                 200                 205
Val Asp Ile Glu Leu Val Thr Thr Thr Val Ser Asn Met Ala Glu Val
    210                 215                 220
Arg Ser Tyr Cys Tyr Glu Ala Ser Ile Ser Asp Met Ala Ser Asp Ser
225                 230                 235                 240
Arg Cys Pro Thr Gln Gly Glu Ala Tyr Leu Asp Lys Gln Ser Asp Thr
                245                 250                 255
Gln Tyr Val Cys Lys Arg Thr Leu Val Asp Arg Gly Trp Gly Asn Gly
            260                 265                 270
Cys Gly Leu Phe Gly Lys Gly Ser Leu Val Thr Cys Ala Lys Phe Ala
        275                 280                 285
Cys Ser Lys Lys Met Thr Gly Lys Ser Ile Gln Pro Glu Asn Leu Glu
    290                 295                 300
Tyr Arg Ile Met Leu Ser Val His Gly Ser Gln His Ser Gly Met Ile
305                 310                 315                 320
Val Asn Asp Thr Gly His Glu Thr Asp Glu Asn Arg Ala Lys Val Glu
                325                 330                 335
Ile Thr Pro Asn Ser Pro Arg Ala Glu Ala Thr Leu Gly Gly Phe Gly
            340                 345                 350
Ser Leu Gly Leu Asp Cys Glu Pro Arg Thr Gly Leu Asp Phe Ser Asp
        355                 360                 365
Leu Tyr Tyr Leu Thr Met Asn Asn Lys His Trp Leu Val His Lys Glu
    370                 375                 380
Trp Phe His Asp Ile Pro Leu Pro Trp His Ala Gly Ala Asp Thr Gly
385                 390                 395                 400
Thr Pro His Trp Asn Asn Lys Glu Ala Leu Val Glu Phe Lys Asp Ala
                405                 410                 415
His Ala Lys Arg Gln Thr Val Val Val Leu Gly Ser Gln Glu Gly Ala
            420                 425                 430
Val His Thr Ala Leu Ala Gly Ala Leu Glu Ala Glu Met Asp Gly Ala
        435                 440                 445
Lys Gly Arg Leu Ser Ser Gly His Leu Lys Cys Arg Leu Lys Met Asp
    450                 455                 460
Lys Leu Arg Leu Lys Gly Val Ser Tyr Ser Leu Cys Thr Ala Ala Phe
465                 470                 475                 480
Thr Phe Thr Lys Ile Pro Ala Glu Thr Leu His Gly Thr Val Thr Val
                485                 490                 495
Glu Val Gln Tyr Ala Gly Thr Asp Gly Pro Cys Lys Val Pro Ala Gln
            500                 505                 510
Met Ala Val Asp Met Gln Thr Leu Thr Pro Val Gly Arg Leu Ile Thr
        515                 520                 525
Ala Asn Pro Val Ile Thr Glu Ser Thr Glu Asn Ser Lys Met Met Leu
    530                 535                 540
Glu Leu Asp Pro Pro Phe Gly Asp Ser Tyr Ile Val Ile Gly Val Gly
545                 550                 555                 560
Glu Lys Lys Ile Thr His His Trp His Arg Ser Gly Ser Thr Ile Gly
                565                 570                 575
Lys Ala Phe Glu Ala Thr Val Arg Gly Ala Lys Arg Met Ala Val Leu
```

-continued

```
                580                 585                 590
Gly Asp Thr Ala Trp Asp Phe Gly Ser Val Gly Gly Ala Leu Asn Ser
            595                 600                 605

Leu Gly Lys Gly Ile His Gln Ile Phe Gly Ala Ala Phe Lys Ser Leu
        610                 615                 620

Phe Gly Gly Met Ser Trp Phe Ser Gln Ile Leu Ile Gly Thr Leu Leu
625                 630                 635                 640

Met Trp Leu Gly Leu Asn Thr Lys Asn Gly Ser Ile Ser Leu Met Cys
                645                 650                 655

Leu Ala Leu Gly Gly Val Leu Ile Phe Leu Ser Thr Ala Val Ser Ala
            660                 665                 670

<210> SEQ ID NO 2
<211> LENGTH: 234
<212> TYPE: PRT
<213> ORGANISM: Zika virus
<300> PUBLICATION INFORMATION:
<308> DATABASE ACCESSION NUMBER: GenBank / KU926309.1
<309> DATABASE ENTRY DATE: 2016-03-21
<313> RELEVANT RESIDUES IN SEQ ID NO: (90)..(323)

<400> SEQUENCE: 2

Arg Ser Arg Arg Ala Val Thr Leu Pro Ser His Ser Thr Arg Lys Leu
1               5                   10                  15

Gln Thr Arg Ser Gln Thr Trp Leu Glu Ser Arg Glu Tyr Thr Lys His
            20                  25                  30

Leu Ile Arg Val Glu Asn Trp Ile Phe Arg Asn Pro Gly Phe Ala Leu
        35                  40                  45

Ala Ala Ala Ala Ile Ala Trp Leu Leu Gly Ser Ser Thr Ser Gln Lys
    50                  55                  60

Val Ile Tyr Leu Val Met Ile Leu Leu Ile Ala Pro Ala Tyr Ser Ile
65                  70                  75                  80

Arg Cys Ile Gly Val Ser Asn Arg Asp Phe Val Glu Gly Met Ser Gly
                85                  90                  95

Gly Thr Trp Val Asp Val Val Leu Glu His Gly Gly Cys Val Thr Val
            100                 105                 110

Met Ala Gln Asp Lys Pro Thr Val Asp Ile Glu Leu Val Thr Thr Thr
        115                 120                 125

Val Ser Asn Met Ala Glu Val Arg Ser Tyr Cys Tyr Glu Ala Ser Ile
    130                 135                 140

Ser Asp Met Ala Ser Asp Ser Arg Cys Pro Thr Gln Gly Glu Ala Tyr
145                 150                 155                 160

Leu Asp Lys Gln Ser Asp Thr Gln Tyr Val Cys Lys Arg Thr Leu Val
                165                 170                 175

Asp Arg Gly Trp Gly Asn Gly Cys Gly Leu Phe Gly Lys Gly Ser Leu
            180                 185                 190

Val Thr Cys Ala Lys Phe Ala Cys Ser Lys Lys Met Thr Gly Lys Ser
        195                 200                 205

Ile Gln Pro Glu Asn Leu Glu Tyr Arg Ile Met Leu Ser Val His Gly
    210                 215                 220

Ser Gln His Ser Gly Met Ile Val Asn Asp
225                 230

<210> SEQ ID NO 3
<211> LENGTH: 3423
<212> TYPE: PRT
<213> ORGANISM: Zika virus
```

```
<300> PUBLICATION INFORMATION:
<308> DATABASE ACCESSION NUMBER: GenBank / AMQ48981.1
<309> DATABASE ENTRY DATE: 2016-03-21
<313> RELEVANT RESIDUES IN SEQ ID NO: (1)..(3423)

<400> SEQUENCE: 3

Met Lys Asn Pro Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Gly His Gly Pro Ile Arg Met Val Leu
            35                  40                  45

Ala Ile Leu Ala Phe Leu Arg Phe Thr Ala Ile Lys Pro Ser Leu Gly
50                  55                      60

Leu Ile Asn Arg Trp Gly Ser Val Gly Lys Lys Glu Ala Met Glu Ile
65                  70                      75                  80

Ile Lys Lys Phe Lys Lys Asp Leu Ala Ala Met Leu Arg Ile Ile Asn
                85                  90                  95

Ala Arg Lys Glu Lys Lys Arg Gly Ala Asp Thr Ser Val Gly Ile
                100                 105                 110

Val Gly Leu Leu Leu Thr Thr Ala Met Ala Ala Glu Val Thr Arg Arg
115                 120                     125

Gly Ser Ala Tyr Tyr Met Tyr Leu Asp Arg Asn Asp Ala Gly Glu Ala
130                 135                     140

Ile Ser Phe Pro Thr Thr Leu Gly Met Asn Lys Cys Tyr Ile Gln Ile
145                 150                     155                 160

Met Asp Leu Gly His Met Cys Asp Ala Thr Met Ser Tyr Glu Cys Pro
                165                 170                 175

Met Leu Asp Glu Gly Val Glu Pro Asp Val Asp Cys Trp Cys Asn
                180                 185                 190

Thr Thr Ser Thr Trp Val Val Tyr Gly Thr Cys His His Lys Lys Gly
                195                 200                 205

Glu Ala Arg Arg Ser Arg Arg Ala Val Thr Leu Pro Ser His Ser Thr
                210                 215                 220

Arg Lys Leu Gln Thr Arg Ser Gln Thr Trp Leu Glu Ser Arg Glu Tyr
225                 230                     235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
                260                 265                 270

Ser Gln Lys Val Ile Tyr Leu Val Met Ile Leu Leu Ile Ala Pro Ala
                275                 280                 285

Tyr Ser Ile Arg Cys Ile Gly Val Ser Asn Arg Asp Phe Val Glu Gly
                290                 295                 300

Met Ser Gly Gly Thr Trp Val Asp Val Val Leu Glu His Gly Gly Cys
305                 310                     315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
                340                 345                 350

Ala Ser Ile Ser Asp Met Ala Ser Asp Ser Arg Cys Pro Thr Gln Gly
                355                 360                 365

Glu Ala Tyr Leu Asp Lys Gln Ser Asp Thr Gln Tyr Val Cys Lys Arg
                370                 375                 380
```

```
Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
            405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
            435                 440                 445

Glu Thr Asp Glu Asn Arg Ala Lys Val Glu Ile Thr Pro Asn Ser Pro
    450                 455                 460

Arg Ala Glu Ala Thr Leu Gly Phe Gly Ser Leu Gly Leu Asp Cys
465                 470                 475                 480

Glu Pro Arg Thr Gly Leu Asp Phe Ser Asp Leu Tyr Tyr Leu Thr Met
            485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
            515                 520                 525

Lys Glu Ala Leu Val Glu Phe Lys Asp Ala His Ala Lys Arg Gln Thr
530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
            565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
            595                 600                 605

Ala Glu Thr Leu His Gly Thr Val Thr Val Glu Val Gln Tyr Ala Gly
            610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
            645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
            675                 680                 685

His Trp His Arg Ser Gly Ser Thr Ile Gly Lys Ala Phe Glu Ala Thr
690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
            725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
            755                 760                 765

Thr Lys Asn Gly Ser Ile Ser Leu Met Cys Leu Ala Leu Gly Gly Val
            770                 775                 780

Leu Ile Phe Leu Ser Thr Ala Val Ser Ala Asp Val Gly Cys Ser Val
785                 790                 795                 800

Asp Phe Ser Lys Lys Glu Thr Arg Cys Gly Thr Gly Val Phe Val Tyr
```

-continued

```
                805                 810                 815
Asn Asp Val Glu Ala Trp Arg Asp Arg Tyr Lys Tyr His Pro Asp Ser
            820                 825                 830

Pro Arg Arg Leu Ala Ala Val Lys Gln Ala Trp Glu Asp Gly Ile
            835                 840             845

Cys Gly Ile Ser Ser Val Ser Arg Met Glu Asn Ile Met Trp Arg Ser
            850                 855             860

Val Glu Gly Glu Leu Asn Ala Ile Leu Glu Glu Asn Gly Val Gln Leu
865                 870                 875                 880

Thr Val Val Val Gly Ser Val Lys Asn Pro Met Trp Arg Gly Pro Gln
                885                 890                 895

Arg Leu Pro Val Pro Val Asn Glu Leu Pro His Gly Trp Lys Ala Trp
            900                 905                 910

Gly Lys Ser Tyr Phe Val Arg Ala Ala Lys Thr Asn Asn Ser Phe Val
            915                 920                 925

Val Asp Gly Asp Thr Leu Lys Glu Cys Pro Leu Lys His Arg Ala Trp
930                 935                 940

Asn Ser Phe Leu Val Glu Asp His Gly Phe Gly Val Phe His Thr Ser
945                 950                 955                 960

Val Trp Leu Lys Val Arg Glu Asp Tyr Ser Leu Glu Cys Asp Pro Ala
                965                 970                 975

Val Ile Gly Thr Ala Val Lys Gly Lys Glu Ala Val His Ser Asp Leu
            980                 985                 990

Gly Tyr Trp Ile Glu Ser Glu Lys Asn Asp Thr Trp Arg Leu Lys Arg
            995                 1000                1005

Ala His Leu Ile Glu Met Lys Thr Cys Glu Trp Pro Lys Ser His
        1010                1015            1020

Thr Leu Trp Thr Asp Gly Ile Glu Glu Ser Asp Leu Ile Ile Pro
        1025                1030            1035

Lys Ser Leu Ala Gly Pro Leu Ser His His Asn Thr Arg Glu Gly
        1040                1045            1050

Tyr Arg Thr Gln Met Lys Gly Pro Trp His Ser Glu Glu Leu Glu
        1055                1060            1065

Ile Arg Phe Glu Glu Cys Pro Gly Thr Lys Val His Val Glu Glu
        1070                1075            1080

Thr Cys Gly Thr Arg Gly Pro Ser Leu Arg Ser Thr Thr Ala Ser
        1085                1090            1095

Gly Arg Val Ile Glu Glu Trp Cys Cys Arg Glu Cys Thr Met Pro
        1100                1105            1110

Pro Leu Ser Phe Arg Ala Lys Asp Gly Cys Trp Tyr Gly Met Glu
        1115                1120            1125

Ile Arg Pro Arg Lys Glu Pro Glu Ser Asn Leu Val Arg Ser Met
        1130                1135            1140

Val Thr Ala Gly Ser Thr Asp His Met Asp His Phe Ser Leu Gly
        1145                1150            1155

Val Leu Val Ile Leu Leu Met Val Gln Glu Gly Leu Lys Lys Arg
        1160                1165            1170

Met Thr Thr Lys Ile Ile Ile Ser Thr Ser Met Ala Val Leu Val
        1175                1180            1185

Ala Met Ile Leu Gly Gly Phe Ser Met Ser Asp Leu Ala Lys Leu
        1190                1195            1200

Ala Ile Leu Met Gly Ala Thr Phe Ala Glu Met Asn Thr Gly Gly
        1205                1210            1215
```

```
Asp Val Ala His Leu Ala Leu Ile Ala Ala Phe Lys Val Arg Pro
    1220         1225                 1230

Ala Leu Leu Val Ser Phe Ile Phe Arg Ala Asn Trp Thr Pro Arg
    1235         1240                 1245

Glu Ser Met Leu Leu Ala Leu Ala Ser Cys Leu Leu Gln Thr Ala
    1250         1255                 1260

Ile Ser Ala Leu Glu Gly Asp Leu Met Val Leu Ile Asn Gly Phe
    1265         1270                 1275

Ala Leu Ala Trp Leu Ala Ile Arg Ala Met Val Val Pro Arg Thr
    1280         1285                 1290

Asp Asn Ile Thr Leu Ala Ile Leu Ala Ala Leu Thr Pro Leu Ala
    1295         1300                 1305

Arg Gly Thr Leu Leu Val Ala Trp Arg Ala Gly Leu Ala Thr Cys
    1310         1315                 1320

Gly Gly Phe Met Leu Leu Ser Leu Lys Gly Lys Gly Ser Val Lys
    1325         1330                 1335

Lys Asn Leu Pro Phe Val Met Ala Leu Gly Leu Thr Ala Val Arg
    1340         1345                 1350

Leu Val Asp Pro Ile Asn Val Val Gly Leu Leu Leu Thr Arg
    1355         1360                 1365

Ser Gly Lys Arg Ser Trp Pro Pro Ser Glu Val Leu Thr Ala Val
    1370         1375                 1380

Gly Leu Ile Cys Ala Leu Ala Gly Gly Phe Ala Lys Ala Asp Ile
    1385         1390                 1395

Glu Met Ala Gly Pro Ile Ala Ala Val Gly Leu Leu Ile Val Ser
    1400         1405                 1410

Tyr Val Val Ser Gly Lys Ser Val Asp Met Tyr Ile Glu Arg Ala
    1415         1420                 1425

Gly Asp Ile Thr Trp Glu Lys Asp Ala Glu Val Thr Gly Asn Ser
    1430         1435                 1440

Pro Arg Leu Asp Val Ala Leu Asp Glu Ser Gly Asp Phe Ser Leu
    1445         1450                 1455

Val Glu Asp Asp Gly Pro Pro Met Arg Glu Ile Ile Leu Lys Val
    1460         1465                 1470

Val Leu Met Thr Ile Cys Gly Met Asn Pro Ile Ala Ile Pro Phe
    1475         1480                 1485

Ala Ala Gly Ala Trp Tyr Val Tyr Val Lys Thr Gly Lys Arg Ser
    1490         1495                 1500

Gly Ala Leu Trp Asp Val Pro Ala Pro Lys Glu Val Lys Lys Gly
    1505         1510                 1515

Glu Thr Thr Asp Gly Val Tyr Arg Val Met Thr Arg Arg Leu Leu
    1520         1525                 1530

Gly Ser Thr Gln Val Gly Val Gly Val Met Gln Glu Gly Val Phe
    1535         1540                 1545

His Thr Met Trp His Val Thr Lys Gly Ser Ala Leu Arg Ser Gly
    1550         1555                 1560

Glu Gly Arg Leu Asp Pro Tyr Trp Gly Asp Val Lys Gln Asp Leu
    1565         1570                 1575

Val Ser Tyr Cys Gly Pro Trp Lys Leu Asp Ala Ala Trp Asp Gly
    1580         1585                 1590

His Ser Glu Val Gln Leu Leu Ala Val Pro Pro Gly Glu Arg Ala
    1595         1600                 1605
```

```
Arg Asn Ile Gln Thr Leu Pro Gly Ile Phe Lys Thr Lys Asp Gly
1610                1615                1620

Asp Ile Gly Ala Val Ala Leu Asp Tyr Pro Ala Gly Thr Ser Gly
1625                1630                1635

Ser Pro Ile Leu Asp Lys Cys Gly Arg Val Ile Gly Leu Tyr Gly
1640                1645                1650

Asn Gly Val Val Ile Lys Asn Gly Ser Tyr Val Ser Ala Ile Thr
1655                1660                1665

Gln Gly Arg Arg Glu Glu Glu Thr Pro Val Glu Cys Phe Glu Pro
1670                1675                1680

Ser Met Leu Lys Lys Lys Gln Leu Thr Val Leu Asp Leu His Pro
1685                1690                1695

Gly Ala Gly Lys Thr Arg Arg Val Leu Pro Glu Ile Val Arg Glu
1700                1705                1710

Ala Ile Lys Thr Arg Leu Arg Thr Val Ile Leu Ala Pro Thr Arg
1715                1720                1725

Val Val Ala Ala Glu Met Glu Glu Ala Leu Arg Gly Leu Pro Val
1730                1735                1740

Arg Tyr Met Thr Thr Ala Val Asn Val Thr His Ser Gly Thr Glu
1745                1750                1755

Ile Val Asp Leu Met Cys His Ala Thr Phe Thr Ser Arg Leu Leu
1760                1765                1770

Gln Pro Ile Arg Val Pro Asn Tyr Asn Leu Tyr Ile Met Asp Glu
1775                1780                1785

Ala His Phe Thr Asp Pro Ser Ser Ile Ala Ala Arg Gly Tyr Ile
1790                1795                1800

Ser Thr Arg Val Glu Met Gly Glu Ala Ala Ile Phe Met Thr
1805                1810                1815

Ala Thr Pro Pro Gly Thr Arg Asp Ala Phe Pro Asp Ser Asn Ser
1820                1825                1830

Pro Ile Met Asp Thr Glu Val Glu Val Pro Glu Arg Ala Trp Ser
1835                1840                1845

Ser Gly Phe Asp Trp Val Thr Asp His Ser Gly Lys Thr Val Trp
1850                1855                1860

Phe Val Pro Ser Val Arg Asn Gly Asn Glu Ile Ala Ala Cys Leu
1865                1870                1875

Thr Lys Ala Gly Lys Arg Val Ile Gln Leu Ser Arg Lys Thr Phe
1880                1885                1890

Glu Thr Glu Phe Gln Lys Thr Lys His Gln Glu Trp Asp Phe Val
1895                1900                1905

Val Thr Thr Asp Ile Ser Glu Met Gly Ala Asn Phe Lys Ala Asp
1910                1915                1920

Arg Val Ile Asp Ser Arg Arg Cys Leu Lys Pro Val Ile Leu Asp
1925                1930                1935

Gly Glu Arg Val Ile Leu Ala Gly Pro Met Pro Val Thr His Ala
1940                1945                1950

Ser Ala Ala Gln Arg Arg Gly Arg Ile Gly Arg Asn Pro Asn Lys
1955                1960                1965

Pro Gly Asp Glu Tyr Leu Tyr Gly Gly Gly Cys Ala Glu Thr Asp
1970                1975                1980

Glu Asp His Ala His Trp Leu Glu Ala Arg Met Leu Leu Asp Asn
1985                1990                1995

Ile Tyr Leu Gln Asp Gly Leu Ile Ala Ser Leu Tyr Arg Pro Glu
```

```
                2000                2005                2010
Ala Asp Lys Val Ala Ala Ile Glu Gly Glu Phe Lys Leu Arg Thr
    2015                2020                2025
Glu Gln Arg Lys Thr Phe Val Glu Leu Met Arg Arg Gly Asp Leu
    2030                2035                2040
Pro Val Trp Leu Ala Tyr Gln Val Ala Ser Ala Gly Ile Thr Tyr
    2045                2050                2055
Thr Asp Arg Arg Trp Cys Phe Asp Gly Thr Thr Asn Asn Thr Ile
    2060                2065                2070
Met Glu Asp Ser Val Pro Ala Glu Val Trp Thr Arg His Gly Glu
    2075                2080                2085
Lys Arg Val Leu Lys Pro Arg Trp Met Asp Ala Arg Val Cys Ser
    2090                2095                2100
Asp His Ala Ala Leu Lys Ser Phe Lys Glu Phe Ala Ala Gly Lys
    2105                2110                2115
Arg Gly Ala Ala Phe Gly Val Met Glu Ala Leu Gly Thr Leu Pro
    2120                2125                2130
Gly His Met Thr Glu Arg Phe Gln Glu Ala Ile Asp Asn Leu Ala
    2135                2140                2145
Val Leu Met Arg Ala Glu Thr Gly Ser Arg Pro Tyr Lys Ala Ala
    2150                2155                2160
Ala Ala Gln Leu Pro Glu Thr Leu Glu Thr Ile Met Leu Leu Gly
    2165                2170                2175
Leu Leu Gly Thr Val Ser Leu Gly Ile Phe Phe Val Leu Met Arg
    2180                2185                2190
Asn Lys Gly Ile Gly Lys Met Gly Phe Gly Met Val Thr Leu Gly
    2195                2200                2205
Ala Ser Ala Trp Leu Met Trp Leu Ser Glu Ile Glu Pro Ala Arg
    2210                2215                2220
Ile Ala Cys Val Leu Ile Val Val Phe Leu Leu Leu Val Val Leu
    2225                2230                2235
Ile Pro Glu Pro Glu Lys Gln Arg Ser Pro Gln Asp Asn Gln Met
    2240                2245                2250
Ala Ile Ile Ile Met Val Ala Val Gly Leu Leu Gly Leu Ile Thr
    2255                2260                2265
Ala Asn Glu Leu Gly Trp Leu Glu Arg Thr Lys Ser Asp Leu Ser
    2270                2275                2280
His Leu Met Gly Arg Arg Glu Glu Gly Ala Thr Ile Gly Phe Ser
    2285                2290                2295
Met Asp Ile Asp Leu Arg Pro Ala Ser Ala Trp Ala Ile Tyr Ala
    2300                2305                2310
Ala Leu Thr Thr Phe Ile Thr Pro Ala Val Gln His Ala Val Thr
    2315                2320                2325
Thr Ser Tyr Asn Asn Tyr Ser Leu Met Ala Met Ala Thr Gln Ala
    2330                2335                2340
Gly Val Leu Phe Gly Met Gly Lys Gly Met Pro Phe Tyr Ala Trp
    2345                2350                2355
Asp Phe Gly Val Pro Leu Leu Met Ile Gly Cys Tyr Ser Gln Leu
    2360                2365                2370
Thr Pro Leu Thr Leu Ile Val Ala Ile Ile Leu Leu Val Ala His
    2375                2380                2385
Tyr Met Tyr Leu Ile Pro Gly Leu Gln Ala Ala Ala Ala Arg Ala
    2390                2395                2400
```

```
Ala Gln Lys Arg Thr Ala Ala Gly Ile Met Lys Asn Pro Val Val
    2405                2410                2415

Asp Gly Ile Val Val Thr Asp Ile Asp Thr Met Thr Ile Asp Pro
    2420                2425                2430

Gln Val Glu Lys Lys Met Gly Gln Val Leu Leu Ile Ala Val Ala
    2435                2440                2445

Val Ser Ser Ala Ile Leu Ser Arg Thr Ala Trp Gly Trp Gly Glu
    2450                2455                2460

Ala Gly Ala Leu Ile Thr Ala Ala Thr Ser Thr Leu Trp Glu Gly
    2465                2470                2475

Ser Pro Asn Lys Tyr Trp Asn Ser Ser Thr Ala Thr Ser Leu Cys
    2480                2485                2490

Asn Ile Phe Arg Gly Ser Tyr Leu Ala Gly Ala Ser Leu Ile Tyr
    2495                2500                2505

Thr Val Thr Arg Asn Ala Gly Leu Val Lys Arg Gly Gly Gly
    2510                2515                2520

Thr Gly Glu Thr Leu Gly Glu Lys Trp Lys Ala Arg Leu Asn Gln
    2525                2530                2535

Met Ser Ala Leu Glu Phe Tyr Ser Tyr Lys Lys Ser Gly Ile Thr
    2540                2545                2550

Glu Val Cys Arg Glu Ala Arg Arg Ala Leu Lys Asp Gly Val
    2555                2560                2565

Ala Thr Gly Gly His Ala Val Ser Arg Gly Ser Ala Lys Leu Arg
    2570                2575                2580

Trp Leu Val Glu Arg Gly Tyr Leu Gln Pro Tyr Gly Lys Val Ile
    2585                2590                2595

Asp Leu Gly Cys Gly Arg Gly Gly Trp Ser Tyr Tyr Ala Ala Thr
    2600                2605                2610

Ile Arg Lys Val Gln Glu Val Lys Gly Tyr Thr Lys Gly Gly Pro
    2615                2620                2625

Gly His Glu Glu Pro Val Leu Val Gln Ser Tyr Gly Trp Asn Ile
    2630                2635                2640

Val Arg Leu Lys Ser Gly Val Asp Val Phe His Met Ala Ala Glu
    2645                2650                2655

Pro Cys Asp Thr Leu Leu Cys Asp Ile Gly Glu Ser Ser Ser Ser
    2660                2665                2670

Pro Glu Val Glu Glu Ala Arg Thr Leu Arg Val Leu Ser Met Val
    2675                2680                2685

Gly Asp Trp Leu Glu Lys Arg Pro Gly Ala Phe Cys Ile Lys Val
    2690                2695                2700

Leu Cys Pro Tyr Thr Ser Thr Met Met Glu Thr Leu Glu Arg Leu
    2705                2710                2715

Gln Arg Arg Tyr Gly Gly Gly Leu Val Arg Val Pro Leu Ser Arg
    2720                2725                2730

Asn Ser Thr His Glu Met Tyr Trp Val Ser Gly Ala Lys Ser Asn
    2735                2740                2745

Thr Ile Lys Ser Val Ser Thr Thr Ser Gln Leu Leu Leu Gly Arg
    2750                2755                2760

Met Asp Gly Pro Arg Arg Pro Val Lys Tyr Glu Glu Asp Val Asn
    2765                2770                2775

Leu Gly Ser Gly Thr Arg Ala Val Val Ser Cys Ala Glu Ala Pro
    2780                2785                2790
```

```
Asn Met Lys Ile Ile Gly Asn Arg Ile Glu Arg Ile Arg Ser Glu
    2795                2800                2805

His Ala Glu Thr Trp Phe Phe Asp Glu Asn His Pro Tyr Arg Thr
    2810                2815                2820

Trp Ala Tyr His Gly Ser Tyr Glu Ala Pro Thr Gln Gly Ser Ala
    2825                2830                2835

Ser Ser Leu Ile Asn Gly Val Val Arg Leu Leu Ser Lys Pro Trp
    2840                2845                2850

Asp Val Val Thr Gly Val Thr Gly Ile Ala Met Thr Asp Thr Thr
    2855                2860                2865

Pro Tyr Gly Gln Gln Arg Val Phe Lys Glu Lys Val Asp Thr Arg
    2870                2875                2880

Val Pro Asp Pro Gln Glu Gly Thr Arg Gln Val Met Ser Met Val
    2885                2890                2895

Ser Ser Trp Leu Trp Lys Glu Leu Gly Lys His Lys Arg Pro Arg
    2900                2905                2910

Val Cys Thr Lys Glu Glu Phe Ile Asn Lys Val Arg Ser Asn Ala
    2915                2920                2925

Ala Leu Gly Ala Ile Phe Glu Glu Lys Glu Trp Lys Thr Ala
    2930                2935                2940

Val Glu Ala Val Asn Asp Pro Arg Phe Trp Ala Leu Val Asp Lys
    2945                2950                2955

Glu Arg Glu His His Leu Arg Gly Glu Cys Gln Ser Cys Val Tyr
    2960                2965                2970

Asn Met Met Gly Lys Arg Glu Lys Lys Gln Gly Glu Phe Gly Lys
    2975                2980                2985

Ala Lys Gly Ser Arg Ala Ile Trp Tyr Met Trp Leu Gly Ala Arg
    2990                2995                3000

Phe Leu Glu Phe Glu Ala Leu Gly Phe Leu Asn Glu Asp His Trp
    3005                3010                3015

Met Gly Arg Glu Asn Ser Gly Gly Gly Val Glu Gly Leu Gly Leu
    3020                3025                3030

Gln Arg Leu Gly Tyr Val Leu Glu Glu Met Ser Arg Ile Pro Gly
    3035                3040                3045

Gly Arg Met Tyr Ala Asp Asp Thr Ala Gly Trp Asp Thr Arg Ile
    3050                3055                3060

Ser Arg Phe Asp Leu Glu Asn Glu Ala Leu Ile Thr Asn Gln Met
    3065                3070                3075

Glu Lys Gly His Arg Ala Leu Ala Leu Ala Ile Ile Lys Tyr Thr
    3080                3085                3090

Tyr Gln Asn Lys Val Val Lys Val Leu Arg Pro Ala Glu Lys Gly
    3095                3100                3105

Lys Thr Val Met Asp Ile Ile Ser Arg Gln Asp Gln Arg Gly Ser
    3110                3115                3120

Gly Gln Val Val Thr Tyr Ala Leu Asn Thr Phe Thr Asn Leu Val
    3125                3130                3135

Val Gln Leu Ile Arg Asn Met Glu Ala Glu Glu Val Leu Glu Met
    3140                3145                3150

Gln Asp Leu Trp Leu Leu Arg Arg Ser Glu Lys Val Thr Asn Trp
    3155                3160                3165

Leu Gln Ser Asn Gly Trp Asp Arg Leu Lys Arg Met Ala Val Ser
    3170                3175                3180

Gly Asp Asp Cys Val Val Lys Pro Ile Asp Asp Arg Phe Ala His
```

| | | | | | | | | | | |
|---|---|---|---|---|---|---|---|---|---|---|
| | | 3185 | | | 3190 | | | 3195 | | |

Ala Leu Arg Phe Leu Asn Asp Met Gly Lys Val Arg Lys Asp Thr
    3200                    3205                    3210

Gln Glu Trp Lys Pro Ser Thr Gly Trp Asp Asn Trp Glu Glu Val
    3215                    3220                    3225

Pro Phe Cys Ser His His Phe Asn Lys Leu His Leu Lys Asp Gly
    3230                    3235                    3240

Arg Ser Ile Val Val Pro Cys Arg His Gln Asp Glu Leu Ile Gly
    3245                    3250                    3255

Arg Ala Arg Val Ser Pro Gly Ala Gly Trp Ser Ile Arg Glu Thr
    3260                    3265                    3270

Ala Cys Leu Ala Lys Ser Tyr Ala Gln Met Trp Gln Leu Leu Tyr
    3275                    3280                    3285

Phe His Arg Arg Asp Leu Arg Leu Met Ala Asn Ala Ile Cys Ser
    3290                    3295                    3300

Ser Val Pro Val Asp Trp Val Pro Thr Gly Arg Thr Thr Trp Ser
    3305                    3310                    3315

Ile His Gly Lys Gly Glu Trp Met Thr Thr Glu Asp Met Leu Val
    3320                    3325                    3330

Val Trp Asn Arg Val Trp Ile Glu Glu Asn Asp His Met Glu Asp
    3335                    3340                    3345

Lys Thr Pro Val Thr Lys Trp Thr Asp Ile Pro Tyr Leu Gly Lys
    3350                    3355                    3360

Arg Glu Asp Leu Trp Cys Gly Ser Leu Ile Gly His Arg Pro Arg
    3365                    3370                    3375

Thr Thr Trp Ala Glu Asn Ile Lys Asn Thr Val Asn Met Val Arg
    3380                    3385                    3390

Arg Ile Ile Gly Asp Glu Glu Lys Tyr Met Asp Tyr Leu Ser Thr
    3395                    3400                    3405

Gln Val Arg Tyr Leu Gly Glu Glu Gly Ser Thr Pro Gly Val Leu
    3410                    3415                    3420

<210> SEQ ID NO 4
<211> LENGTH: 10795
<212> TYPE: DNA
<213> ORGANISM: Zika virus
<300> PUBLICATION INFORMATION:
<308> DATABASE ACCESSION NUMBER: GenBank / KU926309.1
<309> DATABASE ENTRY DATE: 2016-03-21
<313> RELEVANT RESIDUES IN SEQ ID NO: (1)..(10795)

<400> SEQUENCE: 4

```
gatctgtgtg aatcagactg cgacagttcg agtttgaagc gaaagctagc aacagtatca     60
acaggtttta ttttggattt ggaaacgaga gtttctggtc atgaaaaacc caaaaaagaa    120
atccggagga ttccggattg tcaatatgct aaaacgcgga gtagcccgtg tgagcccctt    180
tgggggcttg aagaggctgc cagccggact tctgctgggt catgggccca tcaggatggt    240
cttggcgatt ctagcctttt tgagattcac ggcaatcaag ccatcactgg gtctcatcaa    300
tagatggggt tcagtgggga aaaaagaggc tatggaaata ataaagaagt tcaagaaaga    360
tctggctgcc atgctgagaa taatcaatgc taggaaggag aagaagagac gaggcgcaga    420
tactagtgtc ggaattgttg gcctcctgct gaccacagct atggcagcgg aggtcactag    480
acgtgggagt gcatactaca tgtacttgga cagaaacgat gctggggagg ccatatcttt    540
tccaaccaca ttggggatga ataagtgtta tatacagatc atggatcttg gacacatgtg    600
```

```
tgatgccacc atgagctatg aatgccctat gctggatgag ggggtggaac cagatgacgt    660
cgattgttgg tgcaacacga cgtcaacttg ggttgtgtac ggaacctgcc atcacaaaaa    720
aggtgaagca cggagatcta aagagctgt gacgctcccc tcccattcca ctaggaagct    780
gcaaacgcgg tcgcaaacct ggttggaatc gagagaatac acaaagcact tgattagagt    840
cgaaaattgg atattcagga accctggctt cgcgttagca gcagctgcca tcgcttggct    900
tttgggaagc tcaacgagcc aaaaagtcat atacttggtc atgatactgc tgattgcccc    960
ggcatacagc atcaggtgca taggagtcag caatagggac tttgtggaag gtatgtcagg   1020
tgggacttgg gttgatgttg tcttggaaca tggaggttgt gtcaccgtaa tggcacagga   1080
taaaccgact gtcgacatag agctggttac aacaacagtc agcaacatgg cggaggtaag   1140
atcctactgc tatgaggcat caatatcaga catggcttcg gacagccgct gcccaacaca   1200
aggtgaagcc taccttgaca agcaatcaga cactcaatat gtctgcaaaa gaacgttagt   1260
ggacagaggc tggggaaatg gatgtggact ttttggcaaa gggagcctgg tgacatgcgc   1320
taagtttgca tgctccaaga aaatgaccgg gaagagcatc cagccagaga atctggagta   1380
ccggataatg ctgtcagttc atggctccca gcacagtggg atgatcgtta atgacacagg   1440
acatgaaact gatgagaata gagcgaaggt tgagataacg cccaattcac caagagccga   1500 agccacccctg gggggttttg gaagcctagg acttgattgt gaaccgagga caggccttga   1560
cttttcagat ttgtattact tgactatgaa taacaagcac tggttggttc acaaggagtg   1620
gttccacgac attccattgc cttggcacgc tggggcagac accggaactc cacactggaa   1680
caacaaagaa gcactggtag agttcaagga cgcacatgcc aaaaggcaaa ctgtcgtggt   1740
tctagggagt caagaaggag cagttcacac ggcccttgct ggagctctgg aggctgagat   1800
ggatggtgca aagggaaggc tgtcctctgg ccacttgaaa tgtcgcctga aaatggataa   1860
acttagattg aagggcgtgt catactcctt gtgtaccgca gcgttcacat tcaccaagat   1920
cccggctgaa acactgcacg ggacagtcac agtggaggta cagtacgcag ggacagatgg   1980
accttgcaag gttccagctc agatggcggt ggacatgcaa actctgaccc cagttgggag   2040
gttgataacc gctaaccccg taatcactga aagcactgag aactctaaga tgatgctgga   2100
acttgatcca ccatttgggg actcttacat tgtcataggg gtcgggggaga agaagatcac   2160 ccaccactgg cacaggagtg gcagcaccat tggaaaagca tttgaagcca ctgtgagagg   2220
tgccaagaga atggcagtct tgggagacac agcctgggac tttggatcag ttggaggcgc   2280
tctcaactca tttgggcaagg gcatccatca aatttttgga gcagctttca aatcattgtt   2340
tggaggaatg tcctggttct cacaaattct cattggaacg ttgctgatgt ggttgggcct   2400
gaacacaaag aatggatcta tttcccttat gtgcttggcc ttaggggggag tgttgatctt   2460 cttatccaca gccgtctctg ctgatgtggg gtgctcggtg gacttctcaa agaaggagac   2520
gagatgcggt acagggtgt tcgtctataa cgacgttgaa gcctgagggg acaggtacaa   2580
gtaccatcct gactcccccc gtagattggc agcagcagtc aagcaagcct gggaagatgg   2640
tatctgcggg atctcctctg tttcaagaat ggaaaacatc atgtggagat cagtagaagg   2700
ggagctcaac gcaatcctgg aagagaatgg agttcaactg acggtcgttg tgggatcggt   2760
aaaaaacccc atgtggagag gtccacagag attgcccgtg cctgtgaacg agctgcccca   2820
cggctggaag gcttgggggga aatcgtactg cgtcagagca gcaaagacaa ataacagctt   2880
tgtcgtggat ggtgacacac tgaaggaatg cccactcaaa catagagcat ggaacagctt   2940
tcttgtggag gatcatgggt tcggggtatt tcacactagt gtctggctca aggttagaga   3000
```

```
agattattca ttagagtgtg atccagccgt tattggaaca gctgttaagg gaaaggaggc   3060
tgtacacagt gatctaggct actggattga gagtgagaag aatgacacat ggaggctgaa   3120
gagggcccat ctgatcgaga tgaaaacatg tgaatggcca aagtcccaca cattgtggac   3180
agatggaata aagagagtg atctgatcat acccaagtct ttagctgggc cactcagcca   3240
tcacaatacc agagagggct acaggaccca aatgaaaggg ccatggcaca gtgaagagct   3300
tgaaattcgg tttgaggaat gcccaggcac taaggtccac gtggaggaaa catgtggaac   3360
aagaggacca tctctgagat caaccactgc aagcggaagg gtgatcgagg aatggtgctg   3420
cagggagtgc acaatgcccc cactgtcgtt ccgggctaaa gatggctgtt ggtatggaat   3480
ggagataagg cccaggaaag aaccagaaag caacttagta aggtcaatgg tgactgcagg   3540
atcaactgat cacatggatc acttctccct tggagtgctt gtgattctgc tcatggtgca   3600
ggaagggctg aagaagagaa tgaccacaaa gatcatcata agcacatcaa tggcagtgct   3660
ggtagctatg atcctgggag attttcaat gagtgacctg gctaagcttg caattttgat   3720
gggtgccacc ttcgcggaaa tgaacactgg aggagatgta gctcatctgg cgctgatagc   3780
ggcattcaaa gtcagaccag cgttgctggt atctttcatc ttcagagcta attggacacc   3840
ccgtgaaagc atgctgctgg ccttggcctc gtgtcttttg caaactgcga tctccgcctt   3900
ggaaggcgac ctgatggttc tcatcaatgg ttttgctttg gcctggttgg caatacgagc   3960
gatggttgtt ccacgcactg ataacatcac cttggcaatc ctggctgctc tgacaccact   4020
ggcccggggc acactgcttg tggcgtggag agcaggcctt gctacttgcg gggggtttat   4080
gctcctctct ctgaagggaa aaggcagtgt gaagaagaac ttaccatttg tcatggccct   4140
gggactaacc gctgtgaggc tggtcgaccc catcaacgtg gtgggactgc tgttgctcac   4200
aaggagtggg aagcggagct ggccccctag cgaagtactc acagctgttg gcctgatatg   4260
cgcattggct ggagggttcg ccaaggcaga tatagagatg gctgggccca tagccgcgt   4320 cggtctgcta attgtcagtt acgtggtctc aggaaagagt gtggacatgt acattgaaag   4380
agcaggtgac atcacatggg aaaaagatgc ggaagtcact ggaaacagtc cccggctcga   4440
tgtggcgcta gatgagagtg gtgatttctc cctggtggag gatgacggtc cccccatgag   4500
agagatcata ctcaaggtgg tcctgatgac catctgtggc atgaacccaa tagccatacc   4560
ttttgcagct ggagcgtggt acgtatacgt gaagactgga aaaaggagtg gtgctctatg   4620
ggatgtgcct gctcccaagg aagtaaaaaa gggggagacc acagatggag tgtacagagt   4680
aatgactcgt agactgctgg gttcaacaca agttggagtg ggagttatgc aagagggggt   4740
ctttcacact atgtggcacg tcacaaaagg atccgcactg agaagcggtg aagggagact   4800
tgatccatac tggggagatg tcaagcagga tctggtgtca tactgtgtc catggaagct   4860 agatgccgcc tgggacgggc acagcgaggt gcagctcttg gccgtgcccc ccggagagag   4920
agcgaggaac atccagactc tgcccggaat atttaagaca aaggatgggg acattggagc   4980
ggttgcgctg gattacccag caggaacttc aggatctcca atcctagaca gtgtgggag   5040 agtgatagga ctttatggca atggggtcgt gatcaaaaat gggagttatg ttagtgccat   5100
cacccaaggg aggagggagg aagagactcc tgttgagtgc ttcgagcctt cgatgctgaa   5160
gaagaagcag ctaactgtct tagacttgca tcctggagct gggaaaacca ggagagttct   5220
tcctgaaata gtccgtgaag ccataaaaac aagactccgt actgtgatct tagctccaac   5280
cagggttgtc gctgctgaaa tggaggaggc ccttagaggg cttccagtgc gttatatgac   5340
```

```
aacagcagtc aatgtcaccc actctggaac agaaatcgtc gacttaatgt gccatgccac    5400
cttcacttca cgtctactac agccaatcag agtccccaac tataatctgt atattatgga    5460
tgaggcccac ttcacagatc cctcaagtat agcagcaaga ggatacattt caacaagggt    5520
tgagatgggc gaggcggctg ccatcttcat gaccgccacg ccaccaggaa cccgtgacgc    5580
atttccggac tccaactcac caattatgga caccgaagtg gaagtcccag agagagcctg    5640
gagctcaggc tttgattggg tgacggatca ttctggaaaa acagtttggt ttgttccaag    5700
cgtgaggaac ggcaatgaga tcgcagcttg tctgacaaag gctggaaaac gggtcataca    5760
gctcagcaga aagacttttg agacagagtt ccagaaaaca aaacatcaag agtgggactt    5820
tgtcgtgaca actgacattt cagagatggg cgccaacttt aaagctgacc gtgtcataga    5880
ttccaggaga tgcctaaagc cggtcatact tgatggcgag agagtcattc tggctggacc    5940
catgcctgtc acacatgcca gcgctgccca gaggaggggg cgcataggca ggaatcccaa    6000
caaacctgga gatgagtatc tgtatggagg tgggtgcgca gagactgacg aagaccatgc    6060
acactggctt gaagcaagaa tgctccttga caatatttac ctccaagatg gcctcatagc    6120
ctcgctctat cgacctgagg ccgacaaagt agcagccatt gagggagagt tcaagcttag    6180
gacggagcaa aggaagacct ttgtggaact catgagaaga ggagatcttc ctgtttggct    6240
ggcctatcag gttgcatctg ccggaataac ctacacagat agaagatggc gctttgatgg    6300
cacgaccaac aacaccataa tggaagacag tgtgccggca gaggtgtgga ccagacacgg    6360
agagaaaaga gtgctcaaac cgaggtggat ggacgccaga gtttgttcag atcatgcggc    6420
cctgaagtca ttcaaggagt ttgccgctgg gaaaagagga gcggcttttg gagtgatgga    6480
agccctggga acactgccag gacacatgac agagagattc caggaagcca ttgacaacct    6540
cgctgtgctc atgcgggcag agactggaag caggccttac aaagccgcgg cggcccaatt    6600
gccggagacc ctagagacca ttatgctttt ggggttgttg gaacagtct cgctgggaat    6660 ctttttcgtc ttgatgagga acaagggcat agggaagatg ggcctttgaa tggtgactct    6720
tggggccagc gcatggctca tgtggctctc ggaaattgag ccagccagaa ttgcatgtgt    6780
cctcattgtt gtgttcctat tgctggtggt gctcatacct gagccagaaa agcaaagatc    6840 tcccccaggac aaccaaatgg caatcatcat catggtagca gtaggtcttc tgggcttgat    6900
taccgccaat gaactcggat ggttggagag aacaaagagt gacctaagcc atctaatggg    6960
aaggagagag gaggggggcaa ccataggatt ctcaatggac attgacctgc ggccagcctc    7020
agcttgggcc atctatgctg ccttgacaac tttcattacc ccagccgtcc aacatgcagt    7080
gaccacttca tacaacaact actccttaat ggcgatggcc acgcaagctg gagtgttgtt    7140
tggtatgggc aaagggatgc cattctacgc atgggactt ggagtcccgc tgctaatgat    7200
aggttgctac tcacaattaa cacccctgac cctaatagtg gccatcattt tgctcgtggc    7260
gcactacatg tacttgatcc cagggctgca ggcagcagct gcgcgtgctg cccagaagag    7320
aacggcagct ggcatcatga agaaccctgt tgtggatgga atagtggtga ctgacattga    7380
cacaatgaca attgaccccc aagtggagaa aaagatggga caggtgctac tcatagcagt    7440
agccgtctcc agcgccatac tgtcgcggac cgcctggggg tgggggagg ctggggccct    7500 gatcacagcc gcaacttcca cttt gtggga aggctctccg aacaagtact ggaactcctc    7560
tacagccact tcactgtgta acatttttag gggaagttac ttggctggag cttctctaat    7620
ctacacagta acaagaaacg ctggcttggt caagagacgt gggggtggaa caggagagac    7680
cctgggagag aaatggaagg cccgcttgaa ccagatgtcg gccctggagt tctactccta    7740
```

```
caaaaagtca ggcatcaccg aggtgtgcag agaagaggcc cgccgcgccc tcaaggacgg    7800
tgtggcaacg ggaggccatg ctgtgtcccg aggaagtgca agctgagat ggttggtgga     7860 gcggggatac ctgcagccct acggaaaggt cattgatctt ggatgtggca gagggggctg    7920
gagttactac gccgccacca tccgcaaagt tcaagaagtg aaaggataca caaaaggagg    7980
ccctggtcat gaagaacccg tgttggtgca agctatggg tggaacatag tccgtcttaa     8040 gagtgggtg gacgtctttc atatggcggc tgagccgtgt gacacgttgc tgtgtgacat     8100
aggtgagtca tcatctagtc ctgaagtgga agaagcacgg acgctcagag tcctctccat    8160
ggtgggggat tggcttgaaa aaagaccagg agccttttgt ataaaagtgt tgtgcccata    8220
caccagcact atgatggaaa ccctggagcg actgcagcgt aggtatgggg aggactggt    8280 cagagtgcca ctctcccgca actctacaca tgagatgtac tgggtctctg gagcgaaaag    8340
caacaccata aaaagtgtgt ccaccacgag ccagctcctc ttggggcgca tggacgggcc    8400
taggaggcca gtgaaatatg aggaggatgt gaatctcggc tctggcacgc gggctgtggt    8460
aagctgcgct gaagctccca acatgaagat cattggtaac cgcattgaaa ggatccgcag    8520
tgagcacgcg gaaacgtggt tctttgacga gaaccaccca taggacat gggcttacca     8580 tggaagctat gaggcccca cacaagggtc agcgtcctct ctaataaacg gggttgtcag     8640
gctcctgtca aaaccctggg atgtggtgac tggagtcaca ggaatagcca tgaccgacac    8700 cacccgtat ggtcagcaaa gagttttcaa ggaaaaagtg gacactaggg tgccagaccc     8760
ccaagaaggc actcgtcagg ttatgagcat ggtctcttcc tggttgtgga aagagctagg    8820
caaacacaaa cggccacgag tctgtaccaa agaagagttc atcaacaagg ttcgcagcaa    8880
tgcagcatta ggggcaatat ttgaagagga aaaagagtgg aagactgcag tggaagctgt    8940
gaacgatcca aggttctggg ctctagtgga caaggaaaga gagcaccacc tgagaggaga    9000
gtgccagagt tgtgtgtaca acatgatggg aaaaagagaa aagaaacaag gggaatttgg    9060
aaaggccaag ggcagccgcg ccatctggta tatgtggcta ggggctagat ttctagagtt    9120
cgaagccctt ggattcttga acgaggatca ctggatgggg agagagaact caggaggtgg    9180
tgttgaaggg ctgggattac aaagactcgg atatgtccta aagagatga gtcgcatacc    9240 aggaggaagg atgtatgcag atgacactgc tggctgggac acccgcatca gcaggtttga    9300
tctggagaat aagctctaa tcaccaacca aatggagaaa gggcacaggg ccttggcatt    9360
ggccataatc aagtacacat accaaaacaa agtggtaaag gtccttagac cagctgaaaa    9420
agggaaaaca gttatggaca ttatttcgag acaagaccaa aggggggagcg acaagttgt    9480 cacttacgct cttaacacat ttaccaacct agtggtgcaa ctcattcgga atatggaggc    9540
tgaggaagtt ctagagatgc aagacttgtg gctgctgcgg aggtcagaga agtgaccaa    9600 ctggttgcag agcaacggat gggataggct caaacgaatg gcagtcagtg agatgattg    9660 cgttgtgaag ccaattgatg acaggtttgc acatgccctc aggttcttga atgatatggg    9720
aaaagttagg aaggacacac aagagtggaa accctcaact ggatgggaca actgggaaga    9780
agttccgttt tgctcccacc acttcaacaa gctccatctc aaggacggga ggtccattgt    9840
ggttccctgc cgccaccaag atgaactgat tggccgggcc cgcgtctctc agggcggg    9900 atggagcatc cgggagactg cttgcctagc aaaatcatat gcgcaaatgt ggcagctcct    9960
ttatttccat agaagggacc tccgactgat ggccaatgcc atttgttcat ctgtgccagt    10020
tgactgggtt ccaactggga gaactacctg gtcaatccat ggaaagggag aatggatgac    10080
```

-continued

```
cactgaagac atgcttgtgg tgtggaacag agtgtggatt gaggagaacg accacatgga    10140
agacaagacc ccagttacga aatggacaga cattccctat ttgggaaaaa gggaagactt    10200
gtggtgtgga tctctcatag ggcacagacc gcgcaccacc tgggctgaga acattaaaaa    10260
cacagtcaac atggtgcgca ggatcatagg tgatgaagaa aagtacatgg actacctatc    10320
cacccaagtt cgctacttgg gtgaagaagg gtctacacct ggagtgctgt aagcaccaat    10380
cttaatgttg tcaggcctgc tagtcagcca cagcttgggg aaagctgtgc agcctgtgac    10440
ccccccagga gaagctggga aaccaagcct atagtcaggc cgagaacgcc atggcacgga    10500
agaagccatg ctgcctgtga gcccctcaga ggacactgag tcaaaaaacc ccacgcgctt    10560
ggaggcgcag gatgggaaaa gaaggtggcg accttcccca cccttcaatc tggggcctga    10620
actggagatc agctgtggat ctccagaaga gggactagtg gttagaggag accccccgga    10680
aaacgcaaaa cagcatattg acgctgggaa agaccagaga ctccatgagt ttccaccacg    10740
ctggccgcca ggcacagatc gccgaatagc ggcggccggt gtggggaaat ccatg         10795
```

<210> SEQ ID NO 5
<211> LENGTH: 168
<212> TYPE: PRT
<213> ORGANISM: Artificial Sequence
<220> FEATURE:
<223> OTHER INFORMATION: Synthetic peptide
<300> PUBLICATION INFORMATION:
<308> DATABASE ACCESSION NUMBER: GenBank / KU926309.1
<309> DATABASE ENTRY DATE: 2016-03-21
<313> RELEVANT RESIDUES IN SEQ ID NO: (1)..(168)

<400> SEQUENCE: 5

Ala Glu Val Thr Arg Arg Gly Ser Ala Tyr Tyr Met Tyr Leu Asp Arg
 1               5                  10                  15

Asn Asp Ala Gly Glu Ala Ile Ser Phe Pro Thr Thr Leu Gly Met Asn
            20                  25                  30

Lys Cys Tyr Ile Gln Ile Met Asp Leu Gly His Met Cys Asp Ala Thr
        35                  40                  45

Met Ser Tyr Glu Cys Pro Met Leu Asp Glu Gly Val Glu Pro Asp Asp
    50                  55                  60

Val Asp Cys Trp Cys Asn Thr Thr Ser Thr Trp Val Val Tyr Gly Thr
65                  70                  75                  80

Cys His His Lys Lys Gly Glu Ala Arg Arg Ser Arg Arg Ala Val Thr
                85                  90                  95

Leu Pro Ser His Ser Thr Arg Lys Leu Gln Thr Arg Ser Gln Thr Trp
            100                 105                 110

Leu Glu Ser Arg Glu Tyr Thr Lys His Leu Ile Arg Val Glu Asn Trp
        115                 120                 125

Ile Phe Arg Asn Pro Gly Phe Ala Leu Ala Ala Ala Ile Ala Trp
    130                 135                 140

Leu Leu Gly Ser Ser Thr Ser Gln Lys Val Ile Tyr Leu Val Met Ile
145                 150                 155                 160

Leu Leu Ile Ala Pro Ala Tyr Ser
                165

<210> SEQ ID NO 6
<211> LENGTH: 75
<212> TYPE: PRT
<213> ORGANISM: Artificial Sequence
<220> FEATURE:
<223> OTHER INFORMATION: Synthetic peptide
<300> PUBLICATION INFORMATION:

<308> DATABASE ACCESSION NUMBER: GenBank / KU926309.1
<309> DATABASE ENTRY DATE: 2016-03-21
<313> RELEVANT RESIDUES IN SEQ ID NO: (94)..(168)

<400> SEQUENCE: 6

```
Ala Val Thr Leu Pro Ser His Ser Thr Arg Lys Leu Gln Thr Arg Ser
1               5                   10                  15

Gln Thr Trp Leu Glu Ser Arg Glu Tyr Thr Lys His Leu Ile Arg Val
            20                  25                  30

Glu Asn Trp Ile Phe Arg Asn Pro Gly Phe Ala Leu Ala Ala Ala
        35                  40                  45

Ile Ala Trp Leu Leu Gly Ser Ser Thr Ser Gln Lys Val Ile Tyr Leu
    50                  55                  60

Val Met Ile Leu Leu Ile Ala Pro Ala Tyr Ser
65                  70                  75
```

<210> SEQ ID NO 7
<211> LENGTH: 504
<212> TYPE: PRT
<213> ORGANISM: Artificial Sequence
<220> FEATURE:
<223> OTHER INFORMATION: Synthetic peptide
<300> PUBLICATION INFORMATION:
<308> DATABASE ACCESSION NUMBER: GenBank / KU926309.1
<309> DATABASE ENTRY DATE: 2016-03-21
<313> RELEVANT RESIDUES IN SEQ ID NO: (169)..(672)

<400> SEQUENCE: 7

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240
```

```
Ala Leu Val Glu Phe Lys Asp Ala His Ala Lys Arg Gln Thr Val Val
            245                 250                 255

Val Leu Gly Ser Gln Glu Gly Ala Val His Thr Ala Leu Ala Gly Ala
        260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 8
<211> LENGTH: 18
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C1

<400> SEQUENCE: 8

Trp Pro His Thr Gln Gly Pro Gly Cys Cys Gly Pro Gly Ser Trp Pro
1               5                   10                  15

Gly Gln

<210> SEQ ID NO 9
<211> LENGTH: 18
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
```

<223> OTHER INFORMATION: C2

<400> SEQUENCE: 9

Trp Pro His Thr Gln Gly Pro Gly Cys Cys Gly Pro Gly Leu Arg Gly
1               5                   10                  15

His Ala

<210> SEQ ID NO 10
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C3

<400> SEQUENCE: 10

Trp Pro Trp Ile Gly Thr Gly Pro Gly Cys Cys Gly Pro Gly Lys Arg
1               5                   10                  15

Asn Ala Thr Pro
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C4

<400> SEQUENCE: 11

Trp Pro Trp Ile Gly Thr Gly Pro Gly Cys Cys Gly Pro Gly Lys Thr
1               5                   10                  15

Asp Ala Tyr Ser
            20

<210> SEQ ID NO 12
<211> LENGTH: 18
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C5

<400> SEQUENCE: 12

Ala Gly Arg Arg Pro Gly Pro Gly Cys Cys Gly Pro Gly Ser Trp Pro
1               5                   10                  15

Gly Gln

<210> SEQ ID NO 13
<211> LENGTH: 18
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C6

<400> SEQUENCE: 13

Ala Gly Arg Arg Pro Gly Pro Gly Cys Cys Gly Pro Gly Leu Arg Gly

```
1               5                  10                  15

His Ala

<210> SEQ ID NO 14
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C7

<400> SEQUENCE: 14

Met Asp Ser Pro Ile Lys Gly Pro Gly Cys Cys Gly Pro Gly Lys Arg
1               5                  10                  15

Asn Ala Thr Pro
            20

<210> SEQ ID NO 15
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C8

<400> SEQUENCE: 15

Met Asp Ser Pro Ile Lys Gly Pro Gly Cys Cys Gly Pro Gly Lys Thr
1               5                  10                  15

Asp Ala Tyr Ser
            20

<210> SEQ ID NO 16
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C1 Binds to Active Site 2

<400> SEQUENCE: 16

Trp Pro His Thr Gln
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C2 Binds to Active Site 2
<220> FEATURE:
<221> NAME/KEY: MISC_FEATURE
<223> OTHER INFORMATION: optionally includes an amino acid at the
      N-terminus, C-terminus or between two amino acids of the sequence

<400> SEQUENCE: 17

Trp Pro His Thr Gln
1               5
```

-continued

```
<210> SEQ ID NO 18
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C3 Binds to Active Site 2

<400> SEQUENCE: 18

Trp Pro Trp Ile Gly Thr
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C4 Binds to Active Site 2
<220> FEATURE:
<221> NAME/KEY: MISC_FEATURE
<223> OTHER INFORMATION: optionally includes an amino acid at the
      N-terminus, C-terminus or between two amino acids of the sequence

<400> SEQUENCE: 19

Trp Pro Trp Ile Gly Thr
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C5 Binds to Active Site 2

<400> SEQUENCE: 20

Ala Gly Arg Arg Pro
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C6 Binds to Active Site 2
<220> FEATURE:
<221> NAME/KEY: MISC_FEATURE
<223> OTHER INFORMATION: optionally includes an amino acid at the
      N-terminus, C-terminus or between two amino acids of the sequence

<400> SEQUENCE: 21

Ala Gly Arg Arg Pro
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: MISC_FEATURE
<223> OTHER INFORMATION: C7 Binds to Active Site 2

<400> SEQUENCE: 22

Met Asp Ser Pro Ile Lys
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C8 Binds to Active Site 2

<400> SEQUENCE: 23

Met Asp Ser Pro Ile Lys
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C1 Binds to Active Site 1

<400> SEQUENCE: 24

Ser Trp Pro Gly Gln
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C2 Binds to Active Site 1

<400> SEQUENCE: 25

Leu Arg Gly His Ala
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C3 Binds to Active Site 1

<400> SEQUENCE: 26

Lys Arg Asn Ala Thr Pro
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic Peptide
```

```
<220> FEATURE:
<221> NAME/KEY: MISC_FEATURE
<223> OTHER INFORMATION: C4 Binds to Active Site 1

<400> SEQUENCE: 27

Lys Thr Asp Ala Tyr Ser
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C5 Binds to Active Site 1
<220> FEATURE:
<221> NAME/KEY: MISC_FEATURE
<223> OTHER INFORMATION: optionally includes an amino acid at the
      N-terminus, C-terminus or between two amino acids of the sequence

<400> SEQUENCE: 28

Ser Trp Pro Gly Gln
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C6 Binds to Active Site 1
<220> FEATURE:
<221> NAME/KEY: MISC_FEATURE
<223> OTHER INFORMATION: optionally includes an amino acid at the
      N-terminus, C-terminus or between two amino acids of the sequence

<400> SEQUENCE: 29

Leu Arg Gly His Ala
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C7 Binds to Active Site 1
<220> FEATURE:
<221> NAME/KEY: MISC_FEATURE
<223> OTHER INFORMATION: optionally includes an amino acid at the
      N-terminus, C-terminus or between two amino acids of the sequence

<400> SEQUENCE: 30

Lys Arg Asn Ala Thr Pro
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C8 Binds to Active Site 1
```

```
<220> FEATURE:
<221> NAME/KEY: MISC_FEATURE
<223> OTHER INFORMATION: optionally includes an amino acid at the
      N-terminus, C-terminus or between two amino acids of the sequence

<400> SEQUENCE: 31

Lys Thr Asp Ala Tyr Ser
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: Bridge peptide

<400> SEQUENCE: 32

Gly Pro Gly Cys Cys Gly Pro Gly
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: P1

<400> SEQUENCE: 33

Cys Ser Trp Pro Gly Gln
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: P2

<400> SEQUENCE: 34

Cys Leu Arg Gly His Ala
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: X1

<400> SEQUENCE: 35

Cys Lys Arg Asn Ala Thr Pro
1               5

<210> SEQ ID NO 36
<211> LENGTH: 7
<212> TYPE: PRT
<213> ORGANISM: Artificial Sequence
```

```
<220> FEATURE:
<223> OTHER INFORMATION: Synthetic Peptide
<220> FEATURE:
<221> NAME/KEY: MISC_FEATURE
<223> OTHER INFORMATION: X2

<400> SEQUENCE: 36

Cys Lys Thr Asp Ala Tyr Ser
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 37

Ser Met Ala Gly Gly
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 38

Trp Pro Phe Phe Pro
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 39

Gly Pro Asn Ala Thr Pro
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 40

Trp Pro Trp Phe Gly Pro
1               5
```

ZIKA VIRUS ASSAY SYSTEMS

CROSS-REFERENCE TO RELATED APPLICATIONS

This application is a continuation-in-part of U.S. application Ser. No. 16/345,943, which is the U.S. national stage of International Application No. PCT/US17/59129, filed Oct. 30, 2017, which claims priority to U.S. Provisional Patent Application No. 62/414,674, filed on Oct. 29, 2016. The contents of each application are incorporated herein by reference.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 69,632 byte ACII (Text) file named "51017C_SeqListing.txt"; created on Jun. 12, 2019.

BACKGROUND

Zika virus (ZIKV) was isolated from a sentinel Indian rhesus macaque in the Zika forest of Uganda in 1947, although the first manuscript describing the virus was not published until 1952[3-5]. The initial descriptions of spontaneous and experimentally-induced human disease followed shortly thereafter[6,7]. This virus belongs to the genus flavivirus and is related to Dengue virus (DENV), yellow fever virus (YFV), Japanese encephalitis virus (JEV), and west Nile virus (WNV)[5]. Different species of mosquitoes of the Aedes genus are vectors for ZIKV[8,9]. The potential for the virus to infect the central nervous tissue of mammals was first described in 1971[10]. However, ZIKV remained a relatively minor and obscure cause of human disease for most of the second half of the 20<sup>th</sup> century and was featured in a very limited number of scientific reports. In fact, it was not until 2007 that autochthonous human infection was described outside Africa and continental Asia—in the Federated States of Micronesia[11-13]. At that time, the virus caused a mild and self-limited disease characterized by rash, conjunctivitis, and arthralgia and was thus easily confused with DENV or chikungunya virus (CHIKV)[11,12]. The potential existed for the virus to continue migrating eastward and eventually reach the Americas as a mosquito-borne disease[12]. A major change in the epidemiology and clinical manifestations of the virus took place during an outbreak in French Polynesia in late 2013-early 2014 with the first reports of perinatal transmission and association with Guillain-Barre syndrome[14-17]. This outbreak was complicated by concurrent outbreaks of DENV and CHIKV transmitted by the same Aedes vector and presenting with similar manifestations and, in some instances, simultaneous infection with ZIKV and DENV in the same patient[18,19]. By this time, it was also becoming apparent that ZIKV can persist in body fluids such as urine, saliva, and semen beyond the short time (<7 days) that it is present in blood[20-23]. In fact, the first report of possible sexual transmission of ZIKV was published in 2011: a scientist who had become infected in Senegal in 2008 transmitted the virus to his wife upon his return to Colorado[24]. The first instances of mosquito-borne transmission in the Americas came from Easter Island, Chile in 2014 and were closely followed by a report of ZIKV infection of eight Brazilian patients in early 2015[25,26]. Since then, other reports from Brazil have chronicled a rapidly spreading epidemic that, once more, co-exists with transmission of DENV and CHIKV, and is characterized by fever, conjunctivitis, and a maculopapular rash[27-31]. The epidemic has spread north with mosquito-borne transmission being reported as far north as Mexico with many nations in the Americas reporting such cases[32-34]. In early 2016, the first cases were reported on American territory in Puerto Rico[35]. More ominously, there are reports of microcephaly and ocular damage in aborted fetuses from and infants born to mothers infected with ZIKV with the virus recovered from amniotic fluid, and placental and brain tissue[2,36-43]. ZIKV infection has been declared a global public health emergency by the World Health Organization[44,45] In the United States, the CDC has issued guidance for the management of the infection in the general population, pregnant women, and possibly affected infants as well as for the prevention of sexual transmission in view of new reports of a possible such occurrence[46-51] More recently, ZIKV transmission has been described in Miami[52], suggesting that any region of the United States with Aedes could result in autochthonous spread.

In view of the foregoing, there is a need for rapid diagnostic assays for detecting ZIKV infection in humans. Such assays will allow women to make informed decisions about pregnancy and can assist in preventing sexual transmission of the virus. Rapid diagnostics for both the acute phase and convalescent phase will allow for prevention or control of ZIKV spread. It is particularly important to distinguish ZIKV infection from that of the structurally related dengue virus (DENV) in areas where DENV is endemic and ZIKV is increasing in prevalence. Regions with the highest incidence of ZIKV infection also tend to be resource-limited, so there is an urgent and unmet need for rapid, simple, and cost-effective diagnostics that can specifically identify ZIKV and ZIKV-specific antibody (Ab) responses in body fluids.

SUMMARY

The present disclosure provides binding constructs, e.g., antibodies or antigen binding fragments thereof or antibody mimetics, that bind to a ZIKV (e.g., a ZIKV protein). In exemplary aspects, the binding construct is specific for the ZIKV and does not bind to a DENV (e.g., a DENV protein). In exemplary aspects, the binding constructs bind to ZIKV and do not bind to any other flavivirus, including, for example, DENV, YFV, JEV, and WNV. In exemplary aspects, the binding constructs bind to ZIKV and do not bind to the Togaviridae chikungunya virus (CHIKV). In exemplary aspects, the binding construct described herein binds to a ZIKV protein (a protein expressed by ZIKV). In exemplary aspects, the binding construct described herein binds to an epitope within SEQ ID NO: 1 or SEQ ID NO: 2. In exemplary aspects, the ZIKV protein is membrane glycoprotein precursor M (SEQ ID NO: 5), or the mature form thereof (membrane glycoprotein M, SEQ ID NO: 6), or envelope protein E (SEQ ID NO: 7). In exemplary aspects, the binding construct binds to the ZIKV envelope protein E, which is described in Dai et al., Cell Host & Microbe 19(5): 696-704 (2016). In exemplary aspects, the binding construct comprises the structure $A_1$-B-$A_2$ wherein $A_1$ is a first peptide arm that binds to a first binding site of a target protein, $A_2$ is a second peptide arm that binds to a second binding site of the target protein, and B is a bridge peptide which links $A_1$ to $A_2$. Optionally, the bridge peptide is about 5 to about 10 amino acids in length. In various aspects, (a) $A_1$ comprises an amino acid sequence of any one of SEQ ID NOs:

24-31, (b) $A_2$ comprises an amino acid sequence of any one of SEQ ID NOs: 16-23, or (c) a combination thereof. In various instances, $A_1$ comprises an amino acid sequence of SEQ ID NO: 26 and $A_2$ comprises an amino acid sequence of SEQ ID NO: 18. In exemplary aspects, $A_1$ comprises an amino acid sequence of SEQ ID NO: 25 and $A_2$ comprises an amino acid sequence of SEQ ID NO: 21. In exemplary instances, $A_1$ comprises an amino acid sequence of SEQ ID NO: 26 and $A_2$ comprises an amino acid sequence of SEQ ID NO: 23. Optionally, the bridge peptide comprises the amino acid sequence of SEQ ID NO: 32. In exemplary aspects, the binding construct comprises an amino acid sequence of SEQ ID NO: 10, 13, or 14.

The present disclosure provides a polypeptide comprising an amino acid sequence of any one of SEQ ID NOs: 15. Optionally, the polypeptide comprises at least one of SEQ ID NOs: 16-23 or at least one of SEQ ID NOs: 24-31, or the polypeptide comprises a first peptide comprising a sequence of any one of SEQ ID NOs: 16-23 and a second peptide comprising a sequence of any one of SEQ ID NOs: 24-31. In various aspects, when the polypeptide comprises a first peptide and a second peptide, the polypeptide further comprises a bridge peptide that links the first peptide to the second peptide. In exemplary instances, the bridge peptide comprises the sequence of SEQ ID NO: 32

Related nucleic acids encoding the polypeptides or binding constructs of the present disclosure and expression vectors comprising the nucleic acids are also provided herein. Host cells comprising the nucleic acid or the expression vector are further provided herein.

Kits comprising the binding constructs of the present disclosure are provided herein. In exemplary aspects, the kit comprises the binding construct and a solid support. Optionally, the kit comprises a capture molecule which binds to ZIKV.

Assay systems are further provided herein. In exemplary aspects, the assay system comprises a porous matrix comprising at least three zones, Zone A, Zone B, and Zone C, wherein Zone A comprises a binding construct as described herein, wherein the binding construct is not bound to a ZIKV, Zone B comprises a binding construct as described herein, wherein the binding construct is bound to a ZIKV, and Zone C comprises a secondary antibody which binds the binding construct of Zone A and Zone B.

Without being bound to any particular theory, the binding constructs of the present disclosure are particularly useful in diagnostic assays. Thus, the present disclosure provides diagnostic assays wherein one or more of the binding constructs is used. The diagnostic assays of the present disclosure in exemplary aspects detect both ZIKV and serological reactivity against ZIKV. Advantageously, the diagnostic assays provided herein are rapid, easy to use, and simple. Results in exemplary aspects are visualized by the eye in less than 1 hour and need minimal operator expertise. In exemplary aspects, no instrumentation is needed and labor time is reduced. The diagnostic assays of the present disclosure are in exemplary aspects stable and easily transported and have a long shelf life. Accordingly, the diagnostic assays are cost-effective and economical. The total cost of the reagents and materials for an exemplary embodiment of a diagnostic assay for the detection of either ZIKV virus or serological responses to ZIKV is about $2 per test. Advantageously, the diagnostic assay in exemplary aspects is used as a point-of-care (POC) assay.

The present disclosure accordingly provides a method of detecting a ZIKV infection in a subject. In exemplary aspects, the method comprises (i) contacting a sample obtained from the subject with a binding construct, or polypeptide described herein, thereby forming a test mixture, and (ii) assaying the test mixture for a complex comprising ZIKV bound to the binding construct, or polypeptide, wherein, when the complex is present in the test mixture, the subject is determined as having a ZIKV infection.

The present disclosure also provides a method of detecting ZIKV immunity in a subject. In exemplary aspects, the method comprises (i) adding a blood, plasma, or serum sample obtained from the subject to a solid support bound to a capture molecule that binds to ZIKV, (ii) adding a binding construct, or polypeptide described herein, (iii) adding a detection agent which binds to the binding construct or polypeptide, and (iv) assaying for a signal from the detection agent, wherein, when the signal is detected, the subject is determined as not having ZIKV immunity and, when the signal is not detected, the subject is determined as having ZIKV immunity.

The present disclosure additionally provides a method of detecting a ZIKV infection and ZIKV immunity in a subject. In exemplary aspects, the method comprises adding a sample obtained from a subject to the assay system as described herein, wherein, when the assay system exhibits a single band in Zone C, the subject is determined as having neither a ZIKV infection nor ZIKV immunity, when the assay system exhibits a band in each of Zone A and Zone B, the subject is determined as having both a ZIKV infection and ZIKV immunity, and when the assay system exhibits a band in Zone B and a band is absent in Zone A, the subject is determined as not having a ZIKV infection but having ZIKV immunity.

The present disclosure further provides a method of assessing efficacy of a Zika virus (ZIKV) vaccine in a subject who has received a ZIKV vaccine. In exemplary aspects, the method comprises adding a sample obtained from the subject to the assay system as described herein, wherein, when the assay system exhibits (i) a band in each of Zone A and Zone B or (ii) a band in Zone B and a band is absent in Zone A, the ZIKV vaccine is determined as effective in the subject, and when the assay system exhibits a single band in Zone C, the ZIKV vaccine is determined as ineffective in the subject. In exemplary aspects, the method comprises (i) adding a blood, plasma, or serum sample obtained from the subject to a solid support bound to a capture molecule that binds to ZIKV, (ii) adding a binding construct, or polypeptide described herein, (iii) adding a detection agent which binds to the binding construct or polypeptide, and (iv) assaying for a signal from the detection agent, wherein, when the signal is detected, the vaccine is determined as ineffective in the subject, and, when the signal is not detected, the vaccine is determined as effective in the subject.

The present disclosure additionally provides a method of treating or preventing a ZIKV infection in a subject. In exemplary aspects, the method comprises administering to the subject a pharmaceutical composition as described herein in an amount effective to treat or prevent the ZIKV injection in the subject. The present disclosure additionally provides a method of inducing an immune response against a ZIKV in a subject. In exemplary aspects, the method comprises administering to the subject a pharmaceutical composition as described herein in an amount effective to induce an immune response against a ZIKV in a subject.

BRIEF DESCRIPTION OF THE DRAWINGS

FIG. 7 represents a scheme for a microtiter-based ZIKV immunoassay using the antibody mimetics of the present disclosure. In this iteration, Concanavalin A is the capture molecule. Detection antibody is an antibody mimetic of the present disclosure, e.g., a clamp peptide.

FIG. 9A is an illustration of the principle behind the lateral flow assay for the detection of active ZIKV infection.

FIG. 9B is an illustration of the principle behind the lateral flow assay for the detection of prior exposure to ZIKV. GNP is gold nanoparticle.

DETAILED DESCRIPTION

Figure 1B:
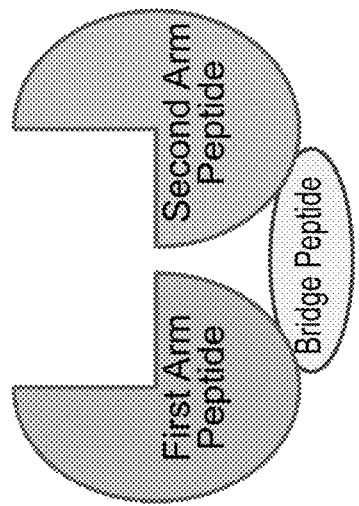
FIG. 1B is a schematic representation of the clamp peptide structure made by two peptide arms of five or six amino acids in length linked by a bridge peptide.

Binding Constructs
Binding Targets and Epitopes

Provided herein are binding constructs (e.g., an antibody or antigen-binding fragment thereof or antibody mimetic) which specifically recognize a Zika virus (ZIKV) with minimal or no cross-reactivity to a Dengue virus (DENV). In exemplary instances, the binding constructs do not bind to any DENV subtype, including, e.g., DENV subtype 1, DENV subtype 2, DENV subtype 3, and DENV subtype 4. In exemplary aspects, the binding constructs bind to ZIKV and do not bind to any other flavivirus. In exemplary aspects, the binding constructs bind to ZIKV even in the presence of other flaviviruses, e.g., DENV, West Nile virus, Yellow fever virus, and the like.

In exemplary embodiments, the binding constructs bind to a ZIKV protein and do not bind to a DENV protein. In exemplary aspects, the binding construct does not bind to a protein of any one of DENV subtype 1, DENV subtype 2, DENV subtype 3, and DENV subtype 4. In exemplary aspects, the binding constructs bind to a protein of a ZIKV comprising the genome of GenBank Accession No. KU926309.1 (SEQ ID NO: 4) or other ZIKV isolates, including, but not limited to the ZIKV comprising a gene or genome of any one of GenBank Accession Nos. KU820897, KU922923, KU820898, KU853012, KU820899, KU744693, KU497555, KU707826, KU527068, KU365777, KU365778, KU365779, KU365780, KU312312, KU321639, AB908162, KU509998, KJ776791, KU681081, KU681082, and EU545988. In exemplary aspects, the ZIKV protein to which the binding constructs bind comprises a fragment of the sequence of SEQ ID NO: 3 or 4. In exemplary aspects, the ZIKV protein to which the binding constructs bind comprises a fragment of SEQ ID NO: 1 or SEQ ID NO: 2. In exemplary aspects, the binding constructs bind to a membrane glycoprotein precursor M (SEQ ID NO: 5), or the mature form thereof (membrane glycoprotein M, SEQ ID NO: 6), or envelope protein E (SEQ ID NO: 7). In exemplary aspects, the binding constructs bind to the ZIKV protein in a sample comprising blood, plasma, serum, urine, or saliva.

In exemplary aspects, the binding constructs bind to a ZIKV molecule which is other than a ZIKV protein. In exemplary aspects, the binding constructs bind to a sugar or lipid from ZIKV or a molecule that is induced by ZIKV infection.

For purposes herein, the phrase "binds to ZIKV", or a similar phrase, means that the binding construct (e.g., antibody, or antigen-binding fragment) binds to an epitope of a ZIKV protein or ZIKV antigen, and the phrase "do not bind to any DENV subtype" or like phrase, means that the binding construct (e.g., antibody, or antigen-binding fragment) does not bind to an epitope of a DENV protein or DENV antigen. In exemplary aspects, the binding construct has an equilibrium association constant, KA, for ZIKV which is at least $10^5$ mol$^{-1}$, at least $10^6$ mol$^{-1}$, at least $10^7$ mol$^{-1}$, at least $10^8$ mol$^{-1}$, at least $10^9$ mol$^{-1}$, or at least $10^{10}$ mol$^{-1}$. In exemplary aspects, the binding construct has an equilibrium association constant, KA, for DENV which is less than 10$^3$ mol$^{-1}$. In exemplary aspects, the KD of the binding constructs provided herein for ZIKV is about 1.0× 10$^{-6}$ or less, about 1.0×10$^{-7}$ or less, about 1.0×10$^{-8}$ or less, about 1.0×10$^{-9}$ or less, about 1.0×10$^{-10}$ or less. In exemplary aspects, the KD of the binding constructs provided herein for DENV is greater than or about 1.0×10$^{-3}$. In exemplary aspects, the binding construct does not bind to a DENV protein or DENV antigen at a concentration below 10 μg/ml.

By "epitope" as used herein is meant the region of or within a ZIKV antigen which is bound by the binding construct of the present disclosure. In some embodiments, the epitope is a linear epitope. By "linear epitope" as used herein refers to the region of or within the ZIKV protein which is bound by the binding construct and which region is composed of contiguous amino acids of the amino acid sequence of the ZIKV protein. The amino acids of a linear epitope are adjacent to each other in the primary structure of the ZIKV protein. Accordingly, a linear epitope is a fragment or portion of the amino acid sequence of the antigen, i.e., a ZIKV protein. In other exemplary embodiments, the epitope is a conformational or structural epitope. By "conformational epitope" or "structural epitope" is meant an epitope which is composed of amino acids which are located in close proximity to one another when the ZIKV protein is in its properly folded state. Unlike linear epitopes, the amino acids of a conformational or structural epitope need not be adjacent to each other in the primary structure (i.e., amino acid sequence) of the ZIKV protein. A conformational or structural epitope is not necessarily made of contiguous amino acids of the amino acid sequence of the antigen.

In exemplary aspects, the binding constructs of the present disclosure bind to an immunodominant epitope of ZIKV. As used herein, the term "immunodominant epitope" refers to an epitope of a ZIKV antigen on which the immune response focuses through a process called immunodominance. Immunodominant focus determines which epitopes are favored to vary antigenically to escape immune pressure. Immunodominance within hosts is described in Chapter 6 of Frank S A, *Immunology and Evolution of Infectious Disease*, Princeton University Press, Princeton, N.J., 2002. In exemplary aspects, the binding constructs of the present disclosure bind to an immunodominant epitope which is exclusive to ZIKV, thereby allowing for discrimination between a ZIKV infection and a DENV infection in a subject. In exemplary aspects, the binding constructs of the present disclosure bind to a ZIKV immunodominant epitope, such that sera from ZIKV infected patients block the interaction between the binding construct and the epitope. Suitable assays for testing whether the binding of an antibody is to an immunodominant epitope are known in the art.

In exemplary aspects, the binding constructs of the present disclosure bind to an epitope within the amino acid sequence of SEQ ID NO: 1, SEQ ID NO: 2, SEQ ID NO: 3, or SEQ ID NO: 4. In exemplary aspects, the binding constructs of the present disclosure binds to an epitope within the amino acid sequence of a membrane glycoprotein precursor M (SEQ ID NO: 5), or the mature form thereof (membrane glycoprotein M, SEQ ID NO: 6), or envelope protein E (SEQ ID NO: 7). The binding constructs of the present disclosure, however, are not limited to only such binding constructs. Other binding constructs which bind to ZIKV with minimal or no cross-reactivity to a Dengue virus (DENV) are provided herein.

Affinity and Avidity

The binding constructs provided herein bind to ZIKV in a non-covalent and reversible manner. In exemplary embodiments, the binding strength of the binding construct to ZIKV may be described in terms of its affinity, a measure of the strength of interaction between the binding site of the binding construct and the epitope. In exemplary aspects, the binding constructs provided herein have high-affinity for ZIKV and thus will bind a greater amount of ZIKV in a shorter period of time than low-affinity binding constructs. In exemplary aspects, the binding construct has an equilibrium association constant, KA, which is at least 10$^5$ mol$^{-1}$, at least 10$^6$ mol$^{-1}$, at least 10$^7$ mol$^{-1}$, at least 10$^8$ mol$^{-1}$, at least 10$^9$ mol$^{-1}$, or at least 10$^{10}$ mol$^{-1}$. In exemplary aspects, the binding constructs provided herein exhibit high affinity for ZIKV in human blood, serum, plasma, saliva or urine. In exemplary aspects, the binding construct binds to the ZIKV and does not bind to a DENV in a sample comprising human blood, serum, plasma, saliva or urine. In exemplary aspects, the binding construct binds to the ZIKV even when a substantial amount of DENV or another flavivirus is present in the sample.

In exemplary embodiments, the binding strength of the binding construct to ZIKV may be described in terms of its sensitivity. KD is the equilibrium dissociation constant, a ratio of $k_{off}/k_{on}$, between the binding construct and ZIKV. KD and KA are inversely related. The KD value relates to the concentration of the binding construct (the amount of binding construct needed for a particular experiment), and so the lower the KD value (lower concentration), the higher the affinity of the binding construct. In exemplary aspects, the binding strength of the binding construct to ZIKV may be described in terms of KD. In exemplary aspects, the KD of the binding constructs provided herein for ZIKV is about 1.0×10$^{-6}$ or less, about 1.0×10$^{-7}$ or less, about 1.0×10$^{-8}$ or less, about 1.0×10$^{-9}$ or less, about 1.0×10$^{-10}$ or less. In exemplary aspects, the KD of the binding constructs provided herein is micromolar, nanomolar, picomolar or femtomolar. In exemplary aspects, the KD of the binding constructs provided herein is within a range of about 10$^{-4}$ to 10$^{-6}$ or 10$^{-7}$ to 10$^{-9}$ or 10$^{-10}$ to 10$^{-12}$ or 10$^{-13}$ to 10$^{-15}$.

Avidity gives a measure of the overall strength of an antibody-antigen complex. It is dependent on three major parameters: affinity of the binding construct for the epitope, valency of both the binding construct and ZIKV, and structural arrangement of the parts that interact. The greater a binding construct's valency (number of antigen binding sites), the greater the amount of antigen (ZIKV) it can bind. In exemplary aspects, the binding constructs have a strong avidity for ZIKV. In exemplary aspects, the binding constructs are bivalent. In exemplary aspects, the binding constructs are multivalent.

Neutralization

In exemplary embodiments, the binding constructs of the present disclosure are neutralizing binding constructs. For example, the binding construct in some aspects is a neutralizing antibody. As used herein, the term "neutralizing binding construct" or "neutralizing antibody" refers to a binding construct or antibody which has the ability to prevent viral entry by binding to regions on the virus involved in the entry process. In exemplary aspects, the binding construct of the present disclosure prevents viral entry at a concentration below about 10 μg per ml. In exemplary aspects, the neutralizing binding construct, e.g., neutralizing antibody, is a broadly neutralizing antibody which recognizes a wide variety of viral glycoproteins on the surface of enveloped viruses or the protein shell of nonenveloped viruses. Neutralizing antibodies and broadly neutralizing antibodies are known in the art. See, e.g., Sankaranarayanan et al., "Broadly Neutralizing Antibodies for therapy of viral Infections" *Antibody Tech Journal* 6: 1-15 (2016).

Structure

The binding constructs described herein may be engineered to have one of a multitude of structures. In exemplary aspects, the binding constructs provided herein have a structure of an antibody or antigen-binding fragment thereof. In exemplary aspects, the binding constructs provided herein have a structure based on or derived from an antibody. In exemplary aspects, the binding constructs provided herein have a structure of a synthetic antibody mimic, an engineered protein, or an aptamer, such as those described herein and in McEnaney et al., "Chemically Synthesized Molecules with the Targeting and Effector Functions of Antibodies" J. Am. Chem. Soc., 136 (52): 18034-18043 (2014); Binz and Plückthun, "Engineered proteins as specific binding reagents" Curr Opin Biotechnol. 16(4):459-69 (2005); and Roque et al., "Antibodies and genetically engineered related molecules: production and purification" Biotechnol Prog. 20(3):639-54 (2004).

Antibodies and Antigen-Binding Fragments

In exemplary embodiments, the binding construct is an antibody. The antibody may be any type of antibody, i.e., immunoglobulin, known in the art. In exemplary embodiments, the antibody is an antibody of class or isotype IgA, IgD, IgE, IgG, or IgM. In exemplary embodiments, the antibody described herein comprises one or more alpha, delta, epsilon, gamma, and/or mu heavy chains. In exemplary embodiments, the antibody described herein comprises zero, one, or more kappa or light chains. In exemplary aspects, the antibody is an IgG antibody and optionally is one of the four human subclasses: IgG1, IgG2, IgG3 and IgG4. Also, the antibody in some embodiments is a monoclonal antibody. In other embodiments, the antibody is a polyclonal antibody.

In some embodiments, the antibody is structurally similar to or derived from a naturally-occurring antibody, e.g., an antibody isolated and/or purified from a mammal, e.g., mouse, rabbit, goat, horse, chicken, hamster, camel, llama, human, and the like. In this regard, the antibody may be considered as a mammalian antibody, e.g., a mouse antibody, rabbit antibody, goat antibody, horse antibody, chicken antibody, hamster antibody, human antibody, and the like. In exemplary aspects, the antibody comprises sequence of only mammalian antibodies. Methods of producing such antibodies are known in the art, some of which are described further herein under the section entitled "*Methods of Antibody Production.*" In exemplary aspects, the binding construct is a fully human antibody, or does not comprise sequences of non-human antibodies.

In some embodiments, the antibody is a genetically-engineered antibody and does not occur in nature. In exemplary embodiments, the antibody is a single chain antibody, a single domain antibody, a humanized antibody, a chimeric antibody, a CDR-grafted antibody, a humaneered antibody, a bispecific antibody, a trispecific antibody, and the like. Genetic engineering techniques also provide the ability to make fully human antibodies from a non-human source. In some aspects, the genetically-engineered antibody is a single chain antibody (SCA) specific for ZIKV. Methods of making SCAs are known in the art. See, for example, Davis et al., *Nature Biotechnology* 9: 165-169 (1991).

In some aspects, the antibody is a chimeric antibody. The term "chimeric antibody" is used herein to refer to an antibody-containing constant domains from one species and the variable domains from a second, or more generally, containing stretches of amino acid sequence from at least two species. In particular aspects, the chimeric antibody binds to ZIKV.

In some aspects, the antibody is a humanized antibody. The term "humanized" when used in relation to antibodies refers to antibodies having at least CDR regions from a non-human source which are engineered to have a structure and immunological function more similar to true human antibodies than the original source antibodies. For example, humanizing can involve grafting CDR from a non-human antibody, such as a mouse antibody, into a human antibody. Humanizing also can involve select amino acid substitutions to make a non-human sequence look more like a human sequence.

Use of the terms "chimeric or humanized" herein is not meant to be mutually exclusive, and rather, is meant to encompass chimeric antibodies, humanized antibodies, and chimeric antibodies that have been further humanized. Except where context otherwise indicates, statements about (properties of, uses of, testing of, and so on) chimeric antibodies apply to humanized antibodies, and statements about humanized antibodies pertain also to chimeric antibodies. Likewise, except where context dictates, such statements also should be understood to be applicable to antibodies and antigen-binding fragments of such antibodies.

In some aspects, the antibody is a Humaneered™ antibody. Humaneering technology is a proprietary method of KaloBios Pharmaceuticals, Inc. (South San Francisco, Calif.) for converting non-human antibodies into engineered human antibodies. Humaneered™ antibodies have high affinity, and highly similar to human germline antibody sequences. See, e.g., Tomasevic et al., *Growth Factors* 32: 223-235 (2014).

In exemplary aspects, the antibody is a CDR-grafted antibody specific for ZIKV. Methods of making CDR-grafted antibodies are known in the art. See, for example, Lo, Benny, *Antibody Engineering: Methods and Protocols*, Volume 248 (2004), which is incorporated by reference in its entirety. In exemplary embodiments, the antibody is engineered to be bispecific, trispecific, or multi-specific, and the antibody comprises two or more distinct antigen-binding regions. In some aspects, the antibody is a bispecific or trispecific antibody specific for ZIKV. Methods of making bispecific or trispecific antibodies are known in the art. See, for example, Marvin and Zhu, *Acta Pharmacologica Sinica* 26: 649-658 (2005) and U.S. Pat. No. 6,551,592. In exemplary aspects, the binding construct is a bi-specific antigen-binding construct specific for a first epitope of ZIKV and a second epitope of ZIKV. In exemplary embodiments, the antibody is quadroma, heterodimeric bispecific antibody, bispecific antibody fusion, bispecific antibody fragment, a bispecific T-cell engager (BiTE), or a multi-specific antibody. In exemplary embodiments, the antibody is engineered to be bivalent, trivalent, or multivalent. See, e.g., Cuesta et al., "Multivalent antibodies: when design surpasses evolution" Trends in Biotechnology 28, 355-362 (2010); Holliger et al., "Engineered antibody fragments and the rise of single domains" Nat. Biotechnol. 23, 1126-1136 (2005); Chan et al., "Therapeutic antibodies for autoimmunity and inflammation" Nat Rev Immunol 10, 301-316 (2010); Byrne et al., "A tale of two specificities: bispecific antibodies for therapeutic and diagnostic applications" Trends Biotechnol. 31, 621-632 (2013). In exemplary embodiments, the antibody is in monomeric form, while in other embodiments, the antibody is conjugated to one or more antibodies (e.g., each of which recognize the same epitope of the first antibody). Accordingly, in some aspects, the antibody is in dimeric, polymeric, oligomeric, or multimeric form.

In exemplary aspects, the binding construct is an antigen-binding fragment of an antibody or comprises an antigen-binding fragment of an antibody. The antigen-binding fragment (also referred to herein as "antigen-binding portion") may be an antigen-binding fragment of any of the antibodies described herein. The antigen-binding fragment can be any part of an antibody that has at least one antigen binding site, including, but not limited to, Fab, F(ab')$_2$, a monospecific or bispecific Fab$_2$, a trispecific Fab$_3$, a monovalent IgG, scFv, dsFv, scFv-Fc, bispecific diabodies, trispecific triabodies, minibodies, or a fragment of IgNAR (e.g., V-NAR), or a fragment of hcIgG (e.g., VhH), or bis-scFvs, fragments expressed by a Fab expression library, and the like. In exemplary aspects, the antigen-binding fragment is a domain antibody, VhH domain, V-NAR domain, VH domain, VL domain, or the like. Antibody fragments of the disclosure, however, are not limited to these exemplary types of antibody fragments. In exemplary aspects, the binding construct comprises a Fab fragment. In exemplary aspects, the binding construct comprises two Fab fragments. In exemplary aspects, the binding construct comprises two Fab fragments connected via a linker. In exemplary aspects, the binding construct comprises or is a minibody comprising two Fab fragments. In exemplary aspects, the binding construct comprises or is a minibody comprising two Fab fragments joined via a linker. Minibodies are known in the art. See, e.g., Hu et al., Cancer Res 56: 3055-3061 (1996). In exemplary aspects, the binding construct comprises or is a minibody comprising two Fab fragments joined via a linker, optionally, comprising an alkaline phosphatase domain.

A domain antibody comprises a functional binding unit of an antibody, and can correspond to the variable regions of either the heavy (V$_H$) or light (V$_L$) chains of antibodies. A domain antibody can have a molecular weight of approximately 13 kDa, or approximately one-tenth of a full antibody. Domain antibodies may be derived from full antibodies such as those described herein.

Antibody fragments that contain the antigen-binding, or idiotype, of the antibody molecule may be generated by techniques known in the art. For example, such fragments include, but are not limited to, the F(ab')$_2$ fragment which may be produced by pepsin digestion of the antibody molecule; the Fab' fragments which may be generated by reducing the disulfide bridges of the F(ab')$_2$ fragment; and the two Fab' fragments which may be generated by treating the antibody molecule with papain and a reducing agent.

A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., Protein Engineering, 7, 697-704 (1994)).

Recombinant antibody fragments, e.g., scFvs, can also be engineered to assemble into stable multimeric oligomers of high binding avidity and specificity to different target antigens. Such diabodies (dimers), triabodies (trimers) or tetrabodies (tetramers) are well known in the art, see e.g., Kortt et al., Biomol Eng. 2001 18:95-108, (2001) and Todorovska et al., J Immunol Methods. 248:47-66, (2001).

Bispecific antibodies (bscAb) are molecules comprising two single-chain Fv fragments joined via a glycine-serine linker using recombinant methods. The V light-chain (V$_L$) and V heavy-chain (V$_H$) domains of two antibodies of interest in exemplary embodiments are isolated using standard PCR methods. The V$_L$ and V$_H$ cDNA's obtained from each hybridoma are then joined to form a single-chain fragment in a two-step fusion PCR. Bispecific fusion proteins are prepared in a similar manner. Bispecific single-chain antibodies and bispecific fusion proteins are antibody substances included within the scope of the present disclosure. Exemplary bispecific antibodies are taught in U.S. Patent Application Publication No. 2005-0282233A1 and International Patent Application Publication No. WO 2005/087812, both applications of which are incorporated herein by reference in their entirety.

In exemplary embodiments, the binding construct is a biparatopic antibody, or a biparatopic antigen-binding fragment thereof, having the capability of binding two different non-overlapping epitopes on the same target antigen molecule. By simultaneously binding to the same cell surface targets, biparatopic antibodies and biparatopic antigen-binding fragments thereof may result in enhanced binding avidity, leading to preferential (strong) binding to only cells that express the targets, thus fine-tuning the antibody selectivity. It has been demonstrated that biparatopic antibodies or biparatopic antigen-binding fragments thereof, by simultaneously binding to two different epitopes on the same target molecule, could even potentially acquire new functionality that could not be achieved with the parent antibodies (or antigen-binding fragments) when used alone or in combination. In exemplary aspects, the binding constructs provided herein are biparatopic for ZIKV.

In exemplary embodiments, the antigen-binding fragment is engineered to be bispecific, trispecific, or multi-specific. In exemplary aspects, the antigen-binding fragment comprises two or more distinct antigen-binding regions. In some aspects, the antigen-binding fragment is a bispecific or trispecific antibody specific for ZIKV and at least one other antigen. In exemplary aspects, the binding construct is a bi-specific antigen-binding fragment specific for a first epitope of ZIKV and a second epitope of ZIKV. In exemplary embodiments, the antigen-binding fragment is engineered to be bivalent, trivalent, or multivalent. In exemplary embodiments, the binding construct is a bivalent Fab fragment monospecific for ZIKV. In some embodiments, the antigen-binding fragment is in monomeric form, while in other embodiments, the antigen-binding fragment is conjugated to one or more antigen-binding fragments (e.g., each of which recognize the same epitope of the first antigen-binding fragment). Accordingly, in some aspects, the antigen-binding fragment is dimerized, polymerized, oligomerized, or multimerized. In exemplary aspects, the binding construct is a dimerized Fab fragment.

Antibody Mimetics

In exemplary aspects, the binding construct is an antibody mimetic. Antibody mimetics have been successfully used in the development of binding assays for the detection of analytes in biological samples, as well as in separation methods, cancer therapy, targeted drug delivery, and in vivo imaging. The recent advances in the field of antibody mimetics and their applications in bioanalytical chemistry, specifically in diagnostics and other analytical methods have been described (Yu et al., Annual Review of Analytical Chemistry 10, 293-320 (2017). Because synthetic peptides are more resistant to physicochemical stress, characteristically more reproducible, and, ultimately, less expensive to manufacture and commercialize, when compared to antibodies, their use as elements of antibody mimetics capable of binding to ligand analytes in a manner analogous to that of the antigen-antibody interaction has spurred increased interest in the biotechnology and bioanalytical communities. To produce antibody mimetics that outperform antibodies with regard to binding affinities, cellular and tumor penetration, large-scale production, and temperature and pH stability is a high priority goal of the industry (Yu et al., 2017, supra).

In exemplary aspects, the antibody mimetic is an aptamer. Recent advances in the field of combinatorial sciences have identified short polymer sequences (e.g., oligonucleic acid or peptide molecules) with high affinity and specificity to a given target. For example, SELEX technology has been used to identify DNA and RNA aptamers with binding properties that rival mammalian antibodies, the field of immunology has generated and isolated antibodies or antibody fragments which bind to a myriad of compounds and phage display has been utilized to discover new peptide sequences with very favorable binding properties. Based on the success of these molecular evolution techniques, it is certain that molecules can be created which bind to any target molecule. A loop structure is often involved with providing the desired binding attributes as in the case of: aptamers which often utilize hairpin loops created from short regions without complimentary base pairing, naturally derived antibodies that utilize combinatorial arrangement of looped hyper-variable regions and new phage display libraries utilizing cyclic peptides that have shown improved results when compared to linear peptide phage display results. Thus, sufficient evidence has been generated to suggest that high affinity ligands can be created and identified by combinatorial molecular evolution techniques. For the invention, molecular evolution techniques can be used to isolate compounds specific for ZIKV described herein. For more on aptamers, see, generally, Gold, L., Singer, B., He, Y. Y., Brody. E., "Aptamers As Therapeutic And Diagnostic Agents," J. Biotechnol. 74:5-13 (2000). Relevant techniques for generating aptamers may be found in U.S. Pat. No. 6,699,843, which is incorporated by reference in its entirety.

In exemplary aspects, the binding construct (e.g., the antibody mimetic) is a clamp peptide. Clamp peptides, as further described herein, represent a new class of antibody mimetics. In exemplary aspects, the clamp peptide comprises the structure $A_1$-B-$A_2$ wherein $A_1$ is a first peptide arm that binds to a first binding site of a target protein, $A_2$ is a second peptide arm that binds to a second binding site of the target protein, and B is a bridge peptide which links $A_1$ to $A_2$. In exemplary aspects, each of $A_1$ and $A_2$ is a peptide of about 5 to about 7 amino acids, e.g., about 5 amino acids, about 6 amino acids, or about 7 amino acids. In exemplary aspects, the bridge peptide (B) is about 5 to about 10 amino acids in length (e.g., about 5 amino acids, about 6 amino acids, about 7 amino acids, about 8 amino acids, about 9 amino acids, or about 10 amino acids in length. In various aspects, the amino acids of the clamp peptide, or the first peptide arm, the second peptide arm, or the bridge peptide thereof, are naturally-occurring or coded or non-naturally occurring or non-coded. Non-naturally occurring amino acids refer to amino acids that do not naturally occur in vivo but which, nevertheless, can be incorporated into the peptide structures described herein. "Non-coded" as used herein refer to an amino acid that is not an L-isomer of any of the following 20 amino acids: Ala, Cys, Asp, Glu, Phe, Gly, His, lie, Lys, Leu, Met, Asn, Pro, Gin, Arg, Ser, Thr, Val, Trp, Tyr. Naturally-occurring or coded amino acids include the L-isomers of the amino acids: Ala, Cys, Asp, Glu, Phe, Gly, His, lie, Lys, Leu, Met, Asn, Pro, Gin, Arg, Ser, Thr, Val, Trp, Tyr. Exemplary non-naturally occurring or non-coded amino acids include, any D or L isomers of the non-naturally occurring or non-coded amino acids selected from the group consisting of: beta-alanine, N-alpha-methyl-alanine (Me-Ala), aminobutyric acid (Abu), gamma-aminobutyric acid, aminohexanoic acid (epsilon-Ahx), aminoisobutyric acid (Aib), aminomethylpyrrole carboxylic acid, aminopiperidinecarboxylic acid, aminoserine (Ams), aminotetrahydropyran-4-carboxylic acid, arginine N-methoxy-N-methyl amide, beta-aspartic acid (beta-Asp), azetidine carboxylic acid, 3-(2-benzothiazolyl)alanine, alpha-tert-butylglycine, 2-amino-5-ureido-n-valeric acid (citrulline, Cit), beta-Cyclohexylalanine (Cha), acetamidomethyl-cysteine, diaminobutanoic acid (Dab), diaminopropionic acid (Dpr), dihydroxyphenylalanine (DOPA), dimethylthiazolidine (DMTA), gamma-Glutamic acid (gamma-Glu), homoserine (Hse), hydroxyproline (Hyp), isoleucine N-methoxy-N-methyl amide, methyl-isoleucine (Melle), isonipecotic acid (Isn), methyl-leucine (MeLeu), methyl-lysine, dimethyl-lysine, trimethyl-lysine, methanoproline, methionine-sulfoxide (Met(O)), methionine-sulfone (Met($O_2$)), norleucine (Nle), methyl-norleucine (Me-Nle), norvaline (Nva), ornithine (Orn), para-aminobenzoic acid (PABA), penicillamine (Pen), methylphenylalanine (MePhe), 4-Chlorophenylalanine (Phe(4-Cl)), 4-fluorophenylalanine (Phe(4-F)), 4-nitrophenylalanine (Phe(4-$NO_2$)), 4-cyanophenylalanine ((Phe (4-CN)), phenylglycine (Phg), piperidinylalanine, piperidinylglycine, 3,4-dehydroproline, pyrrolidinylalanine, sarcosine (Sar), selenocysteine (Sec), O-Benzyl-phosphoserine, 4-amino-3-hydroxy-6-methylheptanoic acid (Sta), 4-amino-5-cyclohexyl-3-hydroxypentanoic acid (ACHPA), 4-amino-3-hydroxy-5-phenylpentanoic acid (AHPPA), 1,2,3,4,-tetrahydro-isoquinoline-3-carboxylic acid (Tic), tetrahydropyranglycine, thienylalanine (Thi), O-benzyl-phosphotyrosine, O-Phosphotyrosine, methoxytyrosine, ethoxytyrosine, O-(bis-dimethylamino-phosphono)-tyrosine, tyrosine sulfate tetrabutylamine, methyl-valine (Me-Val), and alkylated 3-mercaptopropionic acid. In some embodiments, the clamp peptide, or the first peptide arm, the second peptide arm, or the bridge peptide thereof, described herein are glycosylated, amidated, carboxylated, phosphorylated, esterified, N-acylated, cyclized via, e.g., a disulfide bridge, or converted into a salt (e.g., an acid addition salt, a basic addition salt), and/or optionally dimerized, multimerized, or polymerized, or conjugated.

In exemplary aspects, the clamp peptide comprises a sequence of any one of SEQ ID NOs: 16-23 and a sequence of any one of SEQ ID NOs: 24-31. In exemplary aspects, the clamp peptide comprises a sequence of any one of SEQ ID NOs: 16-23 and a sequence of any one of SEQ ID NOs: 24-31 and an additional sequence of, e.g., intervening amino acids or amino acid sequences or a bridge peptide. In exemplary aspects, the clamp peptide comprises a pair of amino acid sequences comprising SEQ ID NOs: 16 and 24 or SEQ ID NOs: 16 and 25 or SEQ ID NOs: 18 and 26 or SEQ ID NOs: 18 and 27 or SEQ ID NOs: 20 and 24 or SEQ ID NOs: 20 and 25 or SEQ ID NOs: 22 and 26 or SEQ ID NOs: 22 and 27. In some aspects, the clamp peptide comprises a pair of amino acid sequences comprising SEQ ID NOs: 18 and 26. In some aspects, the clamp peptide comprises a pair of amino acid sequences comprising SEQ ID NOs: 20 and 25. In some aspects, the clamp peptide comprises a pair of amino acid sequences comprising SEQ ID NOs: 22 and 26. In exemplary aspects, the clamp peptide comprises a bridge peptide that joins one sequence to the other. Optionally, the bridge peptide comprises SEQ ID NO: 32. In various aspects, the clamp peptide comprises the sequence of any one of SEQ ID NOs: 8-15. In some aspects, the clamp peptide comprises the sequence of SEQ ID NO: 10. In some aspects, the clamp peptide comprises the sequence of SEQ ID NO: 13. In some aspects, the clamp peptide comprises the sequence of SEQ ID NO: 14.

Methods of Antibody or Antigen-Binding Fragment Production

Suitable methods of making antibodies are known in the art. For instance, standard hybridoma methods are described in, e.g., Harlow and Lane (eds.), Antibodies: A Laboratory Manual, CSH Press (1988), and CA. Janeway et al. (eds.), Immunobiology, 5$^{th}$ Ed., Garland Publishing, New York, N.Y. (2001)). Monoclonal antibodies for use in the methods of the disclosure may be prepared using any technique which provides for the production of antibody molecules by continuous cell lines in culture. These include but are not limited to the hybridoma technique originally described by Koehler and Milstein (Nature 256: 495-497, 1975), the human B-cell hybridoma technique (Kosbor et al., Immunol Today 4:72, 1983; Cote et al., Proc Natl Acad Sci 80: 2026-2030, 1983) and the EBV-hybridoma technique (Cole et al., Monoclonal Antibodies and Cancer Therapy, Alan R Liss Inc, New York N.Y., pp 77-96, (1985). Alternatively, other methods, such as EBV-hybridoma methods (Haskard and Archer, J. Immunol. Methods, 74(2), 361-67 (1984), and Roder et al., Methods Enzymol., 121, 140-67 (1986)), and bacteriophage vector expression systems (see, e.g., Huse et al., Science, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1). Antibodies may also be produced by inducing in vivo production in the lymphocyte population or by screening recombinant immunoglobulin libraries or panels of highly specific binding reagents as disclosed in Orlandi et al (Proc Natl Acad Sci 86: 3833-3837; 1989), and Winter G and Milstein C (Nature 349: 293-299, 1991). If the full sequence of the antibody or antigen-binding fragment is known, then methods of producing recombinant proteins may be employed. See, e.g., "Protein production and purification" Nat Methods 5(2): 135-146 (2008).

Phage display also can be used to generate the antibody of the present disclosures. In this regard, phage libraries encoding antigen-binding variable (V) domains of antibodies can be generated using standard molecular biology and recombinant DNA techniques (see, e.g., Sambrook et al. (eds.), Molecular Cloning, A Laboratory Manual, 3$^{rd}$ Edition, Cold Spring Harbor Laboratory Press, New York (2001)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150). Related methods also are described in U.S. Pat. Nos. 5,403,484; 5,571,698; 5,837,500; 5,702,892. The techniques described in U.S. Pat. Nos. 5,780,279; 5,821,047; 5,824,520; 5,855,885; 5,858,657; 5,871,907; 5,969,108; 6,057,098; and 6,225,447.

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 BI, and United Kingdom Patent No. 2188638. Humanized antibodies can also be generated using the antibody resurfacing technology described in U.S. Pat. No. 5,639,641 and Pedersen et al., J. Mol. Biol, 235, 959-973 (1994). A preferred chimeric or humanized antibody has a human constant region, while the variable region, or at least a CDR, of the antibody is derived from a non-human species. Methods for humanizing non-human antibodies are well known in the art. (See U.S. Pat. Nos. 5,585,089, and 5,693,762.)

Techniques developed for the production of "chimeric antibodies", the splicing of mouse antibody genes to human antibody genes to obtain a molecule with appropriate antigen specificity and biological activity, can be used (Morrison et al., Proc Natl Acad Sci 81: 6851-6855 (1984); Neuberger et al., Nature 312: 604-608 (1984); Takeda et al., Nature 314: 452-454 (1985)). Alternatively, techniques described for the production of single chain antibodies (U.S. Pat. No. 4,946,778) can be adapted to produce ZIKV-specific single chain antibodies.

Likewise, using techniques known in the art to isolate CDRs, compositions comprising CDRs are generated. Compositions comprising one, two, and/or three CDRs of a heavy chain variable region or a light chain variable region of a monoclonal antibody can be generated. The CDRs of exemplary antibodies are provided herein as SEQ ID NOs: 1-6, 21-26, 29-34, 37-42, 45-50, and 58-63. Techniques for cloning and expressing nucleotide and polypeptide sequences are well-established in the art (see e.g. Sambrook et al., *Molecular Cloning: A Laboratory Manual, 2$^{nd}$ Edition*, Cold Spring Harbor, N.Y. (1989)). The amplified CDR sequences are ligated into an appropriate expression vector. The vector comprising one, two, three, four, five and/or six cloned CDRs optionally contains additional polypeptide encoding regions linked to the CDR.

Chemically constructed bispecific antibodies may be prepared by chemically cross-linking heterologous Fab or F(ab')$_2$ fragments by means of chemicals such as heterobifunctional reagent succinimidyl-3-(2-pyridyldithiol)-propionate (SPDP, Pierce Chemicals, Rockford, Ill.). The Fab and F(ab')$_2$ fragments can be obtained from intact antibody by digesting it with papain or pepsin, respectively (Karpovsky et al., J. Exp. Med. 160:1686-701 (1984); Titus et al., J. Immunol., 138:4018-22 (1987)).

Methods of testing antibodies for the ability to bind to the epitope of the ZIKV regardless of how the antibodies are produced are known in the art and include any antibody-antigen binding assay, such as, for example, radioimmunoassay (RIA), ELISA, Western blot, immunoprecipitation, surface plasmon resonance, and competitive inhibition assays (see, e.g., Janeway et al., infra, and U.S. Patent Application Publication No. 2002/0197266).

Polypeptides

A polypeptide comprising a sequence of any one of SEQ ID NOs: 16-23 and a sequence of any one of SEQ ID NOs: 24-31 is further provided herein. In exemplary aspects, the amino acid sequence of the polypeptide comprises a sequence of any one of SEQ ID NOs: 16-23 and a sequence of any one of SEQ ID NOs: 24-31 and an additional sequences of, e.g., intervening amino acids or amino acid sequences or a bridge peptide. In exemplary aspects, the polypeptide comprises a pair of amino acid sequences comprising SEQ ID NOs: 16 and 24 or SEQ ID NOs: 16 and 25 or SEQ ID NOs: 18 and 26 or SEQ ID NOs: 18 and 27 or SEQ ID NOs: 20 and 24 or SEQ ID NOs: 20 and 25 or SEQ ID NOs: 22 and 26 or SEQ ID NOs: 22 and 27. In some aspects, the polypeptide comprises a pair of amino acid sequences comprising SEQ ID NOs: 18 and 26. In some aspects, the polypeptide comprises a pair of amino acid sequences comprising SEQ ID NOs: 20 and 25. In some aspects, the polypeptide comprises a pair of amino acid sequences comprising SEQ ID NOs: 22 and 26. In exemplary aspects, the polypeptide comprises a bridge peptide that joins one sequence to the other. Optionally, the bridge peptide comprises SEQ ID NO: 32. In various aspects, the polypeptide comprises the sequence of any one of SEQ ID NOs: 8-15. In some aspects, the polypeptide comprises the sequence of SEQ ID NO: 10. In some aspects, the polypeptide comprises the sequence of SEQ ID NO: 13. In some aspects, the polypeptide comprises the sequence of SEQ ID NO: 14.

In various aspects, the polypeptide comprises any one of the above sequences with one or more amino acid modifications. As used herein an "amino acid modification" refers to (i) a substitution of an amino acid with a different amino acid (naturally-occurring or coded or non-coded or non-naturally-occurring amino acid), (ii) an addition of an amino acid (naturally-occurring or coded or non-coded or non-naturally-occurring amino acid), or (iii) a deletion of one or more amino acids.

In some or any embodiments, the amino acid substitution is a conservative amino acid substitution. As used herein, the term "conservative amino acid substitution" is defined herein as the substitution of one amino acid with another amino acid having similar properties, e.g., size, charge, hydrophobicity, hydrophilicity, and/or aromaticity, and includes exchanges within one of the following five groups:

I. Small aliphatic, nonpolar or slightly polar residues: Ala, Ser, Thr, Pro, Gly;
 II. Polar, negatively charged residues and their amides and esters: Asp, Asn, Glu, Gln, cysteic acid and homocysteic acid;
 III. Polar, positively charged residues: His, Arg, Lys; Ornithine (Orn)
 IV. Large, aliphatic, nonpolar residues: Met, Leu, Ile, Val, Cys, Norleucine (Nle), homocysteine
 V. Large, aromatic residues: Phe, Tyr, Trp, acetyl phenylalanine In alternative embodiments, the amino acid substitution is not a conservative amino acid substitution, e.g., is a non-conservative amino acid substitution.

In exemplary aspects, the polypeptide of the present disclosure binds to ZIKV and not to DENV or any other flavivirus. In exemplary aspects, the polypeptide binds to only ZIKV even in the presence of DENV, optionally, even in the presence of other flavivirus proteins, e.g., proteins of WNV, JEV, YFV.

Modified Binding Constructs and Conjugates

The binding constructs described herein can be modified, for instance, by glycosylation, amidation, carboxylation, or phosphorylation, or by the creation of acid addition salts, amides, esters, in particular C-terminal esters, and N-acyl derivatives. Such modified binding constructs disclosed herein may have additional activities, enhanced or reduced biological activity, or other characteristics, such as increased or decreased half-life, as compared to the non-derivatized molecules.

In exemplary embodiments, the binding constructs of the present disclosure are attached, linked, joined, or conjugated to a second moiety (e.g., a heterologous moiety) and the resulting product is a conjugate. Accordingly, provided herein are conjugates comprising the binding constructs described herein (covalently or non-covalently) linked to a heterologous moiety. As used herein, the term "heterologous moiety" refers to any molecule (chemical or biochemical, naturally-occurring or non-coded) which is different from the binding constructs of the invention. Exemplary heterologous moieties include, but are not limited to, a polymer, a carbohydrate, a lipid, a nucleic acid, an oligonucleotide, a DNA or RNA, an amino acid, peptide, polypeptide, protein, therapeutic agent, (e.g., a cytotoxic agent, cytokine), an element or metal, a virus, a diagnostic agent or a detecting agent.

Conjugates: Fc Fusions

For substituents such as an Fc region of human IgG, the fusion can be fused directly to a binding construct of the invention or fused through an intervening sequence. For example, a human IgG hinge, CH2 and CH3 region may be fused at either the N-terminus or C-terminus of a binding construct to attach the Fc region. The resulting Fc-fusion construct enables purification via a Protein A affinity column (Pierce, Rockford, Ill.). Peptide and proteins fused to an Fc region can exhibit a substantially greater half-life in vivo than the unfused counterpart. A fusion to an Fc region allows for dimerization/multimerization of the fusion polypeptide. The Fc region may be a naturally occurring Fc region, or may be modified for superior characteristics, e.g., therapeutic or diagnostic qualities, circulation time, reduced aggregation. As noted above, in some embodiments, the binding constructs are conjugated, e.g., fused to an immunoglobulin or portion thereof (e.g., variable region, CDR, or Fc region). Known types of immunoglobulins (Ig) include IgG, IgA, IgE, IgD or IgM. The Fc region is a C-terminal region of an Ig heavy chain, which is responsible for binding to Fc receptors that carry out activities such as recycling (which results in prolonged half-life), antibody dependent cell-mediated cytotoxicity (ADCC), and complement dependent cytotoxicity (CDC).

For example, according to some definitions the human IgG heavy chain Fc region stretches from Cys226 to the C-terminus of the heavy chain. The "hinge region" generally extends from Glu216 to Pro230 of human IgG1 (hinge regions of other IgG isotypes may be aligned with the IgG1 sequence by aligning the cysteines involved in cysteine bonding). The Fc region of an IgG includes two constant domains, CH2 and CH3. The CH2 domain of a human IgG Fc region usually extends from amino acids 231 to amino acid 341. The CH3 domain of a human IgG Fc region usually extends from amino acids 342 to 447. References made to amino acid numbering of immunoglobulins or immunoglobulin fragments, or regions, are all based on Kabat et al. 1991, Sequences of Proteins of Immunological Interest, U.S. Department of Public Health, Bethesda, Md. In related embodiments, the Fc region may comprise one or more native or modified constant regions from an immunoglobulin heavy chain, other than CH1, for example, the CH2 and CH3 regions of IgG and IgA, or the CH3 and CH4 regions of IgE.

Suitable heterologous moieties include portions of immunoglobulin sequence that include the FcRn binding site. FcRn, a salvage receptor, is responsible for recycling immunoglobulins and returning them to circulation in blood. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The major contact sites include amino acid residues 248, 250-257, 272, 285, 288, 290-291, 308-311, and 314 of the CH2 domain and amino acid residues 385-387, 428, and 433-436 of the CH3 domain.

Amino acid modifications may be made to the Fc region of an immunoglobulin. Such variant Fc regions comprise at least one amino acid modification in the CH3 domain of the Fc region (residues 342-447) and/or at least one amino acid modification in the CH2 domain of the Fc region (residues 231-341). Mutations believed to impart an increased affinity for FcRn include T256A, T307A, E380A, and N434A (Shields et al. 2001, J. Biol. Chem. 276:6591). Other mutations may reduce binding of the Fc region to FcγRI, FcγRIIA, FcγRIIB, and/or FcγRIIIA without significantly reducing affinity for FcRn. For example, substitution of the Asn at position 297 of the Fc region with Ala or another amino acid removes a highly conserved N-glycosylation site and may result in reduced immunogenicity with concomitant prolonged half-life of the Fc region, as well as reduced binding to FcγRs (Routledge et al. 1995, Transplantation 60:847; Friend et al. 1999, Transplantation 68:1632; Shields et al. 1995, J. Biol. Chem. 276:6591). Amino acid modifications at positions 233-236 of IgG1 have been made that reduce binding to FcγRs (Ward and Ghetie 1995, Therapeutic Immunology 2:77 and Armour et al. 1999, Eur. J. Immunol. 29:2613). Some exemplary amino acid substitutions are described in U.S. Pat. Nos. 7,355,008 and 7,381,408, each incorporated by reference herein in its entirety.

Heterologous Moieties: Polymers, Carbohydrates, Lipids, Elements, Metals, Viruses, Therapeutic Agents In exemplary embodiments, the heterologous moiety is a polymer. The polymer may be branched or unbranched. The polymer may be of any molecular weight. The polymer in some embodiments has an average molecular weight of between about 2 kDa to about 100 kDa (the term "about" indicating that in preparations of a water soluble polymer, some molecules will weigh more, some less, than the stated molecular weight). In some embodiments, the polymer is modified to have a single reactive group, such as an active ester for acylation or an aldehyde for alkylation, so that the degree of polymerization may be controlled. The polymer in some embodiments is water soluble so that the protein to which it is attached does not precipitate in an aqueous environment, such as a physiological environment. In some embodiments, when, for example, the composition is used for therapeutic use, the polymer is pharmaceutically acceptable. Additionally, in some aspects, the polymer is a mixture of polymers, e.g., a co-polymer, a block co-polymer. In exemplary aspects, the heterologous moiety is a polymer, optionally, polystyrene or nitrocellulose.

In some embodiments, the heterologous moiety is a carbohydrate. In some embodiments, the carbohydrate is a monosaccharide (e.g., glucose, galactose, fructose), a disaccharide (e.g., sucrose, lactose, maltose), an oligosaccharide (e.g., raffinose, stachyose), a polysaccharide (a starch, amylase, amylopectin, cellulose, chitin, callose, laminarin, xylan, mannan, fucoidan, galactomannan.

In some embodiments, the heterologous moiety is a lipid. The lipid, in some embodiments, is a fatty acid, eicosanoid, prostaglandin, leukotriene, thromboxane, N-acyl ethanolamine), glycerolipid (e.g., mono-, di-, tri-substituted glycerols), glycerophospholipid (e.g., phosphatidylcholine, phosphatidylinositol, phosphatidylethanolamine, phosphatidylserine), sphingolipid (e.g., sphingosine, ceramide), sterol lipid (e.g., steroid, cholesterol), prenol lipid, saccharolipid, or a polyketide, oil, wax, cholesterol, sterol, fat-soluble vitamin, monoglyceride, diglyceride, triglyceride, a phospholipid.

In exemplary aspects, the heterologous moiety is an element, such as a gold particle or other metal. In exemplary aspects, the heterologous moiety is a virus. In exemplary aspects, the virus is ZIKV. In some embodiments, the heterologous moiety is a therapeutic agent. The therapeutic agent may be any of those known in the art.

Conjugates: Detecting Agents

In exemplary embodiments, the binding construct is conjugated to a detecting agent. In exemplary embodiments, the detecting agent is capable of emitting a detectable (measurable) signal based on enzymatic activity, radioactivity, chromogenic activity, and/or binding activity. In exemplary embodiments, the signal is radioactive, chromogenic, colorimetric, fluorometric, chemiluminescent, enhanced chemiluminescent, direct fluorescent, time-resolved fluorescent, direct chemiluminescent, phosphorescent, enzymatic, or based on binding of a micro- or nanoparticle, streptavidin/avidin-biotin and protein A. In exemplary embodiments, the detecting agent comprises an enzyme, a radioactive isotope, a DNA reporter, a chromogenic or fluorogenic reporter, or an electrochemiluminescent tag. In exemplary aspects, the enzyme is horseradish peroxidase (HRP), alkaline phosphatase (AP), glucose oxidase, or beta-galactosidase. In exemplary aspects, the enzyme when exposed to certain reagents causes chemiluminescence or light production. In exemplary aspects, the radioisotope is $I^{125}$. In exemplary aspects, the DNA reporter is a DNA probe. In exemplary aspects, the fluorogenic reporter is phycoerythrin (PE), e.g., B-PE, R-PE, or allophycocyanin (APC). In exemplary aspects, the detecting agent is a fluorophore, chromophore, radioisotope, enzymatic label, or biotin.

The binding constructs in exemplary aspects is linked to a detecting agent (e.g., a detectable label or a reporter group), including, but not limited to a radiolabel, a fluorescent label, an enzyme (e.g., that catalyzes a calorimetric or fluorometric reaction), a substrate, a solid matrix, or a carrier (e.g., biotin or avidin). In exemplary aspects, the fluorescent label comprises a rhodamine dye, fluorescein dye and/or a cyanine dye. In exemplary embodiments, the fluorescent label comprises a set of dyes, e.g., a rhodamine dye, TAMRA, and a fluorescein dye, FAM. In another embodiment, the fluorescent label comprises of a set of fluorescent dyes formed by selecting two or more dyes from the group consisting of Oregon Green 488, Flitorescein-EX, fluorescein isothiocyanate, Rhodamine Red-X, Lissamine rhodamine B, Calcein, Fluorescein, Rhodamine, one or more BODIPY dyes, Texas Red, Oregon Green 514, and one or more Alexa Fhiors. Representative BODIPY dyes include BODIPY FL, BODIPY R6G, BODIPY™ R, BODIPY 581/591, BODIPY TR, BODIPY 630/650 and BODIPY 650/665. Representative Alexa Fluors include Alexa Fluor 350, 405, 430, 488, 500, 514, 532, 546, 555, 568, 594, 610, 633, 635, 647, 660, 680, 700, 750 and 790. In exemplary aspects, the fluorescent label comprises one or more of Oregon Green 488, fluorescein-EX, FITC, Rhodamine Red-X, Lissamine rhodamine B, calcein, fluorescein, rhodamine, BODIPYS, and Texas Red, e.g. which are disclosed in Molecular Probes Handbook, 11th Edition (2010). In exemplary aspects, the detectable label is selected from radioisotopes, chromophores, fluorophores, fluorochromes, enzymes (e.g., horseradish peroxidase), linker molecules or other moieties or compounds which either emit a detectable signal (e.g., radioactivity, fluorescence, color) or emit a detectable signal after exposure of the label to its substrate. A variety of detectable label/substrate pairs (e.g., horseradish peroxidase/diaminobenzidine, biotin/streptavidin, luciferase/luciferin), methods for labeling antibodies, and methods for using labeled secondary antibodies to detect an antigen are well known in the art. See, e.g., Harlow and Lane, eds. (Using Antibodies: A Laboratory Manual (1999) Cold Spring Harbor Laboratory Press, Cold Spring Harbor, N.Y.).

Conjugates: Dimers & Multimers

In some embodiments, the binding construct is provided as a dimer or a multimer in which more than one binding construct of the invention are linked together. The dimer in some aspects is a homodimer comprising two binding constructs of the same type (e.g., same structure) linked together. In alternative aspects, the dimer is a heterodimer comprising two binding constructs of the invention, wherein the two binding constructs are structurally distinct from each other. The multimer in some aspects is a homomultimer comprising more than one binding construct of the invention and each binding construct is of the same type (e.g., same structure). In alternative aspects, the multimer is a heteromultimer comprising more than one binding construct of the invention and wherein at least two binding constructs of the heteromultimer are structurally distinct from the other. Two or more of the binding constructs can be linked together using standard linking agents and procedures known to those skilled in the art. In certain embodiments, the linker connecting the two (or more) binding constructs is a linker known in the art. In some embodiments, the linker is a disulfide bond. For example, each monomer of the dimer may comprise a sulfhydryl and the sulfur atom of each participates in the formation of the disulfide bond.

Nucleic Acids

Further provided herein are nucleic acids comprising a nucleotide sequence encoding any of the binding constructs (e.g., antibodies, antigen-binding fragments, antibody mimetics) or polypeptides or conjugates described herein. By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

In exemplary aspects, the nucleic acids of the present disclosure are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

In some aspects, the nucleic acid encodes only a portion of the antibodies, antigen-binding fragments, polypeptides, or conjugates. For example, when the conjugate comprises a polymer, which does not comprise amino acids and thus is not encoded by a nucleic acid, the nucleic acid encodes only the part of the conjugate which can be encoded by a nucleic acid. In exemplary embodiments, the nucleic acid comprises a nucleotide sequence encoding a polypeptide comprising an amino acid sequence comprising each of SEQ ID NOs: 8-15.

The nucleic acids are useful in e.g., methods of recombinant production of the binding constructs of the invention.

Recombinant Expression Vector

The nucleic acids of the invention can be incorporated into a recombinant expression vector, or "vector". In this regard, the invention provides recombinant expression vectors or "vectors" comprising any of the nucleic acids of the invention. For purposes herein, the term "recombinant expression vector" or "vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the altered nucleotides or non-naturally occurring internucleotide linkages do not hinder the transcription or replication of the vector.

The recombinant expression vector of the invention can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGTIO, λGTI 1, λZapII (Stratagene), λEMBL4, and λNMI 149, also can be used. Examples of plant expression vectors include pBIOI, pBI101.2, pBI101.3, pBI121 and pBIN19 (Clontech). Examples of animal expression vectors include pEUK-Cl, pMAM and pMAMneo (Clontech). Preferably, the recombinant expression vector is a viral vector, e.g., a retroviral vector.

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEI, 2μ plasmid, λ, SV40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector can comprise a native or non-non-native promoter operably linked to the nucleotide sequence encoding the polypeptide (including functional portions and functional variants thereof), or to the nucleotide sequence which is complementary to or which hybridizes to the nucleotide sequence encoding the polypeptide. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

Host Cells

The invention further provides a host cell comprising any of the nucleic acids or recombinant expression vectors described herein. As used herein, the term "host cell" refers to any type of cell that can contain and express the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α E. coli cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing a recombinant polypeptide the host cell is preferably a mammalian cell, e.g., a CHO cell.

Kits

Provided herein are kits comprising any one or more of the binding constructs (e.g., antibody or antigen-binding fragment or antibody mimetic) or polypeptide or conjugate or nucleic acid or vector or host cell, as described herein, or a combination of any of the foregoing. In exemplary aspects, the binding construct is provided in the kit in a predetermined amount or concentration. For example, the kit may be a detection kit comprising a predetermined amount of the binding construct for detecting ZIKV in a sample. In exemplary embodiments, the one or more of the binding constructs of the present disclosure is provided in the kit in an aqueous solution. In exemplary aspects, the aqueous solution is provided to the end-user on dry ice. In some aspects, the aqueous solution is provided to the end-user separately from the other components of the kit. In exemplary embodiments, the binding constructs of the present disclosure are provided in the kit in a lyophilized or other freeze-dried form. In exemplary aspects, the binding constructs of the present disclosures are provided in the kit in a frozen or cryopreserved form.

In exemplary aspects, the kit comprises a solid support, and in exemplary aspects the binding construct (e.g., antibody or antigen-binding fragment or antibody mimetic) or polypeptide or conjugate is pre-coated onto the solid support. In exemplary aspects, the kit comprises a solid support selected from the group consisting of a tube, a dish, a flask, a bag, a plate (e.g., a microtiter plate), a membrane, a filter, a bead, a fiber, a probe, and the like. In exemplary aspects, the solid support is made of a polymer. In exemplary aspects, the solid support is made of agarose, cellulose, dextran, polyacrylamide, latex, or controlled pore glass. In exemplary aspects, the solid support is made of polyvinyl difluoride (PVDF), nitrocellulose, nylon 66, protran nitrocellulose, or paper. In exemplary aspects, the membrane is one of the Immobilon®, Protran®, QuickDraw®, Westran®, Whatman® or Hybond® membranes (Sigma-Aldrich, St. Louis, Mo.). In exemplary aspects, the solid support is a polymer bead, a microtiter plate, a membrane or a filter. In exemplary aspects, the kit comprises a solid support comprising pre-aliquoted amounts of the antibody or antigen-binding fragment or polypeptide or conjugate.

In exemplary aspects, the kit comprises a capture molecule which binds to a Zika virus. In exemplary aspects, the capture molecule is bound to the solid support. In exemplary aspects, the capture molecule is a binding construct (e.g., an antibody or an antigen-binding fragment thereof or antibody mimetic). In particular aspects, the capture molecule is a clamp peptide as described herein.

In exemplary aspects, the kit comprises additional reagents, substrates, solvents, buffers, diluents, etc., used in the detection methods described herein. In exemplary aspects, any one or more of the additional components are provided in the kit in a predetermined amount, e.g., the amount necessary and suitable for a detection assay. In exemplary aspects, the kit comprises a blocking agent, such as, for example, a solution comprising bovine serum albumin (BSA). In exemplary aspects, the kit comprises a wash buffer, such as, for example, phosphate buffered saline or TRIS buffer. In exemplary aspects, the kit comprises a detecting agent. Suitable detecting agents are known in the art and described herein. See, e.g., the section herein entitled "Conjugates: Detecting Agents". In exemplary aspects, the detecting agent comprises a secondary antibody linked to a detectable label. The detectable label, in some aspects, is an enzyme, e.g., horseradish peroxidase (HRP). In exemplary aspects, the kit comprises a substrate of the enzyme, and in some aspects, the substrate is a chromogenic substrate. Suitable substrates of the enzyme of the detectable label are known in the art and include but is not limited to 2,2'-azino-bis(3-ethylbenzothiazoline-6-sulphonic acid) (ABTS), o-phenylenediamine dihydrochloride (OPD), AmplexRed, 3,3'-Diaminobenzidine (DAB), aminoethyl carbazole (AEC), 3,3',5,5'-Tetramethylbenzidine (TMB), Homovanillic acid, and Luminol. In exemplary aspects, the secondary antibody of the detecting agent binds to the binding construct (e.g., antibody or antigen-binding fragment or antibody mimetic) or polypeptide of the present disclosure, which binds to a Zika virus (ZIKV) protein and does not bind to a Dengue virus (DENV) protein.

In exemplary aspects, the kit comprises reagents and materials for an ELISA, e.g., a sandwich ELISA. In exemplary aspects, the kit comprises a ZIKV-specific binding construct of the present disclosures (e.g., one comprising the amino acid sequence of SEQ ID NOs: 8-15) as a detection antibody, a solid support (e.g., a microtiter plate or nitrocellulose) coated with a capture molecule and blocked with a blocking agent, e.g., BSA. In exemplary aspects, the kit comprises a detecting agent. As used herein "detection antibody" refers to any detection molecule, such as for example a detection binding construct or detection antibody mimetic or a detection claim peptide. In exemplary aspects, the detectable label is horseradish peroxidase (HRP). In exemplary aspects, the kit comprises a chromogenic substrate for HRP. In exemplary aspects, a positive control and/or a negative control is provided for the ELISA.

In alternative aspects, the kit comprises reagents and materials for another immunoassay. In exemplary aspects, the kit comprises a ZIKV-specific binding construct of the present disclosure (e.g., one comprising the amino acid sequence of SEQ ID NOs: 8-15), as a detection antibody, a solid support (e.g., a microtiter plate or nitrocellulose) coated with a capture molecule. In exemplary aspects, the kit comprises a detecting agent.

Assay Systems

The present disclosure provides an assay system. In exemplary aspects, the assay system is suitable for detecting a ZIKV infection and ZIKV immunity in a subject. Without being bound to a particular theory, the detection of ZIKV-specific antibodies in the sample of a subject represents prior exposure to ZIKV and hence ZIKV immunity. In exemplary aspects, the assay system is a lateral flow assay system. In exemplary aspects, the assay system is an immunochromatographic assay system. Lateral flow assay systems are known in the art. See, e.g., Grant et al., Vaccine 34(46): 5656-5663 (2016); and Cross et al., J Infect Dis 214(suppl3):S210-S217 (2016).

In exemplary aspects, the assay system comprises a porous matrix comprising at least three zones, Zone A, Zone B, and Zone C, wherein Zone A comprises binding construct as described herein, wherein the binding construct is not bound to a Zika virus, Zone B comprises a binding construct as described herein, wherein the binding construct is bound to a Zika virus, and Zone C comprises a secondary antibody which binds the binding construct of Zone A and Zone B, optionally, wherein the secondary antibody binds to antibody binding region of the binding construct (e.g., antibody mimetic) of Zone A and Zone B. In exemplary aspects, Zone A is purposed for testing for an active ZIKV infection in the subject, Zone B is purposed for testing for ZIKV immunity or prior exposure to ZIKV, and Zone C is purposed as a control. In exemplary aspects, Zones A to C are arranged along a horizontal axis. In exemplary aspects, each of Zones A, B, and C is flanked by an intervening zone of the porous matrix lacking the binding construct.

In exemplary aspects, the assay system further comprises a sample application pad, a particle conjugate zone, a wick, and/or a backing. In exemplary aspects, the porous matrix comprising Zones A, B, and C, the sample application pad, the particle conjugate zone, and the wick are arranged along a horizontal axis. In some aspects, the horizontal axis is the same as the horizontal axis along which Zones A to C are arranged. In exemplary aspects, the assay system is arranged such that the sample application pad and the wick are located at opposite ends of the assay system along the horizontal axis. In some aspects, the particle conjugate zone is flanked by the sample application pad and the porous matrix comprising Zones A, B, and C. In some aspects, the porous matrix is flanked by the particle conjugate and the wick. In exemplary aspects, the backing is positioned below the porous matrix, the sample application pad, the particle conjugate zone, and the wick. In some aspects, the backing provides a physical support for the sample application pad, the particle conjugate zone, the porous matrix, and the wick.

In exemplary aspects, the particle conjugate zone is bound to a conjugate comprising a binding construct or polypeptide as described herein, bound to an element or polymer. In exemplary aspects, the element is a gold particle or the polymer is polystyrene. In exemplary aspects, the conjugate comprises an antibody mimetic (e.g., clamp peptide) as described herein. In some aspects, the antibody of the conjugate comprises any one or more of SEQ ID NOs: 8-15.

Figure 8:
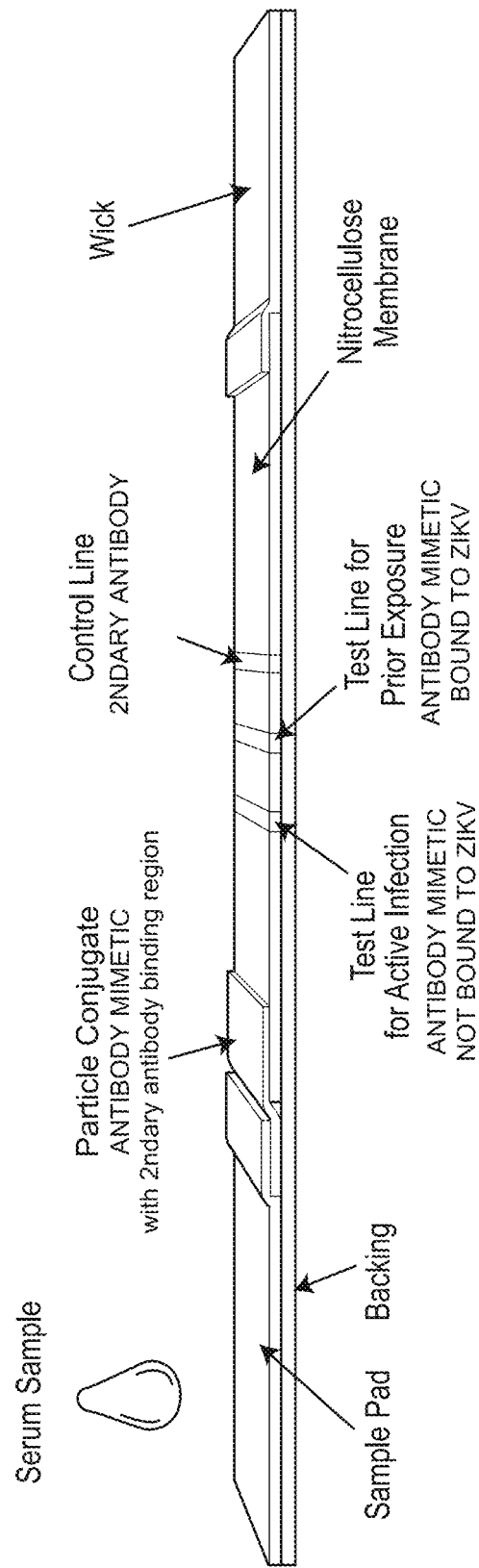
FIG. 8 is an illustration of a device for the lateral flow assay which detects active ZIKV infection and prior ZIKV exposure.

In exemplary aspects, each of Zone A and Zone B is bound to a binding construct as described herein. In some aspects, the binding construct bound to Zone A and Zone B is an antibody mimetic, such as any of those described herein. In exemplary aspects, the binding construct is a clamp peptide. In exemplary aspects, the clamp peptide comprises a sequence of any one of SEQ ID NOs: 16-23 and a sequence of any one of SEQ ID NOs: 24-31. In exemplary aspects, the clamp peptide comprises a sequence of any one of SEQ ID NOs: 16-23 and a sequence of any one of SEQ ID NOs: 24-31 and an additional sequence of, e.g., intervening amino acids or amino acid sequences or a bridge peptide. In exemplary aspects, the clamp peptide comprises a pair of amino acid sequences comprising SEQ ID NOs: 16 and 24 or SEQ ID NOs: 16 and 25 or SEQ ID NOs: 18 and 26 or SEQ ID NOs: 18 and 27 or SEQ ID NOs: 20 and 24 or SEQ ID NOs: 20 and 25 or SEQ ID NOs: 22 and 26 or SEQ ID NOs: 22 and 27. In some aspects, the clamp peptide comprises a pair of amino acid sequences comprising SEQ ID NOs: 18 and 26. In some aspects, the clamp peptide comprises a pair of amino acid sequences comprising SEQ ID NOs: 20 and 25. In some aspects, the clamp peptide comprises a pair of amino acid sequences comprising SEQ ID NOs: 22 and 26. In exemplary aspects, the clamp peptide comprises a bridge peptide that joins one sequence to the other. Optionally, the bridge peptide comprises SEQ ID NO: 32. In various aspects, the clamp peptide comprises the sequence of any one of SEQ ID NOs: 8-15. In some aspects, the clamp peptide comprises the sequence of SEQ ID NO: 10. In some aspects, the clamp peptide comprises the sequence of SEQ ID NO: 13. In some aspects, the clamp peptide comprises the sequence of SEQ ID NO: 14. An exemplary assay system is illustrated in FIG. 8 and FIGS. 9A and 9B demonstrate how the assay system may be used to detect a prior ZIKV infection (vis-à-vis ZIKV antibodies in the serum of a subject; FIG. 9B) and/or detect an active ZIKV infection (FIG. 9A).

In exemplary aspects, the porous matrix comprises a solid support. In exemplary aspects, the solid support is a filter or a membrane. In exemplary aspects, the porous matrix comprises nitrocellulose or polyvinylidene fluoride (PVDF). In exemplary aspects, the sample application pad comprises cellulose or glass fiber. In exemplary aspects, the wick comprises nitrocellulose.

Detection Methods

Binding constructs provided herein are useful in, e.g., detection methods that allow for unambiguous or specific detection of ZIKV in samples, e.g., clinical samples comprising, e.g., ZIKV and DENV and/or another flavivirus. The binding constructs can be used in any antibody-based assay or technique or any immunoassay known in the art, such as, but not limited to, radioimmunoassay (RIA), magnetic immunoassay (MIA), immunocytochemical (ICC) assays, immunohistochemical (IHC) assays, immunofluorescent assays, ELISA, EIA, ELISPOT, enzyme multiplied immunoassay, radiobinding assay, Western blotting, immunoprecipitation, dot blots, flow cytometry, real-time immunoquantitative PCR, protein microarrays and the like. See, e.g., *The Immunoassay Handbook* (Fourth Edition); Theory and Applications of Ligand Binding, ELISA and Related Techniques, ed. Wild, Elsevier Ltd. (Oxford, UK) 2013, Green and Sambrook, *Molecular Cloning: A Laboratory Manual*, 4th ed., Cold Spring Harbor Laboratory Press (Cold Spring Harbor, N.Y.) 2012, and *Immunoassay*, Diamandis and Christopolous, Academic Press 1996.

Accordingly, provided herein are uses of the binding construct (e.g., antibody or antigen-binding fragment, antibody mimetic, polypeptide, or conjugate), nucleic acid, vector, host cell, and/or kit described herein for detecting ZIKV in a sample. The present disclosure provides methods of detecting ZIKV in a sample obtained from a subject. In exemplary embodiments, the method comprises (i) contacting the sample with a binding construct (e.g., an antibody or antigen-binding fragment or antibody mimetic, or polypeptide or conjugate) as described herein to form a complex (e.g., an immunocomplex) comprising ZIKV and the binding construct (e.g., antibody, antigen-binding fragment, antibody mimetic, polypeptide, or conjugate), and (ii) detecting the complex. When the complex is detected, it is determined that the sample, and thus the subject, is positive for ZIKV, e.g., the subject is infected with ZIKV. In exemplary aspects, the binding construct is a clamp peptide. In exemplary aspects, the clamp peptide comprises a sequence of any one of SEQ ID NOs: 16-23 and a sequence of any one of SEQ ID NOs: 24-31. In exemplary aspects, the clamp peptide comprises a sequence of any one of SEQ ID NOs: 16-23 and a sequence of any one of SEQ ID NOs: 24-31 and an additional sequence of, e.g., intervening amino acids or amino acid sequences or a bridge peptide. In exemplary aspects, the clamp peptide comprises a pair of amino acid sequences comprising SEQ ID NOs: 16 and 24 or SEQ ID NOs: 16 and 25 or SEQ ID NOs: 18 and 26 or SEQ ID NOs: 18 and 27 or SEQ ID NOs: 20 and 24 or SEQ ID NOs: 20 and 25 or SEQ ID NOs: 22 and 26 or SEQ ID NOs: 22 and 27. In some aspects, the clamp peptide comprises a pair of amino acid sequences comprising SEQ ID NOs: 18 and 26. In some aspects, the clamp peptide comprises a pair of amino acid sequences comprising SEQ ID NOs: 20 and 25. In some aspects, the clamp peptide comprises a pair of amino acid sequences comprising SEQ ID NOs: 22 and 26. In exemplary aspects, the clamp peptide comprises a bridge peptide that joins one sequence to the other. Optionally, the bridge peptide comprises SEQ ID NO: 32. In various aspects, the clamp peptide comprises the sequence of any one of SEQ ID NOs: 8-15. In some aspects, the clamp peptide comprises the sequence of SEQ ID NO: 10. In some aspects, the clamp peptide comprises the sequence of SEQ ID NO: 13. In some aspects, the clamp peptide comprises the sequence of SEQ ID NO: 14.

In exemplary embodiments, detecting the complex comprises detecting a signal of a detecting agent. In exemplary embodiments, the signal is based on enzymatic activity, radioactivity, chromogenic activity, and/or binding activity. In exemplary embodiments, the signal is radioactive, chromogenic, colorimetric, fluorometric, chemiluminescent, enhanced chemiluminescent, direct fluorescent, time-resolved fluorescent, direct chemiluminescent, phosphorescent, enzymatic, or based on binding of a micro- or nanoparticle, streptavidin/avidin-biotin and protein A. In exemplary embodiments, the detecting agent comprises an enzyme, a radioactive isotope, a DNA reporter, a chromogenic or fluorogenic reporter, an electrochemiluminescent tag. In exemplary embodiments, detecting the complex comprises carrying out surface plasmon resonance to detect the complex or measuring change in resistance on an electrode (as FIX ZIKV binds to the antibody, antigen-binding fragment, polypeptide, or conjugate). See, Gonzalez-Diaz et al., "Plasmonic Au/Co/Au nanosandwiches with Enhanced Magneto-Optical Activity" Small 4(2): 202-5 (2008) and Tsekenis (2008). "Label-less immunosensor assay for myelin basic protein based upon an ac impedance protocol." Analytical Chemistry 80 (6): 2058-62 (2008). In exemplary aspects, the enzyme is horseradish peroxidase (HRP), alkaline phosphatase (AP), glucose oxidase, or beta-galactosidase. In exemplary aspects, the enzyme is exposed to reagents which cause them to chemiluminesce or produce light. In exemplary aspects, the radioisotope is 1125. In exemplary aspects, the DNA reporter is a DNA probe. See, e.g., Rajkovic, "Immunoquantitative real-time PCR for detection and quantification of *Staphylococcus aureus* enterotoxin B in foods." Applied and Environmental Microbiology 72 (10): 6593-9 (2006); and Gofflot "Immuno-quantitative polymerase chain reaction for detection and quantitation of prion protein." Journal of Immunoassay and Immunochemistry 25 (3): 241-58 (2004). In exemplary aspects, the fluorogenic reporter is phycoerythrin (PE) e.g., B-PE, R-PE, or allophycocyanin (APC).

In exemplary embodiments, the binding construct (e.g., antibody mimetic, antibody or antigen-binding fragment) or polypeptide is conjugated to a detecting agent. In exemplary embodiments, the conjugate comprises a detecting agent. In exemplary embodiments, the binding construct, e.g., antibody mimetic, antibody or antigen-binding fragment, or polypeptide is not conjugated to a detecting agent or the conjugate does not comprises a detecting agent. In such exemplary embodiments, the methods comprise contacting the sample with a secondary antibody comprising a detecting agent, wherein the secondary antibody binds to the binding construct, e.g., antibody mimietic, antibody or antigen-binding fragment, or polypeptide or conjugate. The secondary antibody may be any antibody of any isotype or class, provided that the secondary antibody will bind to the anti-ZIKV binding construct (e.g., antibody mimetic, antibody, antigen-binding fragment thereof), polypeptide or conjugate.

In exemplary embodiments, the binding construct (e.g., antibody mimetic, antibody or antigen-binding fragment) or polypeptide is conjugated to a solid support. In exemplary embodiments, the conjugate comprises a solid support. For example, the solid support is selected from the group consisting of a tube, a dish, a flask, a bag, a plate (e.g., a microtiter plate), a membrane, a filter, a bead, a fiber, a probe, and the like. In exemplary aspects, the solid support is made of a polymer. In exemplary aspects, the solid support is made of agarose, cellulose, dextran, polyacrylamide, latex, or controlled pore glass. In exemplary aspects, the solid support is made of agarose. In exemplary aspects, the solid support is made of polyvinyl difluoride (PVDF), nitrocellulose, nylon 66, protran nitrocellulose, or paper. In exemplary aspects, the membrane is one of the Immobilon®, Protran®, QuickDraw®, Westran®, Whatman® or Hybond® membranes (Sigma-Aldrich, St. Louis, Mo.). In exemplary aspects, the solid support is a polymer bead, a magnetic or paramagnetic bead, a microtiter plate, a membrane or a filter.

The present disclosure provides a method of detecting a Zika virus (ZIKV) infection in a subject. In exemplary embodiments, the method comprises (i) contacting a sample obtained from the subject with a binding construct (e.g., an antibody mimetic, an antibody, antigen-binding fragment), or polypeptide as described herein, thereby forming a test mixture, and (ii) assaying the test mixture for a complex comprising ZIKV bound to the binding construct or polypeptide, wherein, when the complex is present in the test mixture, the subject is determined as having a ZIKV infection. In exemplary aspects, the sample is selected from the group consisting of blood, plasma, serum, urine, semen, lacrimal fluid, saliva, or tissue fluids.

In exemplary aspects, the method of detecting a ZIKV infection in a subject comprises (i) adding a sample obtained from the subject to a solid support bound to a capture molecule that binds to ZIKV, (ii) adding a detection antibody comprising a binding construct (e.g., antibody, antigen-binding fragment, antibody mimetic) or polypeptide as described herein, (iii) adding a detection agent which binds to the detection antibody comprising a binding construct or polypeptide, and (iv) assaying for a signal from the detection agent, wherein, when the signal is detected, the subject is determined as having a ZIKV infection. In exemplary aspects, the method is carried out with a kit as described herein. In exemplary aspects, the method is a sandwich ELISA. In exemplary aspects, one or more areas of the solid support not bound to the capture molecule is bound to a blocking agent, optionally, bovine serum albumin. In exemplary aspects, the capture molecule is a lectin which binds to ZIKV. In exemplary aspects, the capture molecule is concanavalin A. In alternative aspects, the capture molecule is a binding construct (e.g., an antibody antigen-binding fragment, antibody mimetic) or polypeptide as described herein. In exemplary aspects, the capture molecule comprises the amino acid sequences of SEQ ID NOs: 8-15, optionally SEQ ID NO: 10, 13, or 15.

The present disclosure also provides a method of detecting Zika virus (ZIKV) immunity in a subject. The method in some aspects is a method of detecting ZIKV-specific antibodies made by the subject being tested, the presence of such antibodies indicating that the subject has had a previous exposure to ZIKV. Thus, the present disclosure provides a method of determining whether a subject has had a prior infection to ZIKV or a prior exposure to ZIKV. The present disclosure provides a method of detecting ZIKV antibodies in a sample obtained from a subject. In exemplary aspects, these methods comprise (i) adding a blood, plasma, or serum sample obtained from the subject to a solid support bound to a capture molecule that binds to ZIKV, (ii) adding a detection antibody comprising a binding construct (e.g., antibody mimetic, an antibody, antigen-binding fragment), or polypeptide as described herein, (iii) adding a detection agent which binds to the detection antibody comprising a binding construct or polypeptide, and (iv) assaying for a signal from the detection agent, wherein, when the signal is detected, the subject is determined as not having ZIKV immunity (or as not having a previous exposure to ZIKV or prior ZIKV infection) and, when the signal is not detected, the subject is determined as having ZIKV immunity (or as having a previous exposure to ZIKV or prior ZIKV infection).

The present disclosure also provides a method of detecting Zika virus (ZIKV) exposure in a subject. The method in some aspects is a method of detecting ZIKV-specific antibodies made by the subject being tested, the presence of such antibodies indicating that the subject has had a previous exposure to ZIKV. In exemplary aspects, the method comprises (i) adding a blood, plasma, or serum sample obtained from the subject to a solid support bound to a capture molecule that binds to ZIKV or ZIKV-derived antigens, (ii) adding a detection antibody comprising a binding construct (e.g., an antibody, antigen-binding fragment, antibody mimetic), or polypeptide as described herein, (iii) adding a detection agent which binds to the detection antibody comprising a binding construct or polypeptide, and (iv) assaying for a signal from the detection agent, wherein, when the signal is detected, the subject is determined as not having previous ZIKV exposure and, when the signal is not detected, the subject is determined as having a previous ZIKV exposure. In exemplary aspects, the method further comprises a wash step. The wash step in some aspects is after step (i), after step (ii), and/or after step (iii) of the method. In exemplary aspects, the method is carried out with a kit as described herein. In exemplary aspects, the method is a sandwich ELISA. In exemplary aspects, one or more areas of the solid support not bound to the capture molecule is bound to a blocking agent, optionally, bovine serum albumin.

In exemplary aspects, the methods further comprise a wash step. The wash step in some aspects is after the step of adding a blood, plasma, or serum sample obtained from the subject to a solid support bound to a capture molecule that binds to ZIKV, after the step of adding a detection antibody comprising a binding construct, e.g., antibody mimetic, an antibody, antigen-binding fragment, or polypeptide as described herein, or after the step of adding a detection agent which binds to the detection antibody comprising a binding construct or polypeptide, or a combination thereof. In exemplary aspects, the method is carried out with a kit as described herein. In exemplary aspects, the method is a sandwich ELISA. In exemplary aspects, one or more areas of the solid support not bound to the capture molecule is bound to a blocking agent, optionally, bovine serum albumin. In exemplary aspects, the capture molecule is a binding construct, or polypeptide as described herein. Additionally provided herein is a method of detecting a Zika virus (ZIKV) infection and ZIKV immunity in a subject. In exemplary embodiments, the method comprises adding a sample obtained from a subject to the assay system as described herein. In exemplary aspects, when the assay system exhibits a single band in Zone C, the subject is determined as having neither a ZIKV infection nor ZIKV immunity, when the assay system exhibits a band in each of Zone A and Zone B, the subject is determined as having both a ZIKV infection and ZIKV immunity, and when the assay system exhibits a band in Zone B and a band is absent in Zone A, the subject is determined as not having a ZIKV infection but having ZIKV immunity. In exemplary aspects, the sample is blood, plasma, serum, urine, semen, lacrimal fluid, saliva, or tissue fluids.

Figure 6:
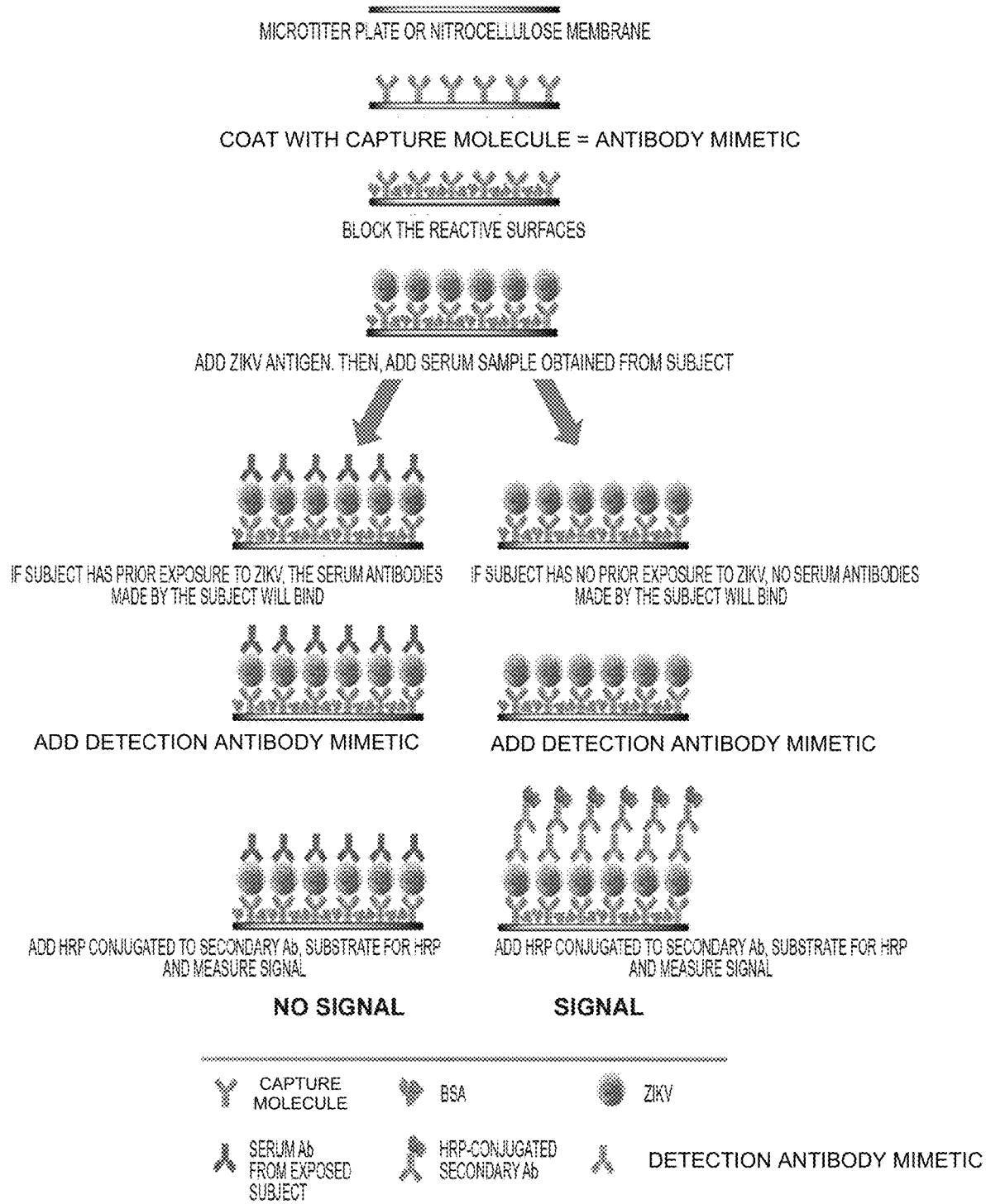
FIG. 6 represents a detection scheme for determining the presence of ZIKV-specific Abs in the sera of individuals. Sera that do not contain ZIKA specific Abs will not block binding of an antibody mimetic of the present disclosure. Only sera from individuals previously infected with ZIKV will block the antibody mimetic reactivity.
Figure 10:
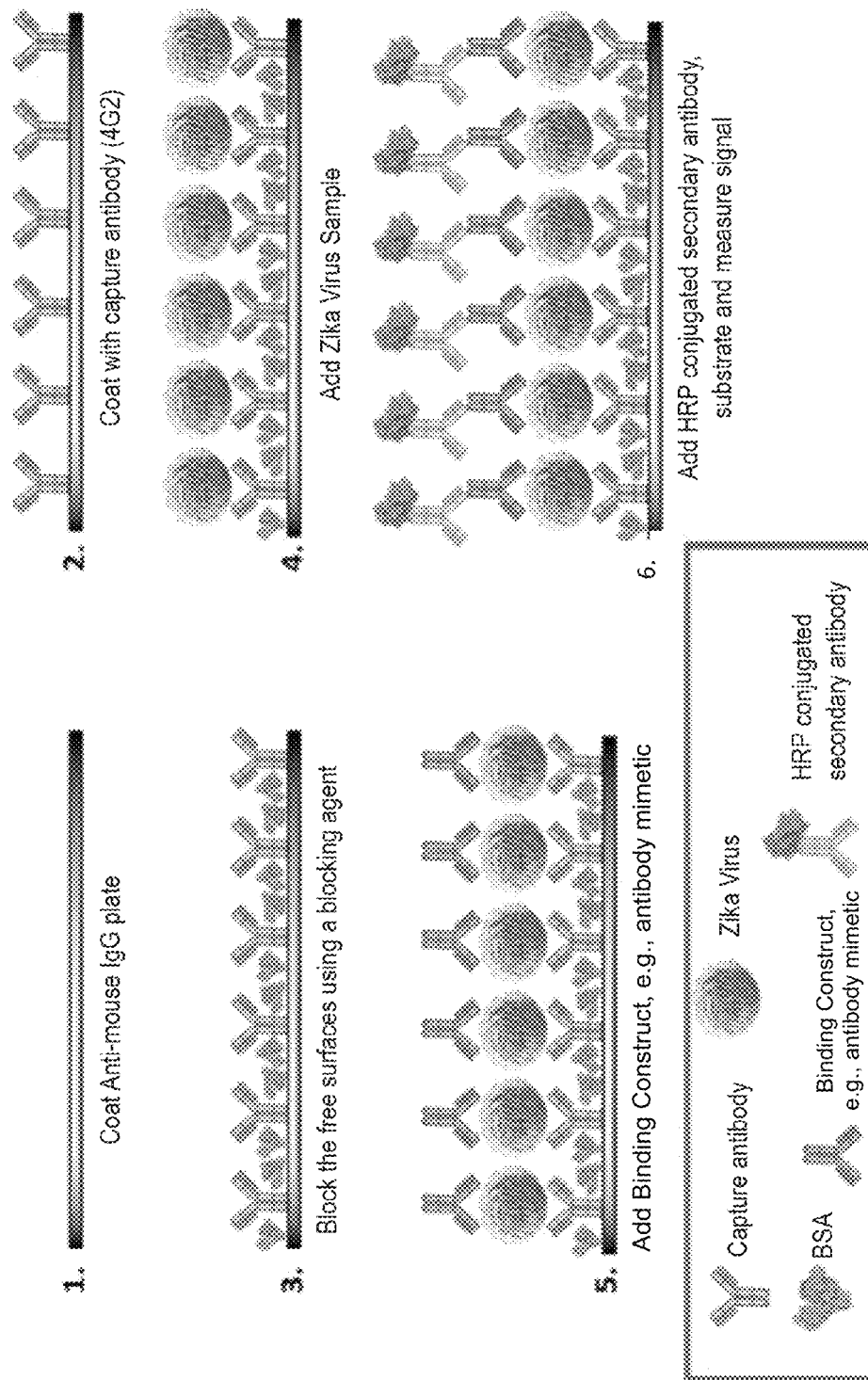
FIG. 10 is an illustration of a microtiter-based, ELISA platform diagnostic assay for the direct detection of ZIKV. Shown are the components of the assay and the detection scheme for determining the presence of ZIKV in an acute ZIKV infection.

FIGS. 6, 7, and 10 provide exemplary illustrations of the presently disclosed detection methods.

Vaccine Efficacy

The present disclosure further provides a method of assessing efficacy of a Zika virus (ZIKV) vaccine in a subject who has received a ZIKV vaccine. In exemplary aspects, the method comprises adding a sample obtained from the subject to the assay system as described herein, wherein, when the assay system exhibits (i) a band in each of Zone A and Zone B or (ii) a band in Zone B and a band is absent in Zone A, the ZIKV vaccine is determined as effective in the subject, and when the assay system exhibits a single band in Zone C, the ZIKV vaccine is determined as ineffective in the subject. In exemplary aspects, the method comprises (i) adding a blood, plasma, or serum sample obtained from the subject to a solid support bound to a capture molecule that binds to ZIKV, (ii) adding a detection antibody comprising a binding construct (e.g., antibody mimetic, an antibody, antigen-binding fragment), or polypeptide described herein, (iii) adding a detection agent which binds to the detection antibody comprising a binding construct or polypeptide, and (iv) assaying for a signal from the detection agent, wherein, when the signal is detected, the vaccine is determined as ineffective in the subject, and, when the signal is not detected, the vaccine is determined as effective in the subject.

In such methods of the present disclosure, the binding construct is a clamp peptide in exemplary aspects. In exemplary aspects, the clamp peptide comprises a sequence of any one of SEQ ID NOs: 16-23 and a sequence of any one of SEQ ID NOs: 24-31. In exemplary aspects, the clamp peptide comprises a sequence of any one of SEQ ID NOs: 16-23 and a sequence of any one of SEQ ID NOs: 24-31 and an additional sequence of, e.g., intervening amino acids or amino acid sequences or a bridge peptide. In exemplary aspects, the clamp peptide comprises a pair of amino acid sequences comprising SEQ ID NOs: 16 and 24 or SEQ ID NOs: 16 and 25 or SEQ ID NOs: 18 and 26 or SEQ ID NOs: 18 and 27 or SEQ ID NOs: 20 and 24 or SEQ ID NOs: 20 and 25 or SEQ ID NOs: 22 and 26 or SEQ ID NOs: 22 and 27. In some aspects, the clamp peptide comprises a pair of amino acid sequences comprising SEQ ID NOs: 18 and 26. In some aspects, the clamp peptide comprises a pair of amino acid sequences comprising SEQ ID NOs: 20 and 25. In some aspects, the clamp peptide comprises a pair of amino acid sequences comprising SEQ ID NOs: 22 and 26. In exemplary aspects, the clamp peptide comprises a bridge peptide that joins one sequence to the other. Optionally, the bridge peptide comprises SEQ ID NO: 32. In various aspects, the clamp peptide comprises the sequence of any one of SEQ ID NOs: 8-15. In some aspects, the clamp peptide comprises the sequence of SEQ ID NO: 10. In some aspects, the clamp peptide comprises the sequence of SEQ ID NO: 13. In some aspects, the clamp peptide comprises the sequence of SEQ ID NO: 14.

Pharmaceutical Compositions and Routes of Administration

In exemplary embodiments, the binding constructs (e.g., an antibody or antigen-binding fragment, antibody mimetic), polypeptides, nucleic acids, expression vectors, host cells, and conjugates of the present disclosure are provided as part of a composition. Accordingly, the present disclosure provides a composition comprising any one or more of the binding constructs (e.g., an antibody or antigen-binding fragment, antibody mimetic), polypeptides, nucleic acids, expression vectors, host cells, and conjugates of the present disclosure, or a combination thereof. In accordance with some embodiments, the composition is a pharmaceutical composition comprising any one or more of the binding constructs (e.g., an antibody or antigen-binding fragment, antibody mimetic), polypeptides, nucleic acids, expression vectors, host cells, and conjugates of the present disclosure, or a combination thereof, and a pharmaceutically acceptable carrier, diluent, or excipient.

The pharmaceutical compositions may be formulated to achieve a physiologically compatible pH. In some embodiments, the pH of the pharmaceutical composition may be at least 5, at least 5.5, at least 6, at least 6.5, at least 7, at least 7.5, at least 8, at least 8.5, at least 9, at least 9.5, at least 10, or at least 10.5 up to and including pH 11, depending on the formulation and route of administration, for example between 4 and 7, or 4.5 and 5.5. In illustrative embodiments, the pharmaceutical compositions may comprise buffering agents to achieve a physiological compatible pH. The buffering agents may include any compounds capable of buffering at the desired pH such as, for example, phosphate buffers (e.g., PBS), triethanolamine, Tris, bicine, TAPS, tricine, HEPES, TES, MOPS, PIPES, cacodylate, MES, acetate, citrate, succinate, histidine or other pharmaceutically acceptable buffers.

In various embodiments, the physiologically and pharmaceutically acceptable carrier can include any of the well-known components useful for immunization. The carrier can facilitate or enhance an immune response to an antigen administered in a vaccine. The cell formulations can contain buffers to maintain a preferred pH range, salts or other components that present an antigen to an individual in a composition that stimulates an immune response to the antigen. The physiologically acceptable carrier also can contain one or more adjuvants that enhance the immune response to an antigen. Pharmaceutically acceptable carriers include, for example, pharmaceutically acceptable solvents, suspending agents, or any other pharmacologically inert vehicles for delivering compounds to a subject. Pharmaceutically acceptable carriers can be liquid or solid, and can be selected with the planned manner of administration in mind so as to provide for the desired bulk, consistency, and other pertinent transport and chemical properties, when combined with one or more therapeutic compounds and any other components of a given pharmaceutical composition. Typical pharmaceutically acceptable carriers include, without limitation: water, saline solution, binding agents (e.g., polyvinylpyrrolidone or hydroxypropyl methylcellulose); fillers (e.g., lactose or dextrose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate). Compositions can be formulated for subcutaneous, intramuscular, or intradermal administration, or in any manner acceptable for administration.

An adjuvant refers to a substance which, when added to an immunogenic agent such as a cell containing the expression vector system of the invention, nonspecifically enhances or potentiates an immune response to the agent in the recipient host upon exposure to the mixture. Adjuvants can include, for example, oil-in-water emulsions, water-in oil emulsions, alum (aluminum salts), liposomes and microparticles, such as, polysytrene, starch, polyphosphazene and polylactide/polyglycosides.

Adjuvants can also include, for example, squalene mixtures (SAF-I), muramyl peptide, saponin derivatives, *mycobacterium* cell wall preparations, monophosphoryl lipid A, mycolic acid derivatives, nonionic block copolymer surfactants, Quil A, cholera toxin B subunit, polyphosphazene and derivatives, and immunostimulating complexes (ISCOMs) such as those described by Takahashi et al., Nature 1990, 344:873-875. For veterinary use and for production of antibodies in animals, mitogenic components of Freund's adjuvant (both complete and incomplete) can be used. In humans, Incomplete Freund's Adjuvant (IFA) is a useful adjuvant. Various appropriate adjuvants are well known in the art (see, for example, Warren and Chedid, CRC Critical Reviews in Immunology 1988, 8:83; and Allison and Byars, in Vaccines: New Approaches to Immunological Problems, 1992, Ellis, ed., Butterworth-Heinemann, Boston). Additional adjuvants include, for example, bacille Calmett-Guerin (BCG), DETOX (containing cell wall skeleton of *Mycobacterium phlei* (CWS) and monophosphoryl lipid A from *Salmonella minnesota* (MPL)), and the like (see, for example, Hoover et al., J Clin Oncol 1993, 11:390; and Woodlock et al., J Immunother 1999, 22:251-259).

In exemplary aspects, the pharmaceutical compositions may be formulated for administration to the subject via parenteral, intravenous, intramuscular, subcutaneous, sublingual, nasal, inhalation, vaginal, rectal, oral, or topical administration. In exemplary aspects, the pharmaceutical compositions is formulated for parenteral administration. Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The term, "parenteral" means not through the alimentary canal but by some other route such as subcutaneous, intramuscular, intraspinal, or intravenous. The analog of the present disclosure can be administered with a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

The parenteral formulations will typically contain from about 0.5% to about 25% by weight of the analog of the present disclosure in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Injectable formulations are in accordance with the invention. The requirements for effective pharmaceutical carriers for injectable compositions are well-known to those of ordinary skill in the art (see, e.g., *Pharmaceutics and Pharmacy Practice,* J. B. Lippincott Company, Philadelphia, Pa., Banker and Chalmers, eds., pages 238-250 (1982), and *ASHP Handbook on Injectable Drugs,* Toissel, 4th ed., pages 622-630 (1986)).

When the pharmaceutical composition comprises cells, the pharmaceutical composition may be administered to the subject through any suitable method known in the art, including, for example, perfusions, infusions and injections. See, e.g., Burch et al., *Clin Cancer Res* 6(6): 2175-2182 (2000), Dudley et al., *J Clin Oncol* 26(32): 5233-5239 (2008); Khan et al., *Cell Transplant* 19:409-418 (2010); Gridelli et al., *Liver Transpl* 18:226-237 (2012)).

Therapeutic Methods

Because some of the binding constructs of the present disclosure are neutralizing antibodies, the present disclosure provides methods of treating a ZIKV infection in a subject. In exemplary aspects, the method comprises administering to the subject a binding construct (e.g., an antibody or antigen-binding fragment thereof, antibody mimetic) in, e.g., an amount to treat or prevent the ZIKV injection in the subject.

As used herein, the term "treat," as well as words related thereto, do not necessarily imply 100% or complete treatment. Rather, there are varying degrees of treatment of which one of ordinary skill in the art recognizes as having a potential benefit or therapeutic effect. In this respect, the methods of treating a ZIKV infection of the present disclosure can provide any amount or any level of treatment. Furthermore, the treatment provided by the method of the present disclosure may include treatment of one or more conditions or symptoms or signs of the infection, being treated. Also, the treatment provided by the methods of the present disclosure may encompass slowing the progression of the infection. For example, the methods can treat the infection by virtue of eliciting an immune response against ZIKV, stimulating or activating CD8+ T cells specific for ZIKV to proliferate, stimulating or activating the classical complement pathway, and the like.

As used herein, the term "prevent" and words stemming therefrom encompasses inhibiting or otherwise blocking infection by ZIKV. As used herein, the term "inhibit" and words stemming therefrom may not be a 100% or complete inhibition or abrogation. Rather, there are varying degrees of inhibition of which one of ordinary skill in the art recognizes as having a potential benefit or therapeutic effect. In this respect, the presently disclosed expression vector systems or host cells may inhibit ZIKV infection to any amount or level. In illustrative embodiments, the inhibition provided by the methods of the present disclosure is at least or about a 10% inhibition (e.g., at least or about a 20% inhibition, at least or about a 30% inhibition, at least or about a 40% inhibition, at least or about a 50% inhibition, at least or about a 60% inhibition, at least or about a 70% inhibition, at least or about a 80% inhibition, at least or about a 90% inhibition, at least or about a 95% inhibition, at least or about a 98% inhibition).

In various embodiments, methods of the disclosure prevent, alleviate, and/or treat one or more symptoms associated with ZIKV infection. Illustrative symptoms that may be treated include, but are not limited to fever, rash (e.g., skin rash), muscle and/or joint pain, swollen joints, malaise, headache, conjunctivitis (red eyes), post-infection asthenia, digestive problems including abdominal pain, diarrhea, constipation, mucous membrane ulcerations (aphthae), pruritus, meningoencephalitis, and Guillain-Barre syndrome.

In various embodiments, methods of the present disclosure may prevent, alleviate, and/or treat one or more symptoms associated with ZIKV infection in pregnant women including those symptoms described above. Additionally, methods of the disclosure may prevent spontaneous abortions in pregnant women.

Subjects

In exemplary embodiments, the subject referenced herein is a mammal, including, but not limited to, mammals of the order Rodentia, such as mice and hamsters, and mammals of the order Logomorpha, such as rabbits, mammals from the order Carnivora, including Felines (cats) and Canines (dogs), mammals from the order Artiodactyla, including Bovines (cows) and Swines (pigs) or of the order Perssodactyla, including Equines (horses). In some aspects, the mammals are of the order Primates, Ceboids, or Simoids (monkeys) or of the order Anthropoids (humans and apes).

In various embodiments, the mammal is a human. In some embodiments, the human is an adult aged 18 years or older. In some embodiments, the human is a child aged 17 years or less. In an embodiment, the subject is male, e.g., a male human. In another embodiment, the subject is a female subject. In illustrative embodiments, the subject is a female subject, e.g., a female human, aged from about 16 years to about 50 years. In illustrative embodiments, the female human is capable of giving birth. In illustrative embodiments, the subject is a pregnant female. In illustrative embodiments, the human pregnant female is in the first trimester, second trimester, or third trimester of pregnancy. In illustrative embodiments, the subject is not pregnant. In various embodiments, the subject is an embryo or a fetus including an unborn embryo or fetus. As referred to herein, an embryo is developed from the time of fertilization until the end of the eighth week of gestation, at which time it is referred to as a fetus. In exemplary aspects, the female human is pregnant or is considering whether or not to become pregnant.

Samples

In exemplary embodiments, the sample referenced herein is a biological sample comprising one or more bodily fluids, e.g., human bodily fluids. In exemplary aspects, the sample comprises a bodily fluid, including, but not limited to, blood, plasma, serum, lymph, breast milk, saliva, mucous, semen, vaginal secretions, cellular extracts, inflammatory fluids, cerebrospinal fluid, feces, vitreous humor, or urine obtained from the subject. In exemplary aspects, the sample is blood, plasma, serum, urine, semen, lacrimal fluid, saliva, or tissue fluids. In exemplary aspects, the sample comprises blood, plasma, serum, urine, cerebrospinal fluid, or saliva. In exemplary aspects, the sample comprises or is prepared from blood, plasma, or serum.

In exemplary aspects, the sample comprises or is prepared from blood, plasma, or serum and the sample further comprises one or more of: hemoglobin, bilirubin, cholesterol, rheumatoid factor, humanized anti-mouse antibodies (HAMA), and albumin. In exemplary instances, the sample comprises (i) hemoglobin or albumin at a concentration of at least about 75 mg/mL, about 125 mg/mL, or about 250 mg/mL, (ii) cholesterol at a concentration of at least about 2.5 mg/mL, about 5 mg/mL, or about 10 mg/mL, (iii) bilirubin or HAMA at a concentration of about 0.25 mg/mL, about 0.5 mg/mL, or about 1.0 mg/mL, (iv) or a combination thereof.

Alternatively or additionally, the sample comprises at least one infectious agent other than ZIKV. In some instances, the sample comprises one or more of: cytomegalovirus, Epstein-Barr virus, Parvovirus B19, varicella zoster virus, *Plasmodium falciparum*, chikungunya virus, Dengue virus, yellow fever virus, west nile virus, rheumatoid factor, Japanese encephalitis virus, St. Louis encephalitis virus, or antibody nuclear antibody (ANA).

The following examples are given merely to illustrate the present invention and not in any way to limit its scope.

EXAMPLES

Example 1

This example describes an exemplary method of designing clamp peptides, a new generation of antibody mimetics.

Abstract

A new class of antibody mimetics is proposed. This is a generic universal approach that can be used against any type of antigen. The antibody mimetics were designed connecting three short peptides mimicking a clamp with two arms and one bridge.

The peptide arms were computationally designed using a virtual approach based on generating different docking cycles of tetra, penta, hexapeptide libraries by maximizing the recognition properties of amino acid motifs between the ZIKV envelope protein active sites and other flaviviruses binding sites (DENV, Chikungunya and West Nile).

The peptide bridge, connecting the two arms, was made with glycine for spacing, proline for bending and two cysteines for biotin functionalization.

Eight clamp peptides and four mono arm peptides were then synthesized and tested vs intact ZIKV particles by using a direct enzyme linked immunosorbent assay (ELISA). As a reference, we employed a well-established anti-ZIKV virus antibody, the antibody 4G2.

Three clamp peptides assay showed a detection limit one or two order of magnitude lower (around $3.16*10^3$ [ZIKV] copies/mL) then the antibody or mono-arm peptides with a dynamic range from $10^4$ to $10^7$ copies/mL of intact ZIKV particles. Synthetic clamp peptides showed low coefficient of variation (<5%) and a good inter-day and batch to batch reproducibility (<15%). These three clamp peptides showed slight cross-reactivity against three serotypes of DENV (DENV-1, -2 and -3) at the concentration of $10^5$ copies/mL of intact virus particles, but the discrimination between the DENV and ZIKV was lost increasing the coating concentration to $10^6$ copies/mL of the viruses.

The sensitivity of the clamp peptides was tested in the presence of two biological matrices, urine and serum diluted 1:1 and 1:10, respectively. The detection limits of clamp peptides decreased about one order of magnitude for ZIKV detection in urine or serum, with a distinct analytical signal starting from $10^5$ copies/mL of ZIKV.

Introduction

The threat of ZIKV infection has emerged as a global public health problem because of its ability to cause severe congenital disease and affect a large population (Ioos et al., 2014; Weaver et al., 2016). ZIKV infection is known to cause neurological problems to pregnant women and potentially cause microcephaly and other congenital malformations and diseases to the unborn child. ZIKV affects, both male and females and it has been reported that the virus can be transmitted sexually through semen and vaginal fluids. The ZIKV virus is a mosquito-borne flavivirus, and due to the lack of specific antibodies/binders that can be used for diagnosis of the disease, the current bioassays present cross-reactivity with other flaviviruses and arboviruses. It is well established that ZIKV has many common genetic sequences and protein structures with other flaviviruses, like DENV, West Nile virus or Chikungunya (Barba-Spaeth et al., 2016; Heffron et al., 2018). This limits the use of immunoassays for the detection of human pathogens within the flavivirus genus (Priyamvada et al., 2016; Stettler et al., 2016). Thus, there is a need for highly selective binders for ZIKV that can be employed in diagnostics and health status assessment of patients suffering from ZIKV.

The flavivirus envelope protein is responsible for virus entry and represents a major target for neutralizing antibodies. The ZIKV virus structure is similar to other known flaviviruses structures except for the ~10 amino acids that surround the Asn-154 glycosylation site found in each of the 180 envelope glycoproteins that make up the icosahedral shell (Zhao et al., 2016).

In this work, the clamp peptide arms were designed using as guide the crystallographic coordinates of the ZIKV envelope protein glycosylation binding site. The entire molecular surface of the glycosylation envelope protein biding site was defined by two cubic boxes where arm peptides were expected to bind.

The in-silico screening technique was based on a semi-combinatorial approach by designing peptides that could wrap around the glycosylation site such as to clamp the peptide in place. Different docking cycles of peptide libraries were generated by maximizing the recognition properties of the amino acid motif between the ZKV glycosylation site and the other flaviviruses glycosylation binding sites (DENV, Chikungunya and West Nile). A total library of around three million peptides was tested in-silico.

Peptides as antibody mimetic elements in diagnostic methods were recently reviewed highlighting the features desired to outperform antibodies with regard to binding affinities, cellular and tumor penetration, large-scale production, temperature, and pH stability (Yu et al., 2017). It is well documented that a hard chemical environment can affect antibodies binding properties and DNA and peptides aptamers are the most promising candidates to replace them in bioanalysis as reported by recent reviews (Gong et al., 2010; Pichon et al., 2015; Li et al., 2018). Aptamers have become increasingly important molecular tools for diagnostics and as therapeutic agents, and are used in many analytical applications, such as chromatography, electrophoresis, mass spectrometry, molecular beacons, gas sensors, and biosensors (Stobiecka and Chatupa, 2015; Lin et al., 2016; Tang et al., 2016; Mascini et al., 2017; Mascini et al., 2019).

In recent works, short peptides were used as molecular binders for virus detection. Linear peptides were selected by phage display to detect norovirus using an ELISA protocol or by means of an impedance biosensor (Hwang et al., 2017; Palzkill et al., 2018).

Computationally designed peptides were used to possibly detect flavivirus. Binding affinity and stability of disulfide cyclic peptide ligands with target DENV E glycoprotein were calculated by molecular docking and molecular dynamics simulation, but no experimental evidence was provided (Tambunan et al., 2016).

A recent report predicted by molecular docking the structure of short peptides targeting the ZIKV envelope protein and the interactions between the selected peptides and virus were assessed via a fluorescence-linked sandwich immunosorbent assay (FLISA), and the performance of the peptide-linked sandwich FLISA was evaluated in virus-spiked human serum and urine (Do Thi Hoang Kim et al., 2018).

Molecular modelling is more and more used to overcome the trial and error approach and to minimize experimental problems by providing an understanding of atomic interactions and facilitating the rational design of experimental protocols (Acebes et al., 2016; Bunker et al., 2016; Singh et al., 2016; Michaeli et al., 2018; Xu et al., 2018). Virtual docking is currently an important tool in drug discovery, and a subject of important developments over the last decade (Macalino et al., 2015; Yuan et al., 2017).

However, a number of obstacles still limits the widespread use of molecular modelling for biotechnological applications. One of the most important drawbacks for mainstream use of molecular modeling is the challenge to simulate a huge number of candidates to be designed or/and docked using a full combinatorial approach.

To address this issue, herein we present a new methodology, based on an incremental construction approach to choose short peptides as binding agents for the selective detection of the intact ZIKV particles. Synthetic peptides are more resistant to physicochemical stress, more reproducible and less expensive when compared with antibodies so even if they show less specificity can be used as an array giving synergetic contribution to the detection.

Direct ELISA was chosen as the experimental protocol to check the performances of the clamp peptides. ELISA was preferred to other analytical techniques because it provides automated steps to speed-up the screening of a large number of experimental trials.

Materials and Methods

All calculations of molecular docking were done using a desktop computer with 19 processors Intel Xeon X5690 at 3.47 GHz each, with 94.5 GiB RAM, running Kernel Linux 2.6.32-642.1.1|e6.x86_64, GNOME 2.28.2.

The three peptide libraries were designed and cleaned up with Hyperchem 8.0.5.

Peptides were designed in zwitterionic mode, using only the 20 natural amino acids, adding hydrogens, using molecular mechanics method amber, with the algorithm "Steepest Descents" converging at 0.08 Kj mol-1 in 32767 as maximum of cycles. Minimization, conformers generation and docking were carried out using OpenEye Scientific Software package under academic license. Each peptide library was compacted in a single file and fast minimized in gas phase to reduce computing time. In this context, solvent condition did not change significantly the results. The energy minimization process was carried out using SZYBKI 1.5.7 in its default parameterization (SZYBKI, version 1.5.7). To take into account the flexibility of the peptides, ten conformers were generated for each peptide by means of the OMEGA 2.4.6 used with MMFF as the force field (Hawkins et al., 2010; Hawkins and Nicholls, 2012; OMEGA, version 2.4.6). Therefore, the ligands were represented by the peptide conformers, around 5 millions units.

Then the envelope proteins, taken as the receptors, were downloaded from the protein data bank web site. The envelope proteins were from the flavivirus species ZIKV DENV, Chikungunya and West Nile having respectively the following codes in the Protein Data Bank web site: 5IRE, 4UTC, 3N40 and 3I50. All residues and water molecules were removed from the envelope proteins pdb files. For each envelope protein two dedicated boxes were generated, one enfolding the glycosylation site the other in the closet cavity from the glycosylation site.

In order to reduce the calculation time, tetra and penta-peptide libraries were docked using active site boxes with a volume of around 13 nm3 and hexapeptide libraries using boxes having a volume of around 18 nm3.

Using these sizes, the entire molecular surface of all peptide conformers was inside the active site box.

The active site box along with the Multi-conformer rigid body docking were carried out using OEDocking 3.0.0 (Kelley et al., 2015; OEDocking, version 3.0.0). Multi-conformer rigid body docking was run using Chemgauss4 as scoring function. The Chemgauss4, a modification of the Chemgauss3, was the latest scoring function from OpenEye software with improved hydrogen bonding and metal chelator functions. The total score obtained was the sum of steric, acceptor/metal, donor and aromatic contributions. The time required for docking a peptide library was about 24 hours.

Structures visualization and generation of molecular surfaces were performed using VIDA 4.1.1 (VIDA, version 4.1.1).

The entire process was automated using a bash script and using a freeware BASIC-like scripting language (AutoIT V3) for post processing data analysis.

Experimental Setup

All chemicals used for buffers were of analytical grade and purchased from Sigma-Aldrich (www.sigmaaldrich.com).

The eight clamp peptides and the four mono-arm peptides were purchased from Biomatik (www.biomatik.com). Cysteines within the peptide structures were used to bind maleimide-PEG2-biotin. All peptides were provided with a purity >85%.

Lyophilized peptides were diluted at 1 mM concentration in 10 mM phosphate buffered saline (PBS) pH 7.4, divided into 100 µL aliquots and stored at −30° C. for further use.

Before biotin functionalization, peptides stock solution was reduced using trialkylphosphine (TCEP) from ThermoFisher Scientific (www.thermofisher.com) and after 1 h the gel was removed using TCEP gel spin separation columns (ThermoFisher Scientific). Then, 2-fold molar excess of EZ-Link™ Maleimide-PEG2-Biotin (ThermoFisher Scientific) was added to purified peptide solution and incubated for 1 h. At this concentration EZ-Link™ Maleimide-PEG2-Biotin did not contribute to background signal as shown by a pilot test using only EZ-Link™ Maleimide-PEG2-Biotin without peptide. Therefore, no further separation was carried out.

To optimize all parameters of the direct ELISA protocol, Pierce 96-Well Polystyrene Plates, (ThermoFisher Scientific) were coated overnight at 4° C. with different concentrations of intact virus particles (ZIKV or DENV). The intact virus particles were diluted using 100 mM NaHCO3, pH 9.6, and aliquots of 100 μL were dispensed into each well of the plate using a multichannel pipette. This buffer pH assured a strong hydrophobic binding interaction between polystyrene and virus particles.

Intact particles both ZIKV and DENV were provided by Dr. Watkins group (University of Miami, Dep. of Pathology). The samples were controlled and counted by focus forming assay and RT-PCR, the details were reported in a previous work (Magnani et al., 2017). The Intact particles of ZIKV were inactivated using gamma irradiation. Assay biohazardous steps were carried out according to standard safety procedures.

After coating the plates overnight, the intact virus particles were removed by washing five times with the washing buffer (PBST) 10 mM PBS pH 7.4, 0.1% Tween-20, using an automated plate washer (MultiWash+, Molecular Devices, Sunnyvale, Calif.). Then, the plates were blocked with 200 μL of blocking buffers while shaking at 300 rpm at room temperature. The blocking buffers used were: Pierce™ Protein-Free (PBS) Blocking Buffer (PF), Blocker™ BLOTTO in TBS, SuperBlock™ Blocking Buffer, Blocker™ BSA (1×) in PBS. All blocking buffer were from ThermoFisher Scientific.

After 2 h the blocking buffers were removed using the same washing procedure mentioned above. 100 μL-aliquots of several dilutions of peptides biotinylated in 10 mM PBS pH 7.4 were placed in each well and incubated for 2 h while shaking at 300 rpm at room temperature. After the incubation, the unreacted peptides were removed by using the plate washer with the same settings. Then, 100 μL-aliquots of streptavidin-HRP (ThermoFisher Scientific) at a concentration of 20 ng/mL were added into each well and incubated for 30 min at room temperature without shaking. After the incubation, excess streptavidin-HRP was removed and the wells were washed with the plate washer five times using the washing buffer. Finally, 100 μL-aliquots of the Ultra TMB-ELISA Substrate Solution (ThermoFisher Scientific) were added and after 10 min the reaction was stopped by adding 100 μL aliquots of the TMB stop solution (SeraCare). The emission (450 nm) was read using a microplate reader (Clariostar Optima; BMG Labtech, Ortenberg, Germany).

The corresponding blank signals in triplicates were obtained by using all reagents without peptides. The blank signal was then subtracted to the average absorbance values for triplicate wells of each test.

All Data were processed and fitted using the software XLSTAT Version 2016.02.28451.

Results and Discussion

Docking Simulation

The envelope protein, responsible for virus entry, has very similar structure in all flavivirus. ZIKV differs from other known flavivirus by only ~10 amino acids that surround the Asn154 glycosylation site found in each of the 180 envelope glycoproteins (Sirohi et al., 2016).

Figure 1A:
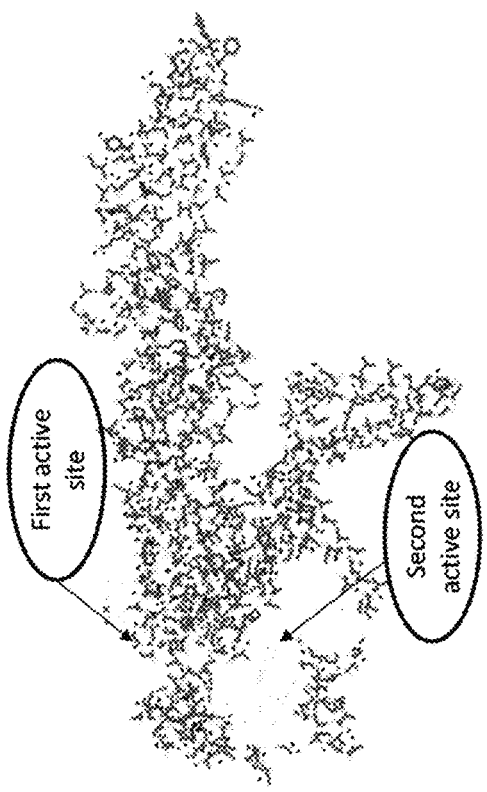
FIG. 1A is a computer-generated illustration of the target protein (Zika envelope protein) and the two active sites chosen for docking the peptide libraries. The larger blue shapes represent the electrostatic surfaces of the active sites.

As depicted by FIG. 1A the two arms of the clamp peptide were docked in two different envelope protein binding sites. The first active site box, defining the general space of the protein where peptides are expected to bind, was designed around the amino acid Asn 154 in the 5IRE and the amino acids Asn 153, Asn 140 and Asn 134 respectively in the 4UTC, 3N40 and 3I50. The Second active site box was built inside the closest cavity from the first active site, around the amino acid His 323 in the 5IRE and the amino acids Val 354, His 331 and His 285 respectively in the 4UTC, 3N40 and 3I50.

Figure 1D:
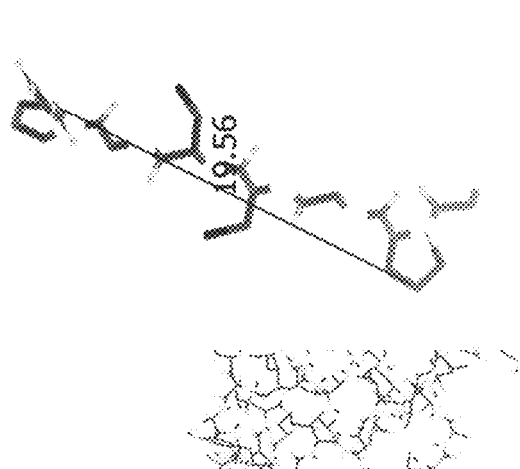
FIG. 1D is a computer-generated illustration of a bridge peptide designed and minimized in zwitterionic mode. The bridge peptide comprises eight amino acids long and has the amino acid sequence GPGCCGPG (SEQ ID NO: 32). The length in angstrom is shown (19.56 Å=1.956 nm).
Figure 1C:
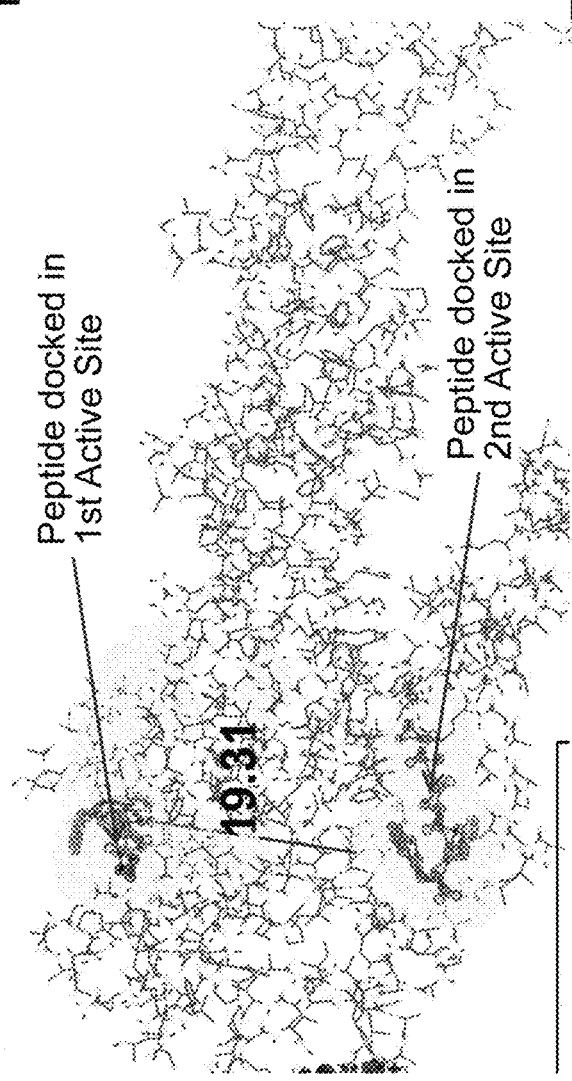
FIG. 1C is a computer-generated illustration of the target protein of FIG. 1A with two peptides (outlined in orange) docked in the two active sites. The larger blue shaded regions represent the electrostatic surfaces of the active sites. The length (in angstrom) between the two docked peptides is shown (19.31 Å or 1.931 nm) in yellow.

FIG. 1B showed the schematic representation of the clamp peptide structure made by two peptide arms of five or six amino acids in length linked by a bridge peptide having as sequence GPGCCGPG (SEQ ID NO: 32). The length in angstrom (1.931 nm) between two peptides docked in the two active sites chosen within the envelope protein was also calculated (FIG. 1C) in order to have an idea of the length needed to link the two arm peptides with a bridge peptide. The bridge peptide chosen (GPGCCGPG; SEQ ID NO: 32) had a length after minimization of 1.956 nm (FIG. 1D), approximately the distance between the two arm peptides. Using this bridge peptide size, the two arms of the clamp peptide should have enough flexibility to bind each of the two active site in synergic combination.

In order to avoid any disulfide bond between the two arms of the clamp peptide, the peptides having sulfur-containing amino acids (cysteine and methionine) were discarded during the semi-combinatorial peptide libraries screening.

The docking process was run in 3 steps. In each step a peptide library was generated by using an incremental construction approach. In every subsequent iteration, a focused library of peptides of increasing complexity, was built on previous iteration results. The first peptide library docked was made by the entire 160 k possible tetrapeptide combinations of the 20 natural amino acids.

The docking program used in this work was based on multi-conformer rigid body docking, therefore ten conformers per peptide were generated to ensure a good compromise between calculation time and accuracy of the output data for this type of ligands (Perez et al., 2013).

From the 5% peptides (8 k tetrapeptides) having the best biding score for each of the two ZIKV binding sites, only 1 k tetrapeptides were selected for the next step.

Figure 2A:
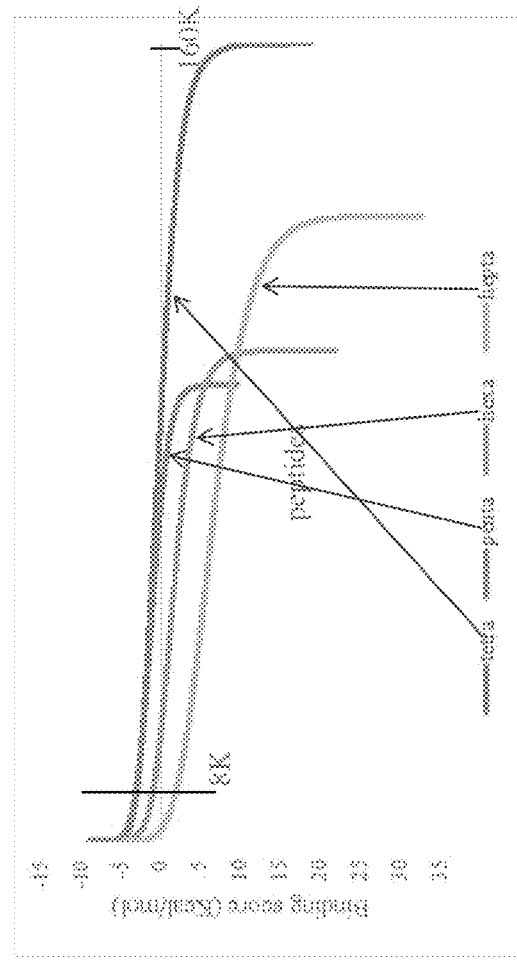
FIG. 2A is a graph of the binding score (kcal/mol) of the three peptides libraries (first library of tetrapeptides (blue); second peptide library of pentapeptides (orange); third peptide library of hexapeptides (gray)) docked in the active site 1 (Asn154), showing the typical distribution of scores obtained in the simulations. The binding score data were sorted in ascending order of binding score, thus not necessarily a correspondence must exist between the positions of the peptides in each curve.

The criterion of the selection was to choose the peptides inside the top 5% peptides binding the ZIKV active site and concurrently outside the top 5% peptides binding the other flaviviruses binding sites. The meaning of the selection was to maximize the recognition properties of the amino acid motif between the ZIKV binding site and the other flaviviruses binding sites (DENV, West Nile and Chikungunya). The 5% was selected as cutoff because in all simulations, this value delimited the zone of the curve in which the steeper slope change was observed (FIG. 2A).

This criterion was applied to the other steps to select penta, hexa and heptapeptides. FIG. 2A depicted the typical distributions of scores obtained in the simulations. The curves obtained had similar gaussian distributions. Score values comprised within the range from 20 to −10 kcal/mol in all simulations. All docking runs had approximately 5% of the complexes with higher scores and 5% with worse scores, both well separated from the rest of the population.

The score values were calculated using chemgauss4 scoring function and, thus, lower values represented higher protein-peptide affinity.

Figure 2B:
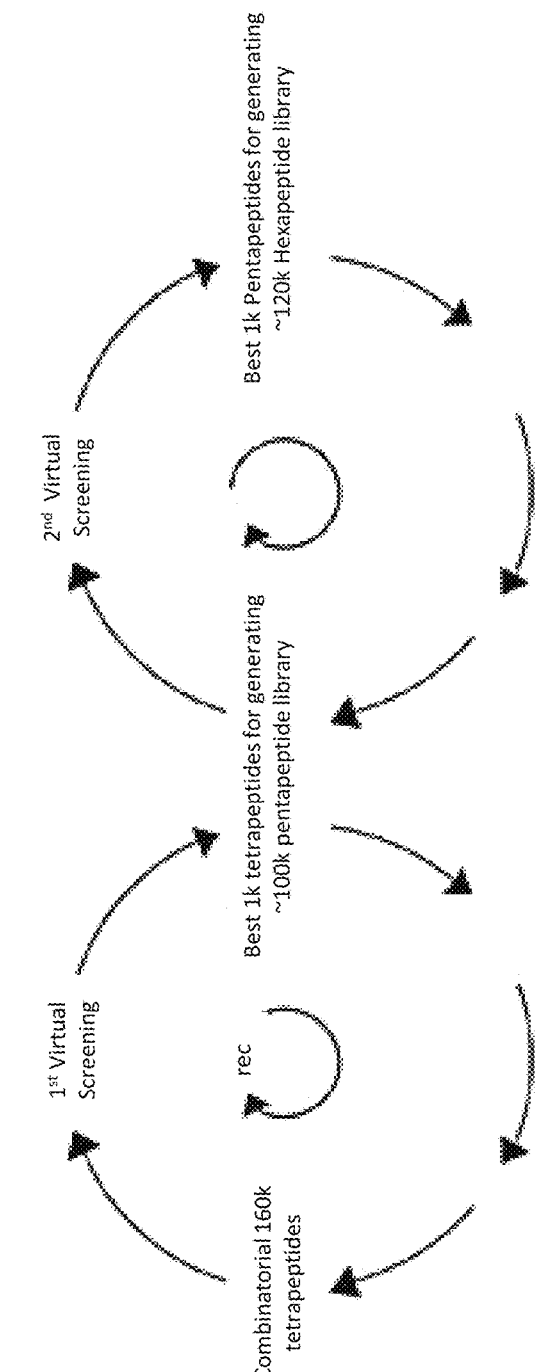
FIG. 2B is a schematic representation of the semi-combinatorial approach for obtaining penta- and hexapeptide libraries. The semi-combinatorial approach is based on generating different cycles of peptide libraries by maximizing the recognition properties of amino acid motif between the Zika binding site and the other flaviviruses binding sites.

The second step was the generation of the pentapeptide library by inserting each of the 20 natural amino acids in every position of the 1 k tetrapeptides selected in the previous step. As reported in FIG. 2B, the hexapeptide library was built by using the same semi-combinatorial approach carried out in the first step but selecting the best 1 k pentapeptides. A total of 380 k peptides were docked in each active site box.

Table 1 reports the statistical summary of the binding scores calculated for the three libraries of peptides towards the ZIKV envelope protein. The score values were calculated using chemgauss4 scoring function and, thus, lower values represented higher protein-peptide affinity. The peptide size played a critical role for the active site 1 interaction, with lower values decreasing drastically from pentapeptides to hexapeptides, but not for active site 2.

TABLE 1

|  | active site 1 | Active site 2 |
| --- | --- | --- |
| Tetrapeptides | | |
| min | −7.5 | −7.0 |
| max | 16.5 | 6.3 |
| Av | 0.1 | −2.2 |
| median | −0.2 | −2.2 |
| Pentapeptides | | |
| min | −9.0 | −7.0 |
| max | 9.6 | 8.1 |
| Av | −1.0 | −0.8 |
| median | −1.1 | −0.9 |
| Hexapeptides | | |
| min | −5.8 | −7.9 |
| max | 21.8 | 26.8 |
| Av | 1.9 | 2.5 |
| median | 1.6 | 2.2 |

Statistical parameters of the scores behavior (Kcal/mol), obtained using the three peptide libraries docked in the active site 1 (glycosylation binding site) and the active site 2 of the 5IRE ZIKV envelope protein.

These results could be explained considering the steric effects of the peptides within the glycosylation binding pocket. Also, the minimum-maximum dynamic range among the peptide libraries reflected that this behavior becomes relevant for hexapeptides. On the other hand, all peptide libraries showed average and median very close to each other, demonstrating a good symmetry in normal distribution.

It should be noted that the purpose of this work was to use the virtual screening step to select peptides for the specific detection of ZIKV virus among different flaviviruses.

The docking results were used to select the arms of the clamp peptides for the experimental part. This selection was based on the peptide primary structure structural analysis results along with the position in the top ranked peptides and peptide length.

The primary structural analysis of the docking results was carried out to study the occurrence of the amino acids in the top 0.1% ranked peptides that maximized the recognition properties between the ZIKV active site and the other flaviviruses binding sites (DENV, West Nile and Chikungunya).

One peptide with high and one with low occurrence amino acids in primary structure were then chosen within the 0.1% top ranked peptides binding each of the two envelope protein active sites. The four peptides were selected from both penta and hexapeptide libraries, resulting in a total of 8 peptides, four pentapeptides and four hexapeptides.

Table 2 reports the results of the amino acid occurrence (%) in the primary structure of the eight peptides selected to build the clamp peptides. The occurrence was calculated counting the recurrence of each amino acid in the relative position (five positions for pentapeptides and six positions for hexapeptides) in the top 0.1% ranked peptides binding the active site 1 and 2 of the ZIKV envelope protein. The best occurrence amino acids were also reported, but peptides having all best occurrence amino acids were not present or were in the bottom of the 0.1% top rank peptides.

TABLE 2

Amino acid occurrence in the top 160 ranked peptides (%)

| | | 1P | 2P | 3P | 4P | 5P | Average |
| --- | --- | --- | --- | --- | --- | --- | --- |
| Active site 1 | SWPGQ (24) | 24.4 | 13.8 | 22.5 | 34.4 | 1.3 | 19.3% |
| | LRGHA (25) | 11.3 | 8.1 | 21.9 | 21.3 | 7.5 | 14.0% |
| | best occurrence AA: SMAGG (37) | *24.4* | *14.4* | *31.3* | *34.4* | *18.8* | *24.6%* |
| Active site 2 | WPHTQ (16) | 58.8 | 63.1 | 15.0 | 4.4 | 10.0 | 30.3% |
| | AGRRP (20) | 5.0 | 4.4 | 9.4 | 6.3 | 28.1 | 10.6% |
| | best occurrence AA: WPFFP (38) | *58.8* | *63.1* | *20.0* | *13.1* | *28.1* | *36.6%* |

| | | 1P | 2P | 3P | 4P | 5P | 6P | Average |
| --- | --- | --- | --- | --- | --- | --- | --- | --- |
| Active site 1 | KRNATP (26) | 10.0 | 6.3 | 28.8 | 56.9 | 34.4 | 41.9 | 29.7% |
| | KTDAYS (27) | 10.0 | 10.0 | 3.1 | 56.9 | 2.5 | 3.8 | 14.4% |
| | best occurrence AA: GPNATP (39) | *14.4* | *11.9* | *28.8* | *56.9* | *34.4* | *41.9* | *31.4%* |
| Active site 2 | WPWIGT (18) | 75.0 | 80.0 | 32.5 | 13.1 | 35.6 | 8.8 | 40.8% |
| | MDSPIK (22) | 1.3 | 0.6 | 1.3 | 2.5 | 1.9 | 2.5 | 1.7% |
| | best occurrence AA: WPWFGP (40) | *75.0* | *80.0* | *32.5* | *27.5* | *35.6* | *18.8* | *44.9%* |

Analysis of the amino acid occurrence (%) in the primary structure of the eight peptides selected to build the eight clamp peptides. The occurrence was calculated counting the recurrence of each amino acid in the relative position (five positions for pentapeptides and six positions for hexapeptides) in the top 0.1% ranked peptides binding the active site 1 and 2 of the ZIKV envelope protein. The best occurrence amino acids were also reported (in italic) along with the average (Av) percentage of the occurrence for each peptide.
SEQ ID NO: noted in ( ).

In the active site 1 of ZIKV envelop protein (glycosylation active site), the pentapeptide SWPGQ (SEQ ID NO: 24) and hexapeptide KRNATP (SEQ ID NO: 26) had almost all amino acids with high occurrence with some exception, the glutamine in fifth position for SWPGQ (SEQ ID NO: 24) and lysine in second position for KRNATP (SEQ ID NO: 26). The average in percentage of the occurrence (19.3% and 29.7%) was the highest of the top 0.1% ranked peptides in their respective libraries.

The other pentapeptide LRGHA (SEQ ID NO: 25) had amino acids with about half percentage of occurrence when compared to the top one in almost all the five positions. On the other hand, the hexapeptide KTDAYS (SEQ ID NO: 27) showed and alternate low and high occurrence percentage.

The penta and hexapeptides selected from the active site 2 docking, had similar high and low average occurrence amino acids in primary structure. Remarkably, the hexapeptides WPWIGT (SEQ ID NO: 18) and MDSPIK (SEQ ID NO: 22) had respectively the highest and lowest amino acids occurrence (40.8% and 1.7%) of the peptides selected to build the clamp peptides.

Table 3 shows the relative docking score position in the corresponding libraries of the eight peptides chosen to build the arms of the clamp peptides tested in the experimental evaluation. The ranking scores between the ZIKV sites and the other flaviviruses binding sites were for all peptides different enough to expect a ZIKV selective binding. Nevertheless, only three peptides ranked in the first 10 best peptides in binding ZIKV, highlighting strong similarities between the flaviviruses glycosylation sites. It should be noted that in all peptide libraries the simulated binding energy decreased exponentially in the top 1% best ranked peptides, in fact, a decrease of at least 20% in the binding score is observed for the $100^{th}$ peptide position.

TABLE 3

| Peptide (SEQ ID NO:) | ZIKV | DENV | West Nile | Chikungunya |
|---|---|---|---|---|
| Active site 1 Docking score rank | | | | |
| LRGHA (25) | 53 | 74900 | 69645 | 71784 |
| SWPGQ (24) | 4 | 55575 | 27840 | 47111 |
| KRNATP (26) | 16 | 85123 | 100716 | 74427 |
| KTDAYS (27) | 125 | 95558 | 110693 | 86882 |
| Active site 2 Docking score rank | | | | |
| WPHTQ (16) | 9 | 47135 | 43238 | 45072 |
| AGRRP (20) | 13 | 29265 | 51031 | 18894 |
| WPWIGT (18) | 1 | 21334 | 9821 | 18311 |
| MDSPIK (22) | 46 | 10080 | 40000 | 7831 |

Relative docking score position of the four pentapeptides and four hexapeptides selected for building the eight clamp peptides. The ranking obtained from the two active sites of the ZIKV envelope protein was compared to the one obtained using the other three flaviviruses envelope proteins.

The four pentapeptides and four hexapeptides were then combined to build eight clamp peptides. At this stage a mix between penta and hexapeptides was avoided in order to understand the contribution of the peptide length in the experimental responses.

Table 4 reports the physicochemical properties of the peptides selected for experimental evaluation. The peptides were the eight clamp peptides built using the combination of the penta or hexapeptides, and the mono-arm peta and hexapeptides binding the ZIKV envelope protein glycosylation binding site. Cysteine was inserted in the bridge of clamp peptides and at the N-terminus of mono-arm peptides to bind the maleimide-PEG$_2$-biotin used to label each of the peptides with the signal amplifier streptavidin-HRP.

TABLE 4

| Active site 2* | Bridge Peptide* | Active site 1* | Label | IsoPoint pH | net charge pH 7 | Water Sol | MW |
|---|---|---|---|---|---|---|---|
| WPHTQ (16) | GPGCCGPG (32) | SWPGQ (24) | C1 | 6.9 | 0.0 | poor | 1852 |
| WPHTQ (16) | GPGCCGPG (32) | LRGHA (25) | C2 | 8.1 | 1.1 | poor | 1831 |
| WPWIGT (18) | GPGCCGPG (32) | KRNATP (26) | C3 | 8.9 | 1.9 | poor | 2055 |
| WPWIGT (18) | GPGCCGPG (32) | KTDAYS (27) | C4 | 5.8 | -0.1 | poor | 2053 |
| AGRRP (20) | GPGCCGPG (32) | SWPGQ (24) | C5 | 12.1 | 2.0 | good | 1739 |
| AGRRP (20) | GPGCCGPG (32) | LRGHA (25) | C6 | 10.6 | 3.0 | good | 1718 |
| MDSPIK (22) | GPGCCGPG (32) | KRNATP (26) | C7 | 8.8 | 1.9 | good | 1986 |
| MDSPIK (22) | GPGCCGPG (32) | KTDAYS (27) | C8 | 5.9 | -0.1 | good | 1984 |
| | | C-SWPGQ (33) | P1 | 3.0 | -0.1 | poor | 676 |
| | | C-LRGHA (34) | P2 | 9.2 | 1.0 | good | 655 |
| | | C-KRNATP (35) | X1 | 10.5 | 1.9 | good | 788 |
| | | C-KTDAYS (36) | X2 | 5.9 | -0.1 | good | 786 |

Physicochemical properties of the eight peptides selected for experimental part. A cysteine was added to the N terminus of each mono-arm peptide to link the maleimide-PEG2-biotin.
*SEQ ID NOs: are noted in ( ).

The experimental analysis was performed in PBS at pH 7.4. Therefore, the physicochemical properties were focused on water solubility and net charge at pH 7. The first four clamp peptides and one of the mono-arm pentapeptide had poor water solubility due to the ratio of the hydrophobic amino acids, but when they were used at micromolar concentration were able to be dissolved in PBS. Five clamp peptides and two mono-arm peptides had a significant amount of positively charged amino acids resulting in a positive net charge at pH 7. Due to the presence of the polar amino acids the other peptides had a slightly negative net charge at pH 7.

Moreover, to highlight the positive or negative charges inside the peptide, the pH of the isoelectric point of each peptide was also reported. Interestingly, the majority of peptides selected had positively charged amino acids improving the possibility to interact with negative charges in the three-dimensional structure of both ZIKV binding sites selected.

maleimide-$PEG_2$-biotin reagent that reacts with the sulfhydryl group of the cysteine efficiently and specifically by forming a stable thioether bond. The antibody 4G2 hybridoma mouse IgG2a was used as the reference and employed in combination with an anti-mouse IgG conjugated to HRP.

All analytical parameters involved in the development of ELISA were optimized by using 96-well plates coated with triplicate 10-fold serial dilutions of intact ZIKV particles. The results were reported in Table 5.

TABLE 5

| | | C1 | C2 | C3 | C4 | C5 | C6 | C7 | C8 | P1 | P2 | X1 | X2 | AB 4G2 |
|---|---|---|---|---|---|---|---|---|---|---|---|---|---|---|
| Blocking Incubation buffer | | BT PBST | BT PBST | BT PBST | BT PBST | PF PBST | PF PBST | PF PBST | PF PBST | PF PBS | PF PBS | PF PBS | PF PBS | PF PBST |
| FPLR Dynamic Range | (log[ZIKV], copies/mL) | 5-7 | 5-7 | 4-7 | 6-7 | 6-7 | 4-7 | 4-7 | 5-7 | 7-8 | 5-7 | 5-7 | 6-8 | 6-8 |
| LOD | (log[ZIKV], copies/mL) | 4.8 | 4.5 | 3.5 | 5.7 | 5.8 | 3.5 | 3.7 | 4.7 | 6.8 | 4.5 | 4.8 | 5.8 | 5.8 |
| FPLR C50 | (log[ZIKV], copies/mL) | 6.3 | 6.2 | 5.3 | 6.3 | 6.4 | 5.2 | 5.8 | 6.2 | nd | 6.2 | 6.1 | 6.1 | 6.2 |
| FPLR slope | $\Delta A$/ (log[ZIKV]) | 33.2 | 25.4 | 8.7 | 32.8 | 25.6 | 10.1 | 5.3 | 33.9 | nd | 19.9 | 20.8 | 27.7 | 22.3 |
| FPLR maximum | $\Delta A$ | 0.43 | 0.55 | 0.67 | 0.40 | 0.17 | 0.53 | 0.95 | 0.82 | nd | 0.94 | 0.98 | 0.91 | 0.81 |
| FPLR minimum | $\Delta A$ | 0.03 | 0.05 | 0.05 | 0.02 | 0.01 | 0.05 | 0.01 | 0.03 | nd | 0.04 | 0.03 | 0.01 | 0.04 |
| FPLR $R^{-2}$ | | 0.98 | 1.00 | 0.99 | 1.00 | 0.97 | 0.99 | 0.99 | 0.99 | nd | 0.99 | 1.00 | 1.00 | 0.99 |
| Peptide Concentration | ($\mu M$) | 2 | 2 | 0.5 | 2 | 5 | 0.5 | 5 | 5 | 20 | 20 | 20 | 20 | 1 μg/ml |
| Intra-day reproducibility | CV (%) | <5 | <5 | <7 | <5 | <4 | <7 | <4 | <4 | <5 | <5 | <5 | <5 | <10 |
| Inter-day and batch-to-batch reproducibility | CV (%) | <12 | <12 | <15 | <12 | <10 | <15 | <10 | <10 | <10 | <10 | <10 | <10 | nd |
| Long-term stability | (Month) | >1 | >1 | >1 | >1 | >1 | >1 | >1 | >1 | >1 | >1 | >1 | >1 | nd |
| Assay time after Plate Coating | (h) | 5 | 5 | 5 | 5 | 5 | 5 | 5 | 5 | 5 | 5 | 5 | 5 | 8 |

Optimized experimental parameters of the direct ELISA assay for the eight clamp peptides, the four mono-arm peptides and a commercial antibody (4G2).
BT = BLOTTO blocking buffer;
PF = protein free blocking buffer;
PBS = 10 mM phosphate buffer saline pH 7.4;
PBST = 10 mM PBS pH 7.4, 0.1% Tween-20.
FLRP = Four Parameter Logistic Regression Experimental Results The eight clamp peptides and the four mono-arm peptides selected, were tested vs intact ZIKV particles by using a direct ELISA. The peptides were biotinylated by using the To minimize nonspecific binding, four blocking agents (PF, BLOTTO, SuperBlock™ Blocking Buffer, Blocker™ BSA) were tested. All blocking agents had very low background signal. For hydrophilic peptides the lowest background signal was achieved using PF that gave the best performances also using the antibody 4G2. For hydrophobic peptides, the blocker BLOTTO showed better performance, except for mono-arm peptide P1.

For clamp peptides and antibody, the surfactant agent tween 20 at 0.1% was necessary in the incubation step. No longer than one hour was necessary for peptide incubation, a longer time increased both the overall signal generated by the binding event and the background signal. Shacking during incubation improved the signal to noise ratio.

The optimal concentration of peptide was determined by coating clear 96-well plates with a solution of $10^7$ copies/mL of intact ZIKV particles. Concentrations of peptide, from 0.1 to 50 µM, diluted in 10 mM PBS pH 7.4 were added to wells of the microplates coated with intact ZIKV particles. For mono-arm peptides, larger concentrations than 20 µM did not increase the assay sensitivity.

Clamp peptides showed higher sensitivity than mono-arm peptides. Clamp peptides C5, C7 and C8 showed the best performances when used at 5 µM. The clamp C1, C2 and C4 at concentration of 2 µM did the best signal to noise ratio. Impressively, clamp peptides C3 and C6 had be used at concentration of 0.5 µM to have the best results, highlighting the remarkable high sensitivity of those peptides in this kind of assay.

Thus, the peptide concentrations reported in Table 5 were used to estimate the dynamic range and the LOD of the assay by using 10-fold serial dilutions of intact ZIKV particles from $10^1$ to $10^8$ copies/mL.

The results had a sigmoidal ZIKV particles concentration response and the calibration curves were obtained by plotting the delta absorbance (after blank signal subtraction) against the log of ZIKV particles concentration and fitting the experimental data with a four-parameter logistic function (FPLR).

Figure 3:
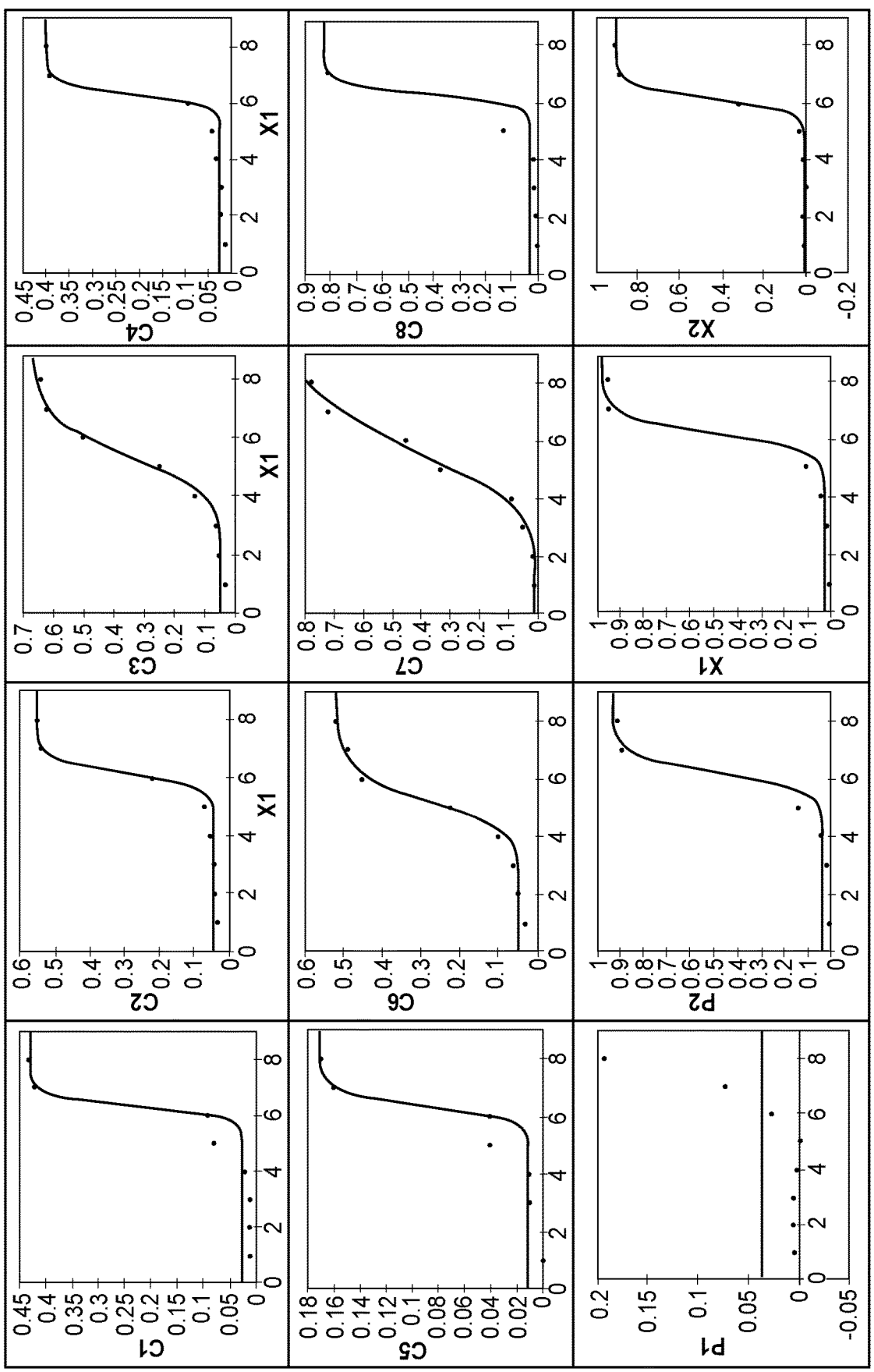
FIG. 3 is a series of graphs depicting the sigmoidal ZIKV particles concentration response trend. Y axis=Δ absorbance (450 nm); X-axis=log [ZIKV], copies/mL.

The regression parameters of the assay were reported in Table 5 and the sigmoidal trend in FIG. 3. The LOD was interpolated from the calibration curves using LOD=$S_B$+3× $SD_B$ where $S_B$ and $SD_B$ were the average and the standard deviation of the blank measurements, respectively.

Dose-response curves generated with all peptides and the antibody had at least two-order of magnitude dynamic range except for peptide P1, which had just a one order of magnitude dynamic range.

The peptide based assay using C3, C6, and C7 showed three-order of magnitude dynamic range and lower detection limits with dynamic range starting from $10^4$ copies/mL one or two order magnitude lower than the others peptides or antibody based assay. The better performance in binding ZIKV intact particles by those three clamp peptides was also highlighted by the FPLR C50 parameter. The dose-response performance of the assay was reproducible over a month (RSD lower than 15%), demonstrating that the peptides had high stability and reproducibility.

The cross-reactivity among Flaviviruses is a key parameter to be tested for this assay. Using the same ELISA protocol, the three clamp peptides (C3, C6 and C7) with higher sensitivity versus the intact ZIKV particles where employed to test the ability to discriminate ZIKV from the three serotypes of DENV (DENV-1, -2 and -3). The cross reactivity performances were compared with that obtained using the mono-arm peptides P2 and X1, that showed the best analytical parameters within the mono-arm peptides.

Figure 4:
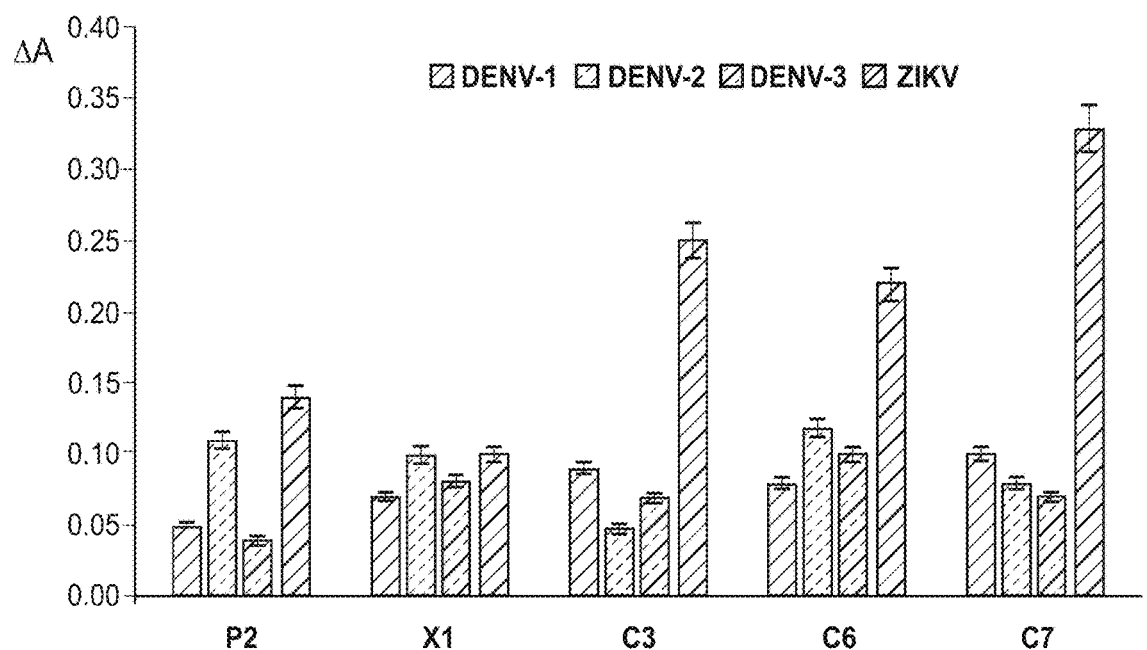
FIG. 4 is a graph of the Δ spectrophotometric absorbance signals obtained in a cross-reactivity study using the ELISA direct assay for the best three clamp peptides (C3, C6 and C7) and two mono-arm peptides (P2 and X1) binding the Zika (ZIKV) target protein (yellow) and three serotypes of Dengue virus (DENV-1 (blue), DENV-2 (orange) and DENV-3 (grey)) at the concentration of $10^5$ [ZIKV] copies/mL.
Figure 5:
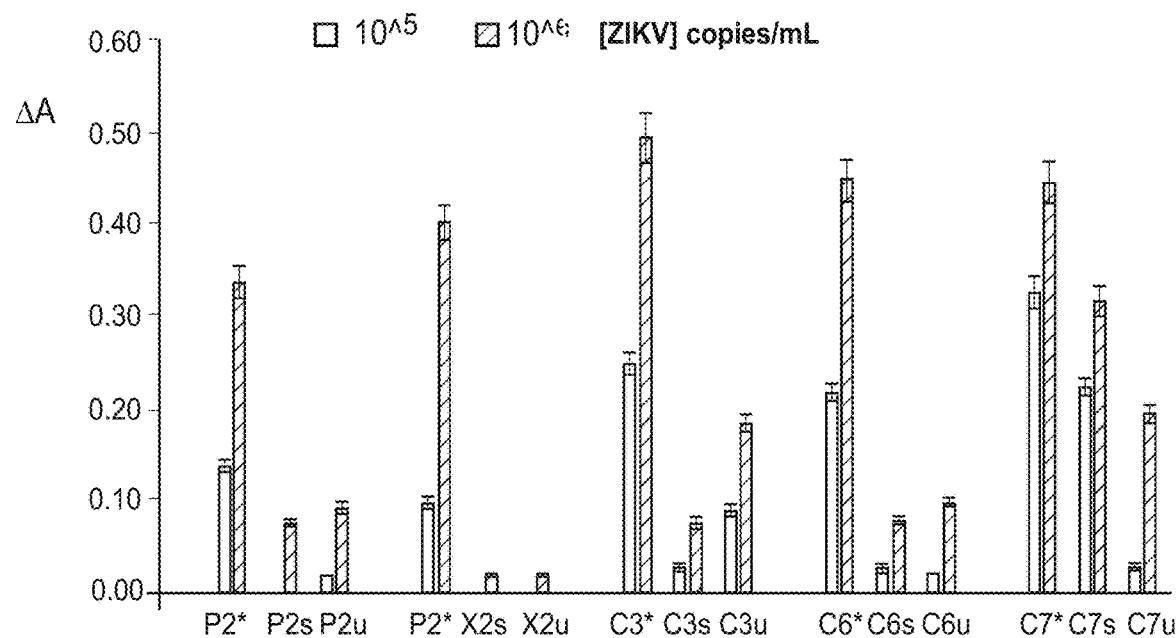
FIG. 5 is a graph of the Δ spectrophotometric absorbance signals obtained in a study using the ELISA direct assay for the best three clamp peptides (C3, C6 and C7) and two mono-arm peptides (P2 and X1) binding the Zika (ZIKV) target protein at a concentration of $10^5$ copies/ml (blue) or $10^6$ copies/mL (orange) in the presence of buffer (*), serum (s), or urine (u).

The results shown in FIG. 4 were obtained by coating clear 96-well plates with a solution of $10^5$ copies/mL of intact virus particles. At this concentration, all three peptides showed slight cross-reactivity against the DENV. Clamp peptides C3 and C7 had the higher DENV/ZIKV signal ratio with around 70% signal decrease for all DENV serotypes. Clamp Peptide C6 showed slight cross reactivity with DENV-2 and DENV-3 with only 45% and 55% of signal decrease respectively. The three clamp peptides clearly discriminated between the two flavivirus species. At this concentration, mono-arm peptide assays had the ZIKV delta absorbance signals statistically comparable to the signals obtained using DENV.

Nevertheless, it should be highlight that increasing the coating concentration of the virus to $10^6$ copies/mL the ZIKV and DENV analytical signals were statistically equivalent, losing, for the clamp peptides, the discrimination between ZIKV and DENV.

Usually, the presence of ZIKV in affected bodies is detected in biological fluids. Therefore, the analytical sensitivity of the selected peptides was tested in two biological matrices, namely, urine and serum. The matrix effect was investigated to understand how real biological fluids could modify the binding efficiency of the peptides.

FIG. 4 depicts the ELISA data using solutions of peptides with or without the urine and serum obtained coating clear 96-well plates with $10^5$ and $10^6$ copies/mL of intact ZIKV particles. Urine and serum were 1:1 and 1:10 diluted, respectively, with a concentrated peptide PBS solution (10 mM PBS, pH 7.4) to obtain a peptide final concentration of 0.5 µM for C3 and C6, 5 µM for C7 and 20 µM for mono-arm peptides (P2 and X1).

Clamp peptide C3 showed a better performance in urine than serum, particularly for $10^5$ copies/mL. Clamp peptide C6 had a strong decrease in the signal generated at both $10^5$ or $10^6$ copies/mL in both urine and serum. Clamp peptide C7 exhibited the best performance among the three clamp peptides, having higher signals in serum than in urine. All clamp peptides lost at the least one order of magnitude signal detecting ZIKV in urine or serum, except for C7 in serum, having a distinct analytical signal also at $10^5$ copies/mL of ZIKV.

Mono-arm peptides lost completely the signal at $10^5$ copies/mL of ZIKV, starting to detect ZIKV particles in both urine or serum, from $10^6$ copies/mL using P1 and from $10^7$ copies/mL using X1 (data not showed).

It should be highlighted that when a body is under a ZIKV infection the level of flavivirus concentration in urine can be up to $10^{6.9}$ copies/mL (Campos et al., 2016; Pawley et al., 2019).

Conclusions

The semi combinatorial virtual strategy to design clamp peptides using the two flavivirus active sites as a binding target has shown to have the potential for designing antibody mimetics for the selective detection of ZIKV.

The ELISA assay platform developed for testing the newly designed clamp peptides offered the possibility to optimize in short time the experimental conditions for evaluation of the eight clamp peptides and four mono-arm peptides chosen from the most promising ones yield by the in-silico studies. The three clamp peptides with better performances to detect ZIKV had shown to have also semi-selective properties when tested against DENV. The matrix-effect was also investigated, by testing the response of the peptides in physiological matrices, i.e., urine and serum. We observed that the matrix affected the assay performance by decreasing the detection limits by one order of magnitude, albeit still having a distinct analytical signal starting from $10^6$ copies/mL, the concentration of ZIKV in acute infection.

This work represents a new methodology for the selection of tailor-made clamp peptides, rationalizing the way to choose receptors with high binding ability among thousands of potential compounds that can be employed in biotechnology, medical, and a variety of analytical applications. Taking advantage of the fast progress in computing, we envision that it will be possible to simulate in short time the clamp peptides having even more complex shapes with better selectivity and less cross-reactivity.

Example 2

This example demonstrates the development of a ZIKV point of care (POC) test for direct detection of active exposure to ZIKV.

A point of care (PoC) lateral flow assay (immunochromatographic assay) to detect the presence of ZIKV is developed. The lateral flow principle is (1) easy to use, (2) fast, (3) stable at different storage conditions, (4) portable, and (5) inexpensive. These characteristics make these types of assays ideally suited for home, PoC, and field tests in developed and developing countries, as well as in urban and/or rural settings, and even in remote locations.

A lateral flow assay is prepared as follows: a rectangular sheet of nitrocellulose membrane is cut to the required dimensions (0.5 cm×5 cm). Nitrocellulose is a commonly used substrate for lateral flow assays and it is well established. Two test lines and a control line are laid down as thin strips using ink-jet printing technology. These zones contain a presently disclosed clamp peptide (zone A), a clamp peptide bound to ZIKV (zone B) and a 2ndary antibody that binds to the clamp peptide (zone C). The membrane is dried for 1 hour at RT and soaked with an aqueous solution of 1.0% polyvinyl alcohol (PVA) for 30 min at room temperature to make the nitrocellulose more hydrophobic and facilitate the flow of the reagents. The membrane is washed with deionized water to remove excess blocking reagents, such as PVA, and is dried at 30° C. for 30 min. The proximal end of the nitrocellulose strip, the region that contains the nanoparticle conjugated clamp peptide, is prepared by applying a 30% solution of sucrose followed by baking for 1 hour at 40° C. Sucrose is typically used in lateral flow assays as a preservative and facilitates the long-term storage of the nanoparticle conjugated clamp peptides. It also has the advantage of being inert towards typical assay chemistries. This region, (labeled as Particle Conjugate in FIG. 6) contains the clamp peptide conjugated to a nanoparticle such as gold or polystyrene. The collected patient samples are applied to sample application pad at the proximal end of the test strip. The sample application pad is usually made of cellulose or glass fiber and the sample is applied onto this pad to start the assay. The sample may also be treated in this region to make it compatible with the rest of the test. The treatments may include removal of red blood cells from the serum, removal of interferences from the sample, adjustment of pH, etc. The sample then migrates, through capillary action, through the nitrocellulose strip to the Particle Conjugate region. If the sample contains ZIKV, the dried clamp peptide conjugated to the nanoparticles are remobilized and the ZIKV particles bind to these conjugated clamp peptides. The formed complexes flow through the reaction matrix, which is usually a porous matrix such as nitrocellulose. This matrix also contains the other biological components of the assay, again laid down as thin, narrow bands using ink jet printing. In the first band (zone A) the clamp peptide is immobilized. The labeled ZIKV is then captured by the immobilized clamp peptide forming a colored band. Immobilized secondary antibodies present in the third zone serve as a positive control for both tests. The results are interpreted as the presence and absence of lines of the captured conjugate that can be read either by eye or by using a hand-held, battery operated, smart-phone based absorbance, fluorescence or luminescence reader. The type of the reader depends on the type of the labels conjugated to the clamp peptides. Therefore, the presence of two bands (zone A and B) indicates ZIKV viremia. A single band in the control zone C indicates a negative result for an active ZIKV infection. The absence of a colored band in either of the test indicates a failed test. Since this lateral flow test is a self-contained, self-reporting device, the need for elaborate laboratory equipment is eliminated.

REFERENCES

The following references are cited throughout Example 1.

Acebes et al., *ACS Catalysis* 6(3), 1624-1629 (2016).
Barba-Spaeth et al., *Nature* 536(7614), 48. (2016).
Bunker et al., *Biochimica et Biophysica Acta* (*BBA*)-*Biomembranes* 1858(10), 2334-2352 (2016).
Campos et al., *Journal of Clinical Virology* 77, 69-70 (2016).
Do Thi Hoang Kim et al., *Theranostics* 8(13), 3629 (2018).
Gong et al., *Yi Chuan* 32(6), 548-554 (2010).
Hawkins et al., *Journal of Chemical Information and Modeling* 52(11), 2919-2936. doi: 10.1021/ci300314 k.
Hawkins et al., *Journal of Chemical Information and Modeling* 50(4), 572-584. doi: 10.1021/ci100031x. (2010)
Heffron et al., *PLoS neglected tropical diseases* 12(11), e0006903 (2018).
Hwang et al., *Biosensors and Bioelectronics* 87, 164-170 (2017).
Ioos et al., *Medecine et maladies infectieuses* 44(7), 302-307 (2014).
Kelley et al., POSIT: flexible shape-guided docking for pose prediction. *Journal of chemical information and modeling* 55(8), 1771-1780 (2015).
Li et al., Electrochemical aptamer-based sensors for food and water analysis: A review. *Analytica chimica acta*. (2018)
Lin et al., *Journal of Chromatography A* 1446, 34-40 (2016).
Macalino et al., *Archives of pharmacal research* 38(9), 1686-1701 (2015).
Magnani et al., *Science translational medicine* 9(410), eaan8184 (2017).
Mascini et al., *Biosensors and Bioelectronics* 123, 124-130 (2019).
Mascini et al., *Talanta* 167, 126-133 (2017).
Michaeli et al., *The Journal of Immunology* 201(11), 3383-3391 (2018).
OEDocking. version 3.0.0. OpenEye Scientific Software, Santa Fe, N. Mex. http://www.eyesopen.com.
OMEGA. version 2.4.6. OpenEye Scientific Software, Santa Fe, N. Mex. http://www.eyesopen.com.
Palzkill et al., U.S. patent application Ser. No. 14/777,714), (2018)
Pawley et al., *ACS Omega* 4(4), 6808-6818 (2019).
Perez et al., Peptides trapping dioxins: a docking-based inverse screening approach. *Journal of Chemistry* 2013.
Pichon et al., *Anal Bioanal Chem* 407(3), 681-698. doi: 10.1007/s00216-014-8129-5 (2015).
Priyamvada et al., *Proceedings of the National Academy of Sciences* 113(28), 7852-7857 (2016).
Singh et al., *Journal of medicinal chemistry* 59(8), 3920-3934 (2016).
Sirohi et al., *Science* 352(6284), 467-470 (2016).
Stettler et al., *Science* 353(6301), 823-826 (2016).
Stobiecka et al., *Chemical Papers* 69(1), 62-76 (2015).
SZYBKI. version 1.5.7. OpenEye Scientific Software, Santa Fe, N. Mex. http://www.eyesopen.com.
Tambunan et al., *Jurnal Teknologi* 78(4-3) (2016).
Tang et al., *Talanta* 146, 55-61 (2016).

VIDA. version 4.1.1. OpenEye Scientific Software, Santa Fe, N. Mex. http://www.eyesopen.com.
Weaver et al., *Antiviral research* 130, 69-80 (2016).
Xu et al., *Nature medicine* 24(6), 857 (2018)
Yu et al., *Annual Review of Analytical Chemistry* 10, 293-320 (2017).
Yuan et al., *Wiley Interdisciplinary Reviews: Computational Molecular Science* 7(2), e1298 (2017).
Zhao et al., Structural basis of Zika virus-specific antibody protection. *Cell* 166(4), 1016-1027 (2016).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. An assay system comprising a porous matrix comprising at least three zones, Zone A, Zone B, and Zone C, wherein Zone A comprises a binding construct that binds to a Zika virus (ZIKV) protein and does not bind to a Dengue virus (DENV) protein, wherein the binding construct is not bound to a Zika virus, Zone B comprises a binding construct that binds to a ZIKV protein and does not bind to a DENV protein, wherein the binding construct is bound to a Zika virus, and Zone C comprises a secondary antibody which binds the binding construct of Zone A and Zone B, wherein (A) the ZIKV protein is from a ZIKV comprising the genome of GenBank Accession No. KU926309.1 (SEQ ID NO: 4); (B) the binding construct is an antibody mimetic, optionally, a clamp peptide; (C) the binding construct comprises the structure $A_1$-B-$A_2$ wherein $A_1$ is a first peptide arm that binds to a first binding site of a target protein, $A_2$ is a second peptide arm that binds to a second binding site of the target protein, and B is a bridge peptide which links $A_1$ to $A_2$, optionally, wherein the bridge peptide is about 5 to about 10 amino acids in length, further optionally, wherein (a) $A_1$ comprises an amino acid sequence of any one of SEQ ID NOs: 24-31, (b) $A_2$ comprises an amino acid sequence of any one of SEQ ID NOs: 16-23, or (c) a combination thereof.

2. The assay system of claim 1, wherein (D) the porous matrix comprises nitrocellulose of polyvinylidene fluoride (PVDF); (E) Zones A to C are arranged along a horizontal axis, wherein each of Zones A to C is flanked by an intervening zone of the porous matrix lacking the binding construct; (F) the method further comprises a sample application pad, a particle conjugate zone, a wick, and/or a backing; or (G) a combination thereof.

3. The assay system of claim 2, part (F), wherein the porous matrix, the sample application pad, the particle conjugate zone, and the wick are arranged along a horizontal axis, optionally, wherein the horizontal axis is the same as the horizontal axis along which Zones A to C are arranged, optionally, arranged such that the sample application pad and the wick are located at opposite ends of the assay system along the horizontal axis, wherein the particle conjugate zone is flanked by the sample application pad and the porous matrix and the porous matrix is flanked by the particle conjugate and the wick.

4. The assay system of claim 2, part (F), wherein the backing is positioned below the porous matrix, the sample application pad, the particle conjugate zone, and the wick; (ii) the particle conjugate zone is bound to a conjugate comprising a binding construct that binds to a Zika virus (ZIKV) protein and does not bind to a Dengue virus (DENV) protein, bound to an element or polymer, optionally, wherein the element is a gold particle or the polymer is polystyrene; (iii) the sample application pad comprises cellulose or glass fiber; (iv) the wick comprises nitrocellulose; or (v) each of Zone A and Zone B is bound to a binding construct.

5. The assay system of claim 1, wherein the binding construct does not bind to a protein of any one of DENV subtype 1, DENV subtype 2, DENV subtype 3, and DENV subtype 4, optionally, wherein the binding construct does not bind to any flavivirus other than ZIKV.

6. The assay system of claim 1, part (C), wherein $A_1$ comprises an amino acid sequence of SEQ ID NO: 26 and $A_2$ comprises an amino acid sequence of SEQ ID NO: 18 or $A_1$ comprises an amino acid sequence of SEQ ID NO: 25 and $A_2$ comprises an amino acid sequence of SEQ ID NO: 21 or $A_1$ comprises an amino acid sequence of SEQ ID NO: 26 and $A_2$ comprises an amino acid sequence of SEQ ID NO: 23.

7. The assay system of claim 1, part (C), wherein (A) the bridge peptide comprises the amino acid sequence of SEQ ID NO: 32, (B) the binding construct comprises an amino acid sequence of SEQ ID NO: 10, 13, or 14, or (C) a combination thereof.

* * * * *

UNITED STATES PATENT AND TRADEMARK OFFICE
CERTIFICATE OF CORRECTION

| | | |
|---|---|---|
| PATENT NO. | : 11,249,082 B2 | Page 1 of 1 |
| APPLICATION NO. | : 16/441388 | |
| DATED | : February 15, 2022 | |
| INVENTOR(S) | : Sylvia Daunert et al. | |

It is certified that error appears in the above-identified patent and that said Letters Patent is hereby corrected as shown below:

In the Claims

At Column 103, Line 24, Claim 4, "wherein" should be -- wherein (i) --.

Signed and Sealed this
Thirteenth Day of September, 2022

Katherine Kelly Vidal
*Director of the United States Patent and Trademark Office*